United States Patent
Wolfe et al.

(10) Patent No.: US 9,289,220 B2
(45) Date of Patent: Mar. 22, 2016

(54) INTRAMEDULLARY FIXATION ASSEMBLY AND METHOD OF USE

(75) Inventors: Scott Wolfe, Greenwich, CT (US); Jeff Tyber, Bethlehem, PA (US); Jamy Gannoe, West Milford, NJ (US); Adam Mantzaris, Hoboken, NJ (US)

(73) Assignee: Extremity Medical LLC, Parsippany, NJ (US)

( * ) Notice: Subject to any disclaimer, the term of this patent is extended or adjusted under 35 U.S.C. 154(b) by 400 days.

(21) Appl. No.: 13/227,235

(22) Filed: Sep. 7, 2011

(65) Prior Publication Data

US 2012/0197254 A1 Aug. 2, 2012

Related U.S. Application Data

(63) Continuation-in-part of application No. 12/906,454, filed on Oct. 18, 2010, now abandoned, which is a continuation-in-part of application No. 12/658,680, filed on Feb. 11, 2010, now Pat. No. 9,044,282, which (Continued)

(51) Int. Cl.
*A61B 17/04* (2006.01)
*F16B 15/00* (2006.01)
*A61B 17/17* (2006.01)

(Continued)

(52) U.S. Cl.
CPC ............. *A61B 17/1717* (2013.01); *A61B 17/68* (2013.01); *A61B 17/7291* (2013.01); *A61B 17/8605* (2013.01); *A61B 17/8625* (2013.01); *A61B 2017/1775* (2013.01);

(Continued)

(58) Field of Classification Search
CPC ........... A61B 17/7291; A61B 17/1717; A61B 17/8605; A61B 17/8625; F16B 5/0275
USPC ........... 606/54, 80, 96, 64–65, 301, 305–308, 606/310, 319; 411/457, 389
See application file for complete search history.

(56) References Cited

U.S. PATENT DOCUMENTS

| 71,909 A | * | 12/1867 | Pierce | F16B 35/042 |
| | | | | 411/389 |
| 83,225 A | * | 10/1868 | Tudor | F16B 33/002 |
| | | | | 403/256 |

(Continued)

FOREIGN PATENT DOCUMENTS

| WO | 2006116164 | 11/2006 |
| WO | 2007131287 | 11/2007 |
| WO | 2009120852 | 10/2009 |

*Primary Examiner* — Ellen C Hammond
*Assistant Examiner* — Stuart S Bray
(74) *Attorney, Agent, or Firm* — Kelley Brye & Warren LLP

(57) ABSTRACT

An intramedullary fixation assembly for bone fixation includes a first construct. The first construct includes a first tapered screw member fixated into a subchondral bone. The first tapered screw member is aligned along a first longitudinal axis and has a first head portion comprising a first aperture and a first shaft extending from the first head portion. Moreover, the first longitudinal axis of the first tapered screw member is aligned substantially parallel to an articular surface of a bone. The first construct also includes a first lag screw member aligned along a second longitudinal axis. The first lag screw member has a first bulbous portion and a second shaft extending from the first bulbous portion, wherein the first lag screw member is coupled to the first tapered screw member, and further wherein the second longitudinal axis of the first lag screw member is aligned generally along the length of the bone.

19 Claims, 36 Drawing Sheets

Related U.S. Application Data is a continuation-in-part of application No. 12/456,808, filed on Jun. 23, 2009, now Pat. No. 8,303,589.

(60) Provisional application No. 61/132,932, filed on Jun. 24, 2008.

(51) Int. Cl.
*A61B 17/68* (2006.01)
*A61B 17/72* (2006.01)
*A61B 17/86* (2006.01)
*F16B 5/02* (2006.01)
*A61F 2/42* (2006.01)

(52) U.S. Cl.
CPC ... *A61B 2017/1782* (2013.01); *A61F 2002/4238* (2013.01); *F16B 5/0275* (2013.01)

(56) References Cited

U.S. PATENT DOCUMENTS

| | | | | |
|---|---|---|---|---|
| 188,668 | A * | 3/1877 | Pleukharp | F16B 35/042 411/389 |
| 296,087 | A * | 4/1884 | Thomas | A63D 15/12 411/389 |
| 311,883 | A * | 2/1885 | England | F16B 7/182 24/31 C |
| 321,389 | A * | 6/1885 | Schirmer | F16B 35/042 16/4 |
| 375,907 | A * | 1/1888 | Whitmore | F16B 35/042 15/145 |
| 928,997 | A | 7/1909 | Muller | |
| 1,082,945 | A * | 12/1913 | Graham | F16B 35/042 403/362 |
| 1,672,879 | A * | 6/1928 | Campbell, Jr. | F16L 15/006 285/148.4 |
| 1,749,547 | A * | 3/1930 | Ruddy | F16B 12/24 164/385 |
| 1,897,196 | A * | 2/1933 | Hunt | F16B 23/0084 411/389 |
| 2,398,220 | A | 4/1946 | Gelpcke | |
| 2,580,821 | A | 1/1952 | Nicola | |
| 3,019,686 | A | 2/1962 | Behrle | |
| 3,200,694 | A * | 8/1965 | Rapata | F16B 13/02 174/153 G |
| 3,367,694 | A * | 2/1968 | Witt | F16B 33/004 403/389 |
| 3,407,382 | A * | 10/1968 | Haegert | H01R 11/281 411/389 |
| 3,411,398 | A * | 11/1968 | Blakeley | F16B 19/1054 411/41 |
| 3,474,537 | A | 10/1969 | Christensen | |
| 3,924,276 | A | 12/1975 | Eaton | |
| 4,152,533 | A | 5/1979 | Gazda | |
| 4,169,308 | A * | 10/1979 | Minogue | G09F 7/16 248/466 |
| 4,381,770 | A | 5/1983 | Neufeld | |
| 4,465,065 | A | 8/1984 | Gotfried | |
| 4,760,843 | A * | 8/1988 | Fischer | A61B 17/686 411/178 |
| 4,795,294 | A | 1/1989 | Takada | |
| 4,854,797 | A | 8/1989 | Gourd | |
| 4,930,963 | A | 6/1990 | Rockenfeller | |
| 4,940,467 | A * | 7/1990 | Tronzo | A61B 17/742 606/304 |
| 4,947,502 | A | 8/1990 | Engelhardt | |
| 4,987,714 | A * | 1/1991 | Lemke | E04D 3/3603 411/369 |
| 5,084,050 | A * | 1/1992 | Draenert | A61F 2/30767 606/304 |
| 5,112,333 | A | 5/1992 | Fixel | |
| 5,163,940 | A | 11/1992 | Bourque | |
| 5,209,753 | A | 5/1993 | Biedermann | |
| 5,350,380 | A | 9/1994 | Goble | |
| 5,403,321 | A | 4/1995 | DiMarco | |
| 5,456,267 | A | 10/1995 | Stark | |
| 5,478,341 | A | 12/1995 | Cook | |
| 5,501,557 | A | 3/1996 | Wakai | |
| 5,505,731 | A | 4/1996 | Tornier | |
| 5,531,748 | A | 7/1996 | de la Caffiniere | |
| 5,540,694 | A | 7/1996 | DeCarlo, Jr. | |
| 5,573,538 | A | 11/1996 | Laboureau | |
| 5,601,550 | A * | 2/1997 | Esser | A61B 17/1739 606/54 |
| 5,613,968 | A * | 3/1997 | Lin | A61B 17/7001 411/389 |
| 5,613,971 | A | 3/1997 | Lower | |
| 5,620,449 | A | 4/1997 | Faccioli | |
| 5,702,470 | A | 12/1997 | Menon | |
| 5,718,705 | A | 2/1998 | Sammarco | |
| 5,718,706 | A | 2/1998 | Roger | |
| 5,741,266 | A | 4/1998 | Moran | |
| 5,766,221 | A | 6/1998 | Benderev | |
| 5,769,583 | A * | 6/1998 | Girbinger | F16B 35/042 411/388 |
| 5,772,252 | A * | 6/1998 | Malani | F16B 31/021 285/337 |
| 5,779,704 | A | 7/1998 | Kim | |
| 5,857,816 | A | 1/1999 | Assmundson | |
| 5,865,559 | A | 2/1999 | Yang | |
| 5,888,203 | A | 3/1999 | Goldberg | |
| 5,891,150 | A | 4/1999 | Chan | |
| 5,968,050 | A | 10/1999 | Torrie | |
| 5,984,681 | A * | 11/1999 | Huang | A61C 8/001 433/173 |
| 5,997,541 | A | 12/1999 | Schenk | |
| D420,132 | S * | 2/2000 | Bucholz | A61C 8/001 D24/140 |
| 6,019,761 | A | 2/2000 | Gustillo | |
| 6,030,162 | A | 2/2000 | Huebner | |
| 6,048,343 | A | 4/2000 | Mathis | |
| 6,106,528 | A | 8/2000 | Durham | |
| 6,120,511 | A | 9/2000 | Chan | |
| 6,123,709 | A | 9/2000 | Jones | |
| 6,123,711 | A | 9/2000 | Winters | |
| 6,126,661 | A | 10/2000 | Faccioli | |
| 6,168,595 | B1 | 1/2001 | Durham | |
| 6,168,597 | B1 | 1/2001 | Bidermann | |
| 6,174,119 | B1 | 1/2001 | Orr | |
| 6,214,007 | B1 * | 4/2001 | Anderson | A61B 17/0401 606/304 |
| 6,214,012 | B1 * | 4/2001 | Karpman | A61B 17/864 606/246 |
| 6,221,074 | B1 | 4/2001 | Cole | |
| 6,235,031 | B1 | 5/2001 | Hodgeman | |
| 6,247,883 | B1 | 6/2001 | Monserratt | |
| 6,254,605 | B1 | 7/2001 | Howell | |
| 6,254,606 | B1 | 7/2001 | Carney | |
| 6,261,039 | B1 | 7/2001 | Reed | |
| 6,261,290 | B1 | 7/2001 | Friedl | |
| 6,270,499 | B1 | 8/2001 | Leu | |
| 6,280,442 | B1 | 8/2001 | Barker | |
| 6,287,313 | B1 | 9/2001 | Sasso | |
| 6,379,362 | B1 | 4/2002 | Birk | |
| 6,402,753 | B1 | 6/2002 | Cole | |
| 6,402,757 | B1 | 6/2002 | Moore | |
| 6,423,064 | B1 * | 7/2002 | Kluger | A61B 17/7037 403/373 |
| 6,435,788 | B2 | 8/2002 | Reed | |
| 6,443,954 | B1 | 9/2002 | Bramlet | |
| 6,458,134 | B1 * | 10/2002 | Songer | A61B 17/68 606/304 |
| 6,517,541 | B1 | 2/2003 | Sesic | |
| 6,527,775 | B1 | 3/2003 | Warburton | |
| 6,562,046 | B2 | 5/2003 | Sasso | |
| 6,569,165 | B2 * | 5/2003 | Wahl | A61B 17/7225 606/62 |
| 6,579,293 | B1 | 6/2003 | Chandran | |
| 6,589,245 | B1 | 7/2003 | Weiler | |
| 6,596,008 | B1 | 7/2003 | Kambin | |
| 6,626,916 | B1 | 9/2003 | Yeung | |
| 6,629,976 | B1 * | 10/2003 | Gnos | A61B 17/7291 606/62 |
| 6,632,057 | B1 | 10/2003 | Fauchet | |

(56) References Cited

U.S. PATENT DOCUMENTS

| | | |
|---|---|---|
| 6,634,844 B2 | 10/2003 | Huber |
| 6,648,889 B2 | 11/2003 | Bramlet |
| 6,669,700 B1 | 12/2003 | Farris |
| 6,679,888 B2 | 1/2004 | Green |
| 6,685,706 B2 | 2/2004 | Padget |
| 6,692,496 B1 | 2/2004 | Wardlaw |
| 6,692,503 B2 | 2/2004 | Foley |
| 6,695,844 B2 | 2/2004 | Bramlet |
| 6,709,436 B1 | 3/2004 | Hover |
| 6,712,849 B2 | 3/2004 | Re |
| 6,743,018 B1 | 6/2004 | Morrow |
| 6,778,861 B1 * | 8/2004 | Liebrecht ............ A61B 17/86 606/304 |
| 6,793,659 B2 | 9/2004 | Putnam |
| 6,808,527 B2 | 10/2004 | Lower |
| 6,849,093 B2 | 2/2005 | Michaelson |
| 6,875,216 B2 | 4/2005 | Wolf |
| 6,908,271 B2 * | 6/2005 | Breslin ............ F16B 13/126 411/271 |
| 6,951,538 B2 | 10/2005 | Ritland |
| 6,951,561 B2 | 10/2005 | Warren |
| 6,981,974 B2 | 1/2006 | Berger |
| 7,018,380 B2 * | 3/2006 | Cole ............ A61B 17/164 606/170 |
| 7,037,309 B2 | 5/2006 | Weil |
| 7,041,104 B1 | 5/2006 | Cole |
| 7,063,724 B2 | 6/2006 | Re |
| 7,074,221 B2 | 7/2006 | Michelson |
| 7,144,399 B2 | 12/2006 | Hayes |
| 7,160,302 B2 | 1/2007 | Warburton |
| 7,175,632 B2 | 2/2007 | Singhatat |
| 7,229,448 B2 | 6/2007 | Goble |
| 7,232,442 B2 | 6/2007 | Sohngen |
| 7,247,156 B2 | 7/2007 | Ekholm |
| 7,267,678 B2 | 9/2007 | Medoff |
| 7,326,248 B2 | 2/2008 | Michaelson |
| 7,331,962 B2 | 2/2008 | Branemark |
| 7,341,588 B2 | 3/2008 | Swanson |
| 7,344,538 B2 | 3/2008 | Myerson |
| 7,410,488 B2 | 8/2008 | Janna |
| 7,524,326 B2 * | 4/2009 | Dierks ............ A61B 17/7041 606/308 |
| 7,527,627 B2 * | 5/2009 | Ferrante ............ A61B 17/164 606/62 |
| 7,582,107 B2 * | 9/2009 | Trail ............ A61B 17/863 606/304 |
| 7,588,577 B2 | 9/2009 | Fencl |
| 7,591,819 B2 | 9/2009 | Zander |
| 7,601,153 B2 | 10/2009 | Shinjo |
| 7,608,097 B2 | 10/2009 | Kyle |
| 7,632,272 B2 | 12/2009 | Munro |
| 7,655,009 B2 | 2/2010 | Grusin |
| 7,666,212 B2 | 2/2010 | Pathak |
| 7,670,340 B2 | 3/2010 | Brivio |
| 7,713,271 B2 | 5/2010 | Warburton |
| 7,717,947 B1 * | 5/2010 | Wilberg ............ A61B 17/864 606/304 |
| 7,731,721 B2 | 6/2010 | Rathbun |
| 7,731,738 B2 * | 6/2010 | Jackson ............ A61B 17/8635 606/300 |
| 7,763,021 B2 | 7/2010 | Cole |
| 7,763,022 B2 | 7/2010 | Speitling |
| 7,763,023 B2 | 7/2010 | Gotfried |
| 7,771,428 B2 | 8/2010 | Siravo |
| 7,785,326 B2 | 8/2010 | Green |
| 7,794,483 B2 | 9/2010 | Capanni |
| 7,799,061 B2 | 9/2010 | Kay |
| 7,815,646 B2 | 10/2010 | Hart |
| 7,842,036 B2 * | 11/2010 | Phillips ............ A61B 17/7208 606/62 |
| 7,867,231 B2 | 1/2011 | Cole |
| 7,892,234 B2 | 2/2011 | Schlienger |
| 7,892,264 B2 | 2/2011 | Sanders |
| 7,909,825 B2 * | 3/2011 | Saravia ............ A61B 17/1725 606/63 |
| 7,914,532 B2 | 3/2011 | Shaver |
| 7,918,853 B2 | 4/2011 | Watanabe |
| 7,922,748 B2 * | 4/2011 | Hoffman ............ A61B 17/7037 606/264 |
| 7,927,340 B2 | 4/2011 | Hart |
| 7,938,848 B2 | 5/2011 | Sweeney |
| 7,947,043 B2 | 5/2011 | Mutchler |
| 8,034,056 B2 | 10/2011 | Fencl |
| 8,034,082 B2 | 10/2011 | Lee |
| 8,057,476 B2 | 11/2011 | Ekholm |
| 8,092,453 B2 | 1/2012 | Warburton |
| 8,100,910 B2 | 1/2012 | Warburton |
| 8,100,946 B2 | 1/2012 | Strausbaugh |
| 8,206,424 B2 | 6/2012 | Bidermann |
| 8,303,589 B2 * | 11/2012 | Tyber ............ A61B 17/1717 606/301 |
| 8,591,513 B2 * | 11/2013 | Overes ............ A61B 17/68 606/319 |
| 8,882,838 B2 * | 11/2014 | Reichen ............ A61F 2/4425 623/17.14 |
| 9,060,808 B2 * | 6/2015 | Overes ............ A61B 17/68 |
| 9,149,316 B2 * | 10/2015 | Appenzeller ........ A61B 17/864 |
| 2001/0021852 A1 | 9/2001 | Chappius |
| 2002/0032445 A1 | 3/2002 | Fujiwara |
| 2002/0052605 A1 | 5/2002 | Grooms |
| 2002/0128712 A1 * | 9/2002 | Michelson ............ A61F 2/446 623/17.11 |
| 2002/0143333 A1 | 10/2002 | von Hoffmann |
| 2002/0169453 A1 | 11/2002 | Berger |
| 2002/0197134 A1 | 12/2002 | Huber |
| 2003/0028193 A1 | 2/2003 | Weil |
| 2003/0060827 A1 | 3/2003 | Coughlin |
| 2003/0065391 A1 | 4/2003 | Re |
| 2003/0083667 A1 | 5/2003 | Ralph |
| 2003/0147716 A1 | 8/2003 | Nagawa |
| 2003/0158555 A1 | 8/2003 | Sanders |
| 2003/0229346 A1 * | 12/2003 | Oribe ............ A61B 17/70 606/246 |
| 2004/0006345 A1 * | 1/2004 | Vlahos ............ A61B 17/8625 606/916 |
| 2004/0082959 A1 | 4/2004 | Hayes |
| 2004/0097945 A1 | 5/2004 | Wolf |
| 2004/0172031 A1 * | 9/2004 | Rubecamp ........ A61B 17/8685 606/309 |
| 2004/0181234 A1 | 9/2004 | McDevitt |
| 2004/0193162 A1 | 9/2004 | Bramlet |
| 2004/0220570 A1 * | 11/2004 | Frigg ............ A61B 17/80 623/17.15 |
| 2005/0015092 A1 | 1/2005 | Rathbun |
| 2005/0069397 A1 * | 3/2005 | Shavit ............ A61B 17/744 411/457 |
| 2005/0107791 A1 * | 5/2005 | Manderson ............ A61B 17/68 606/62 |
| 2005/0125070 A1 | 6/2005 | Reiley |
| 2005/0149030 A1 * | 7/2005 | Serhan ............ A61B 17/7064 606/247 |
| 2005/0171544 A1 | 8/2005 | Falkner |
| 2005/0171546 A1 | 8/2005 | Wolf |
| 2005/0192580 A1 | 9/2005 | Dalton |
| 2005/0240190 A1 | 10/2005 | Gall |
| 2005/0251147 A1 | 11/2005 | Novak |
| 2005/0273101 A1 | 12/2005 | Schumacher |
| 2005/0277940 A1 | 12/2005 | Neff |
| 2005/0283159 A1 | 12/2005 | Amara |
| 2006/0009774 A1 | 1/2006 | Goble et al. |
| 2006/0009846 A1 | 1/2006 | Trieu |
| 2006/0015101 A1 | 1/2006 | Warburton |
| 2006/0052787 A1 | 3/2006 | Re |
| 2006/0095039 A1 | 5/2006 | Mutchler |
| 2006/0122600 A1 | 6/2006 | Cole |
| 2006/0122612 A1 * | 6/2006 | Justin ............ A61B 17/863 606/916 |
| 2006/0142770 A1 | 6/2006 | Capanni |
| 2006/0149244 A1 * | 7/2006 | Amrein ............ A61B 17/7032 606/264 |
| 2006/0173461 A1 * | 8/2006 | Kay ............ A61B 17/8625 606/304 |
| 2006/0189991 A1 * | 8/2006 | Bickley ............ A61B 17/864 606/916 |

(56) References Cited

U.S. PATENT DOCUMENTS

| | | | |
|---|---|---|---|
| 2006/0200141 A1 | 9/2006 | Janna | |
| 2006/0200143 A1 | 9/2006 | Warburton | |
| 2006/0200144 A1 | 9/2006 | Warburton | |
| 2006/0200160 A1 | 9/2006 | Border | |
| 2006/0206044 A1 | 9/2006 | Simon | |
| 2006/0235396 A1 | 10/2006 | Sanders | |
| 2006/0241608 A1 | 10/2006 | Myerson | |
| 2006/0241777 A1 | 10/2006 | Partin | |
| 2006/0264954 A1* | 11/2006 | Sweeney, II | A61B 17/8685 606/312 |
| 2007/0021839 A1 | 1/2007 | Lowe | |
| 2007/0038306 A1 | 2/2007 | O'Gara | |
| 2007/0055286 A1 | 3/2007 | Ralph | |
| 2007/0066977 A1 | 3/2007 | Assell | |
| 2007/0073290 A1 | 3/2007 | Boehm, Jr. | |
| 2007/0093841 A1 | 4/2007 | Hoogland | |
| 2007/0112432 A1 | 5/2007 | Reiley | |
| 2007/0162028 A1 | 7/2007 | Jackson | |
| 2007/0173835 A1 | 7/2007 | Medoff | |
| 2007/0233114 A1 | 10/2007 | Bouman | |
| 2007/0270848 A1 | 11/2007 | Lin | |
| 2007/0270855 A1 | 11/2007 | Partin | |
| 2008/0065224 A1 | 3/2008 | Reigstad | |
| 2008/0091203 A1 | 4/2008 | Warburton | |
| 2008/0154271 A1 | 6/2008 | Berberich | |
| 2008/0208261 A1 | 8/2008 | Medoff | |
| 2008/0221623 A1 | 9/2008 | Gooch | |
| 2008/0269908 A1 | 10/2008 | Warburton | |
| 2008/0279654 A1* | 11/2008 | Deschamps | E04F 15/02 411/457 |
| 2008/0294164 A1 | 11/2008 | Frank | |
| 2008/0306487 A1 | 12/2008 | Hat | |
| 2008/0306537 A1 | 12/2008 | Culbert | |
| 2009/0018542 A1 | 1/2009 | Saravia | |
| 2009/0048600 A1* | 2/2009 | Matityahu | A61B 17/7241 606/62 |
| 2009/0062797 A1 | 3/2009 | Huebner | |
| 2009/0088767 A1 | 4/2009 | Leyden | |
| 2009/0088804 A1 | 4/2009 | Kyle | |
| 2009/0088806 A1 | 4/2009 | Leyden | |
| 2009/0093813 A1 | 4/2009 | Elghazaly | |
| 2009/0093849 A1 | 4/2009 | Grabowski | |
| 2009/0093851 A1* | 4/2009 | Osman | A61B 17/7064 606/301 |
| 2009/0099571 A1 | 4/2009 | Cresina | |
| 2009/0149857 A1 | 6/2009 | Culbert | |
| 2009/0157077 A1 | 6/2009 | Larsen | |
| 2009/0157078 A1 | 6/2009 | Mikol | |
| 2009/0157079 A1 | 6/2009 | Warburton | |
| 2009/0157080 A1 | 6/2009 | Warburton | |
| 2009/0177203 A1 | 7/2009 | Reiley | |
| 2009/0198289 A1* | 8/2009 | Manderson | A61B 17/8685 606/304 |
| 2009/0209961 A1 | 8/2009 | Ferrante | |
| 2009/0240252 A1* | 9/2009 | Chang | A61B 17/1725 606/96 |
| 2009/0248025 A1 | 10/2009 | Haidukewych | |
| 2009/0264885 A1 | 10/2009 | Grant | |
| 2009/0281580 A1* | 11/2009 | Emannuel | A61B 17/8685 606/304 |
| 2009/0292292 A1 | 11/2009 | Fencl | |
| 2009/0306666 A1* | 12/2009 | Czartoski | A61B 17/72 606/64 |
| 2009/0306671 A1* | 12/2009 | McCormack | A61B 17/025 606/90 |
| 2009/0326534 A1 | 12/2009 | Yamazaki | |
| 2010/0023011 A1* | 1/2010 | Nakamura | A61B 17/746 606/64 |
| 2010/0023064 A1 | 1/2010 | Brunger | |
| 2010/0030280 A1 | 2/2010 | Jackson | |
| 2010/0042164 A1* | 2/2010 | Lee | A61B 17/686 606/304 |
| 2010/0042167 A1* | 2/2010 | Nebosky | A61B 17/7061 606/315 |
| 2010/0057141 A1* | 3/2010 | Abdelgany | A61B 17/8685 606/310 |
| 2010/0069970 A1* | 3/2010 | Lewis | A61B 17/8605 606/301 |
| 2010/0076499 A1* | 3/2010 | McNamara | A61B 17/0401 606/304 |
| 2010/0121324 A1 | 5/2010 | Tyber | |
| 2010/0121325 A1* | 5/2010 | Tyber | A61B 17/1717 606/62 |
| 2010/0174284 A1 | 7/2010 | Schwammberger | |
| 2010/0179551 A1* | 7/2010 | Keller | A61B 17/744 606/67 |
| 2010/0234846 A1 | 9/2010 | Eglseder | |
| 2010/0256638 A1* | 10/2010 | Tyber | A61B 17/1717 606/62 |
| 2010/0256639 A1* | 10/2010 | Tyber | A61B 17/1717 606/62 |
| 2010/0312279 A1* | 12/2010 | Gephart | A61B 17/3421 606/264 |
| 2010/0324556 A1* | 12/2010 | Tyber | A61B 17/72 606/62 |
| 2011/0004255 A1* | 1/2011 | Weiner | A61B 17/1682 606/301 |
| 2011/0022066 A1* | 1/2011 | Sevrain | A61B 17/86 606/151 |
| 2011/0046681 A1* | 2/2011 | Prandi | A61B 17/8004 606/286 |
| 2011/0060337 A1 | 3/2011 | Ferrante | |
| 2011/0118739 A1* | 5/2011 | Tyber | A61B 17/1717 606/62 |
| 2011/0125153 A1* | 5/2011 | Tyber | A61B 17/1717 606/62 |
| 2011/0137313 A1 | 6/2011 | Jensen | |
| 2011/0144645 A1 | 6/2011 | Saravia | |
| 2011/0160729 A1 | 6/2011 | Overes | |
| 2011/0213367 A1* | 9/2011 | Tyber | A61B 17/1717 606/62 |
| 2011/0218580 A1* | 9/2011 | Schwager | A61B 17/863 606/308 |
| 2011/0230884 A1* | 9/2011 | Mantzaris | A61B 17/1717 606/64 |
| 2011/0282398 A1* | 11/2011 | Overes | A61B 17/861 606/304 |
| 2011/0301651 A1 | 12/2011 | Kirschman | |
| 2012/0004690 A1* | 1/2012 | Gonzalez-Hernandez | A61B 17/8695 606/305 |
| 2012/0010669 A1* | 1/2012 | O'Neil | A61B 17/7064 606/305 |
| 2012/0016424 A1* | 1/2012 | Kave | A61B 17/7037 606/305 |
| 2012/0022603 A1* | 1/2012 | Kirschman | A61B 17/7064 606/305 |
| 2012/0078373 A1* | 3/2012 | Gamache | A61B 17/8625 623/17.16 |
| 2012/0095516 A1* | 4/2012 | Dikeman | A61B 17/7032 606/305 |
| 2012/0109213 A1* | 5/2012 | Appenzeller | A61B 17/68 606/281 |
| 2012/0197254 A1* | 8/2012 | Wolfe | A61B 17/1717 606/62 |

* cited by examiner

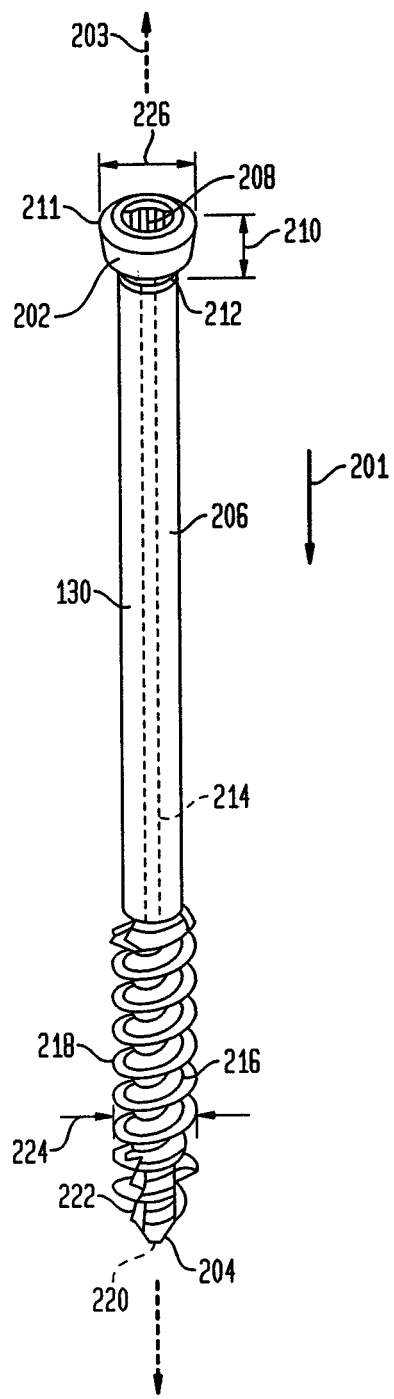

INTRAMEDULLARY FIXATION ASSEMBLY AND METHOD OF USE

CROSS-REFERENCE TO RELATED APPLICATIONS

This application is a continuation-in-part application of application Ser. No. 12/906,454, filed Oct. 18, 2010, which is a continuation-in-part application of application Ser. No. 12/658,680, filed Feb. 11, 2010, which is a continuation-in-part application of application Ser. No. 12/456,808, filed Jun. 23, 2009, which claims the benefit of Provisional Application No. 61/132,932, filed Jun. 24, 2008, the entire contents of the entire chain of applications are herein incorporated by reference.

FIELD OF THE INVENTION

This invention relates to the field of orthopedic implant devices, and more particularly, to an intramedullary fixation assembly used for fusion of the angled joints, bones and deformity correction, such as the hand, foot, arm, and leg bones.

BACKGROUND OF THE INVENTION

Orthopedic implant devices, such as intramedullary nails, plates, rods, screws, Kirschner wires ("K-wires"), and screw and washer assemblies are often used to repair or reconstruct bones and joints affected by trauma, degeneration, deformity, fractures, and disease, such as Charcot arthropathy caused by diabetes in some patients, Hallux Valgus deformities, failed Keller Bunionectomies, Rheumatoid Arthritis, injuries, and severe deformities.

Moreover, infections and wound complications are a major concern in the aforementioned procedures. Wound closure is technically demanding for the surgeon, and devices that add surface prominence, such as plates or exposed screws, add to the difficulty by requiring greater tissue tension during incision reapproximation. This increases the risk of postoperative wound infections and dehiscence that may ultimately result in limb amputation.

Various implants have been utilized for surgical treatment of these bones and joints, including bone screws. Implants have also been utilized to treat severe deformities in the metatarsal and phalangeal bones, including multiple screws and plates. These multiple screws and plate implants have been commonly used in a first metatarsal-phalangeal fusion procedure to fuse the first metatarsal to the first phalangeal bone in hallux valgus deformities, failed Keller bunionectomies, rheumatoid arthritis, and other types of severe deformities in the metatarsal and phalange bones. While these devices allow fixation and promote fusion, they do not deliver restoration of the arch in a Charcot foot, they are not effective in metatarsal-phalangeal (MTP) fusion procedures, nor do they deliver uniform compression for various predetermined angles of compression.

Particularly, screw implants in MTP procedures are ineffective in delivering sufficient compression to the bones in the foot, preventing screw head break out, or delivering effective bending resistance. Moreover, hard to control dorsiflexion and valgus angles as well as skin irritation from proximity to the skin prevents these screw implants from being readily utilized for surgical treatment. Yet further, plate implants used with bone screws too have the same drawbacks as fixed varus and valgus angles, lack of direct compression across the MTP joint, and skin irritations from proximity to the skin reduce the effectiveness of these implants. Yet further, some screw implants are not available to be readily interchangeable from a fixed angle compression to a variable angle compression while utilizing a common bone anchor and minimizing the members required by a surgeon.

Still further, use of K-wires, screws, screw and washer assemblies, and plates for the reduction and internal fixation of arthrodesis, osteotomy, intra-articular and extra-articular fractures, and non-unions of bones and joints of the hand, foot, arm, leg and various other body parts are ineffective in delivering the strength necessary to maintain sufficient reduction and/or fixation of the fractured bone, maximizing cortical bone contact, retaining bones in most anatomically correct position, preventing screw head break out, minimizing the size of the incision(s) necessary to install the hardware, minimizing soft tissue and tendon disruption and/or displacement, stabilizing fixation of the fracture, easing mobility for the patient, and eliminating hardware profiles.

There is therefore a need for an intramedullary fixation assembly and method of use that overcomes some or all of the previously delineated drawbacks of prior fixation assemblies.

SUMMARY OF THE INVENTION

An object of the invention is to overcome the drawbacks of previous inventions. Another object of the invention is to provide a novel and useful intramedullary fixation assembly that may be utilized to treat bones in a human body.

Another object of the invention is to provide a system for compressing bones using an intramedullary fixation assembly.

Another object of the invention is to fuse bones through the use of an intraosseous assembly.

Another object of the invention is to provide a novel intramedullary fixation assembly that incorporates design characteristics of both non-locking and locking screws.

Another object of the invention is to provide a novel intramedullary fixation assembly that is securely assembled by securing the lag screw member to the tapered screw member via a threaded connection or threaded engagement.

Another object of the invention is to provide a fixed acute angle intramedullary fixation assembly for bone fixation.

Another object of the invention is to provide variable acute angles of fixation. Another object of the invention is to provide a variable acute angle intramedullary fixation assembly for bone fixation.

Another object of the invention is to provide at least three points of compression on bone fragments through a variable angle intramedullary fixation assembly.

Another object of the invention is to provide an intramedullary fixation assembly that provides sufficient strength to delivery a highly stable fixation and maintain reduction of a fractured bone.

Another object of the invention is to provide an intramedullary fixation assembly that maximizes cortical bone contact.

Another object of the invention is to provide an intramedullary fixation assembly that fixates to the subchondral bone and/or the cortical bone.

Another object of the invention is to provide an intramedullary fixation assembly that retains and realigns bones in the most anatomically correct positions.

Another object of the invention is to provide an intramedullary fixation assembly that reduces and/or eliminates unnecessary hardware.

Another object of the invention is to provide an intramedullary fixation assembly that minimizes the size of the incision(s) necessary to install the intramedullary fixation assembly.

Another object of the invention is to provide an intramedullary fixation assembly that minimizes soft tissue and tendon disruption and/or displacement.

Another object of the invention is to provide an intramedullary fixation assembly that allows for early post procedure mobilization of the patient.

Another object of the invention is to provide an intramedullary fixation assembly that reduces and/or eliminates hardware profiles.

Another object of the invention is to provide a method for the reduction and fixation of arthrodesis, osteotomy, intra-articular and extra-articular fractures and non-unions of bones and joints of the hand, foot, arm, leg and various other body parts.

In a first non-limiting aspect of the invention, an intramedullary fixation assembly for bone fixation is provided and includes a first construct. The first construct includes a first tapered screw member fixated into a subchondral bone. The first tapered screw member is aligned along a first longitudinal axis and has a first head portion comprising a first aperture and a first shaft extending from the first head portion. Moreover, the first longitudinal axis of the first tapered screw member is aligned substantially parallel to an articular surface of a bone. The first construct also includes a first lag screw member aligned along a second longitudinal axis. The first lag screw member has a first bulbous portion and a second shaft extending from the first bulbous portion, wherein the first lag screw member is coupled to the first tapered screw member, and further wherein the second longitudinal axis of the first lag screw member is aligned generally along the length of the bone.

In a second non-limiting aspect of the invention, an intramedullary fixation assembly for bone fixation is provided and includes a first construct and a second construct. The first construct includes a first tapered screw member aligned along a first longitudinal axis. The first tapered screw member has a first head portion comprising a first aperture and a first shaft extending from the first head portion, wherein the first longitudinal axis of the first tapered screw member is aligned substantially parallel to an articular surface of a bone. The first construct also includes a first lag screw member aligned along a second longitudinal axis. The first lag screw member has a first bulbous portion and a second shaft extending from the first bulbous portion, wherein the first lag screw member is coupled to the first tapered screw member, and further wherein the second longitudinal axis of the first lag screw member is aligned generally along the length of the bone. The second construct includes a second tapered screw member aligned along a third longitudinal axis. The second tapered screw member has a second head portion comprising a second aperture and a third shaft extending from the second head portion, wherein the third longitudinal axis is aligned substantially parallel to a lunate articular surface of the bone. The second construct also includes a second lag screw member aligned along a fourth longitudinal axis. The second lag screw member has a second bulbous portion and a fourth shaft extending from the second bulbous portion, wherein the second lag screw member is coupled to the second tapered screw member, and further wherein the fourth longitudinal axis of the first lag screw member is aligned generally along the length of the bone.

In a third non-limiting aspect of the invention, an intramedullary fixation assembly for bone fixation is provided and includes a tapered screw member and a lag screw member. The tapered screw member has a head portion comprising an aperture and a first shaft extending from the head portion. The lag screw member has a bulbous portion and a second shaft extending from the bulbous portion. The intramedullary fixation assembly also includes a first plurality of threads disposed substantially along the circumference of an interior surface of the aperture and a second plurality of threads disposed substantially along the circumference of an exterior surface of the bulbous portion, wherein the first plurality of threads are adapted to be coupled to the second plurality of threads.

In a fourth non-limiting aspect of the invention, a method for fixating a bone includes several steps. In one non-limiting step, a first medullary canal is drilled in a subchondral bone. In another non-limiting step, a first tapered screw member is fixated into the first medullary canal in the subchondral bone. In another non-limiting step, a second medullary canal is drilled in the bone. In another non-limiting step, a first lag screw member is coupled to the first tapered screw member. In another non-limiting step, the first lag screw member is fixated into the second medullary canal.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which:

FIG. 2 is a perspective view of a proximal screw member used in the fixation system shown in FIG. 1 according to the preferred embodiment of the invention;

DETAILED DESCRIPTION OF THE INVENTION

Figure 1:
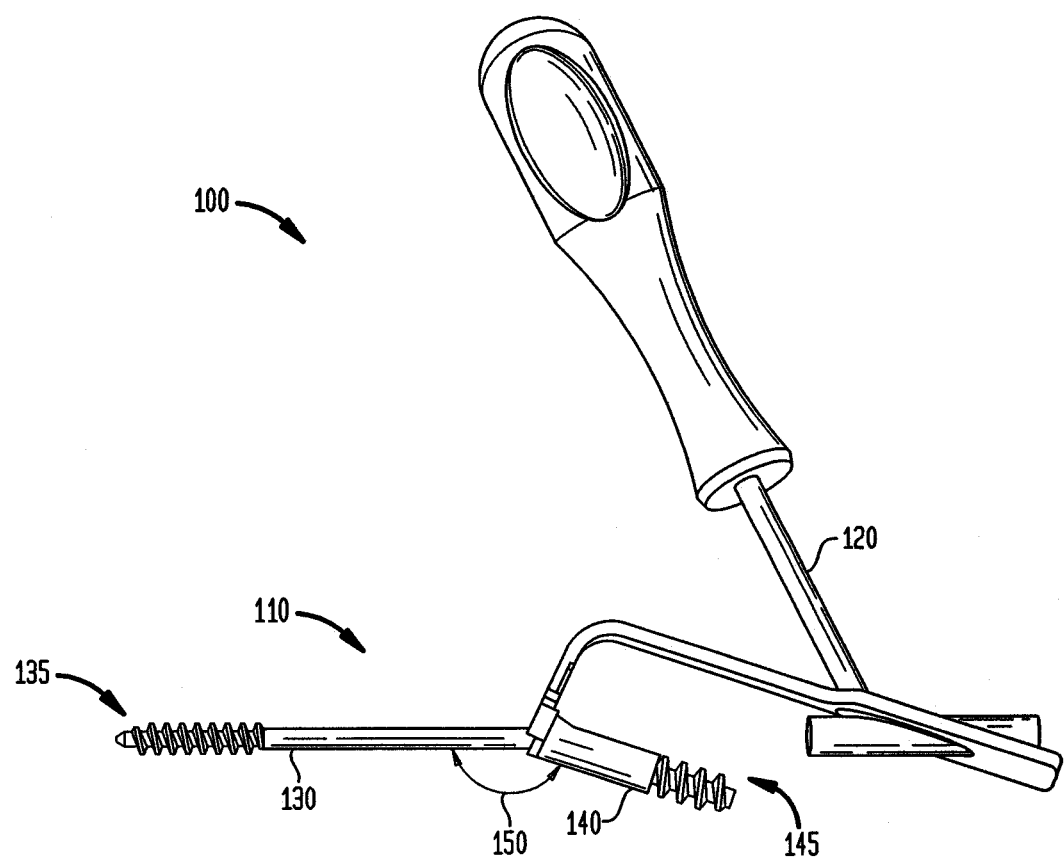
FIG. 1 is a perspective view of a fixation system according to a preferred embodiment of the invention.

The invention may be understood more readily by reference to the following detailed description of preferred embodiment of the invention. However, techniques, systems, and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise. Referring now to FIG. 1, there is shown a fixation system 100 which is made in accordance with the teachings of the preferred embodiment of the invention. As shown, the fixation system 100 includes an intramedullary fixation assembly 110, comprising a proximal screw member 130 and a distal member 140. Proximal screw member 130 is provided on proximal end 135 of assembly 110 and is coupled to a distal member 140 that is provided on the distal end 145 of the fixation assembly 110. Also, proximal screw member 130 makes a fixed angle 150 with distal member 140 and this angle 150 determines the angle for arch restoration. Moreover, fixation system 100 includes instrument 120 that is utilized to couple intramedullary fixation assembly 110 to the bones in the mid-foot region (not shown). It should be appreciated that in one non-limiting embodiment, intramedullary fixation assembly 110 may be made from a Titanium material, although, in other non-limiting embodiments, intramedullary fixation assembly 110 may be made from SST, PEEK, NiTi, Cobalt chrome or other similar types of materials.

As shown in FIG. 2, proximal screw member 130 is generally cylindrical in shape and extends from first bulbous portion 202 to second tapered end 204. End 204 has a diameter that is slightly smaller than diameter 226 of bulbous portion 202. Additionally, bulbous portion 202 has a taper, such as a Morse taper, with a width that decreases from end 211 to end 212. The taper allows for a locked interference fit with tapered aperture 316 when tapered bulbous portion 202 is combined with tapered aperture 316, shown and described below. Moreover, bulbous portion 202 is generally circular and has a generally hexagonal torque-transmitting aperture 208 that traverses length 210 of bulbous portion 202. However, a star-shaped aperture, a square-shaped aperture, or any other shaped aperture may be utilized without departing from the scope of the invention. Torque transmitting aperture 208 is utilized to transmit a torque from bulbous portion 202 to tapered end 204 by rotating bulbous portion 202.

Further, proximal screw member 130 has a first smooth exterior portion 206 extending from end 212 of bulbous portion 202. Portion 206 includes an internal aperture 214 that longitudinally traverses portion 206 in direction 201. Portion 206 terminates into a second generally tubular portion 216. Portion 216 may comprise internal circular aperture 220 that longitudinally traverses inside portion 216. Internal circular aperture 220 is aligned with apertures 214 and 208 along axis 203 to form a continuous opening (i.e., a cannula) from bulbous portion 202 to end 204. The continuous opening or cannula is provided to interact with a guide wire (not shown) by receiving the guide wire within the continuous opening thereby positioning and locating the proximal member 130. In other non-limiting embodiments, the proximal member 130 may be provided without apertures 220 and 214 (i.e., the proximal member is solid).

Furthermore, tubular portion 216 has a plurality of circular threads, such as threads 218, which are circumferentially disposed on the external surface of portion 216 and, with threads 218 having an external diameter 224. Portion 216 may also be provided with a self-tapping leading edge 222 to provide portion 216 with the ability to remove bone material during insertion of proximal screw member 130 into bone. It should be appreciated that the length of the proximal member 130 may be selected of varying lengths to allow a surgeon to fuse different joints in a foot (not shown).

Figure 3A:
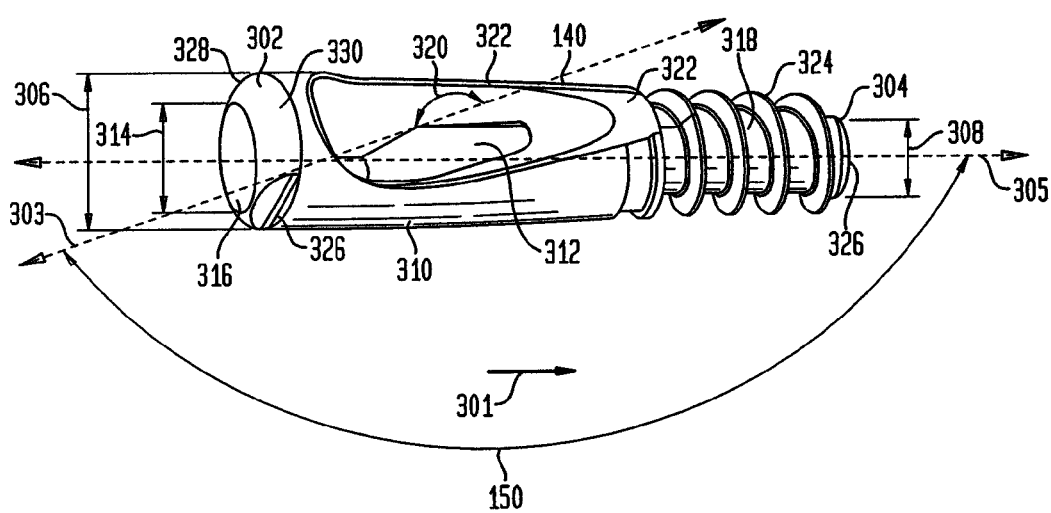
FIG. 3A is a perspective view of a distal member used in the fixation system shown in FIG. 1 according to the preferred embodiment of the invention.
Figure 3B:
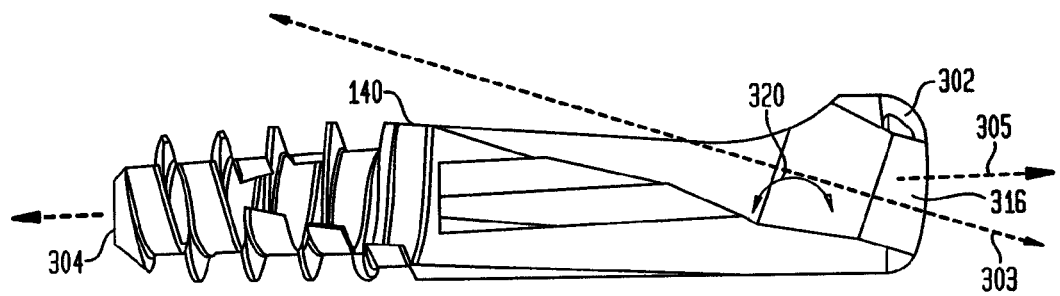
FIG. 3B is a perspective cross-sectional view of the distal member shown in FIG. 3A according to the preferred embodiment of the invention.

As shown in FIGS. 3A-3B, distal member 140 of the preferred embodiment is generally tubular in shape and tapers from a first end 302 to a second end 304 (i.e. end 302 has a diameter 306 that is slightly larger than diameter 308 of end 304). However, in another non-limiting embodiment, distal member 140 has a constant width from first end 302 to second end 304. Further, first end 302 is generally semi-spherical in shape and has an internal circular aperture 316, which traverses end 302 along direction 301 (i.e. end 302 is generally "donut" shaped). Additionally, circular aperture 316 emanates from surface 322, such that portion 310 has a generally tapered aperture 316 provided in portion 310. Circular aperture 316 includes slope 320 from first end 302 to end 322 of portion 310. Further, aperture 316 is aligned along axis 303, which is offset from horizontal axis 305 of distal member 140. Axis 303 forms an angle 150 with horizontal axis 305 that determines the angle for arch restoration, as shown in FIG. 3A. Angle 150 may be any angle greater than 90 degrees and less than 180 degrees. Tapered aperture 316 when combined with tapered bulbous portion 202, shown in FIG. 2, creates a locked interference fit between proximal member 130 and distal member 140. First end 302 has a plurality of substantially similar grooves 326 and 328, which form an "L-shape" with surface 330 of end 302. Grooves 326 and 328 are provided to receive instrument 120 of fixation system 100, which is later described. In other non-limiting embodiments, other similar instruments may be provided to be received within grooves 326 and 328.

Distal member 140 further includes a generally smooth portion 310 coupled to end 302. Portion 310 has a generally hexagonal shaped aperture 312, which opens into aperture 316 and which longitudinally traverses through portion 310 in direction 301. In other non-limiting embodiments, a star-shaped aperture, a square-shaped aperture, or any other shaped aperture may be utilized. Circular aperture 316 has a diameter 314 that is slightly larger than external diameter 224 of portion 216 and 206 of proximal screw member 130, with portions 216 and 206 being slidably received within aperture 316 of portion 310. Aperture 316 has a diameter that is smaller than diameter 226 of bulbous portion 202.

Portion 310 of distal member 140 terminates into a second generally cylindrical portion 318 which has a plurality of threads 324, which are circumferentially disposed on the external surface of portion 318. Portion 318 has an internal circular aperture 326 which is longitudinally coextensive with portion 318 in direction 301. Circular aperture 326 aligns with aperture 312 to form a continuous opening from end 302 to end 304.

Figure 4:
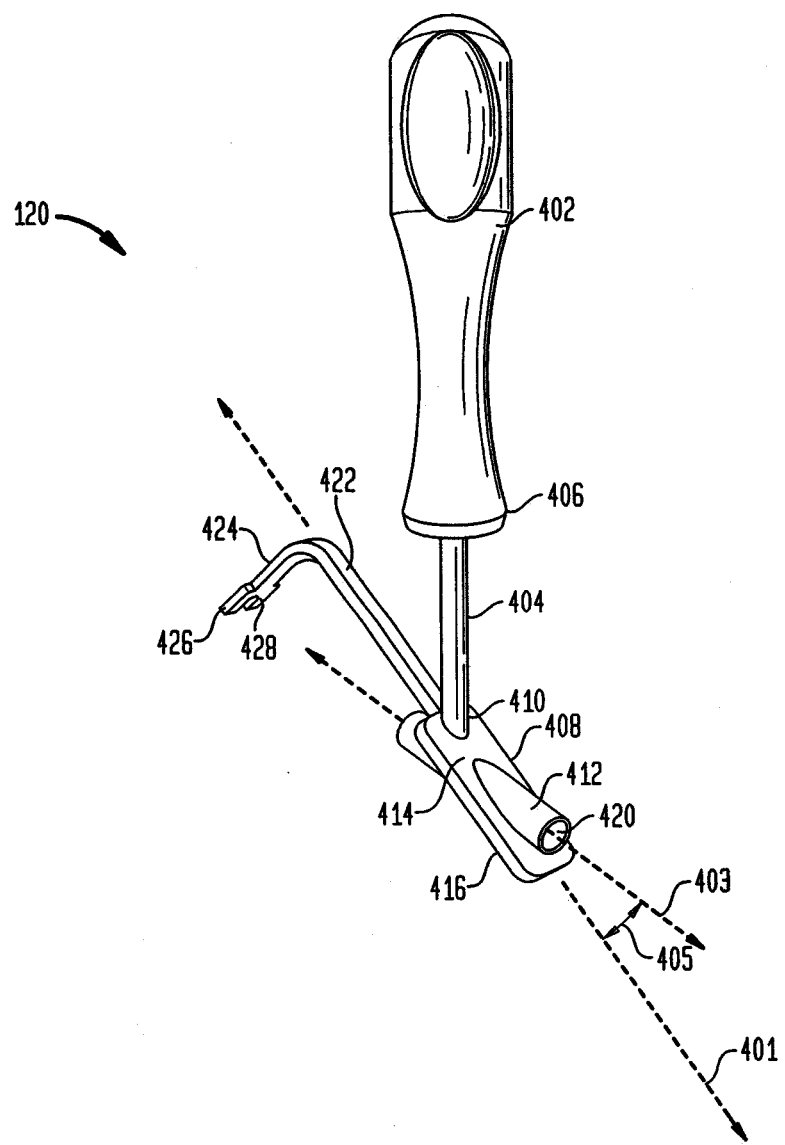
FIG. 4 is a perspective view of the instrument member used in the fixation system shown in FIG. 1 according to the preferred embodiment of the invention.

As shown in FIG. 4, instrument 120 is illustrated for coupling proximal screw member 130 to distal member 140. Particularly, instrument 120 includes a handle portion 402 coupled to a rod portion 404. Rod portion 404 emanates from handle portion 402 at end 406 and terminates into a rectangular planar portion 408 at end 410. Planar portion 408 is aligned along axis 401 and is fixably coupled to a generally cylindrical tubular portion 412 (i.e., an aiming device).

Portion 412 traverses portion 408 from top surface 414 to bottom surface 416. Further, tubular portion 412 is aligned along dissimilar axis 403, forming an angle 405 with axis 401. Also, tubular portion 412 has a through aperture 420 that longitudinally traverses portion 412 along axis 403.

Planar portion 408 is coupled to planar portion 422, with portion 422 having a width slightly smaller than width of portion 408. Portion 422 terminates into a generally "U-shaped" portion 424 with portion 424 being orthogonal to portion 422. Further, portion 424 has a plurality of substantially similar sides 426 and 428 which are provided to be slidably coupled to grooves 326 and 328 of distal member 140.

Figure 5:
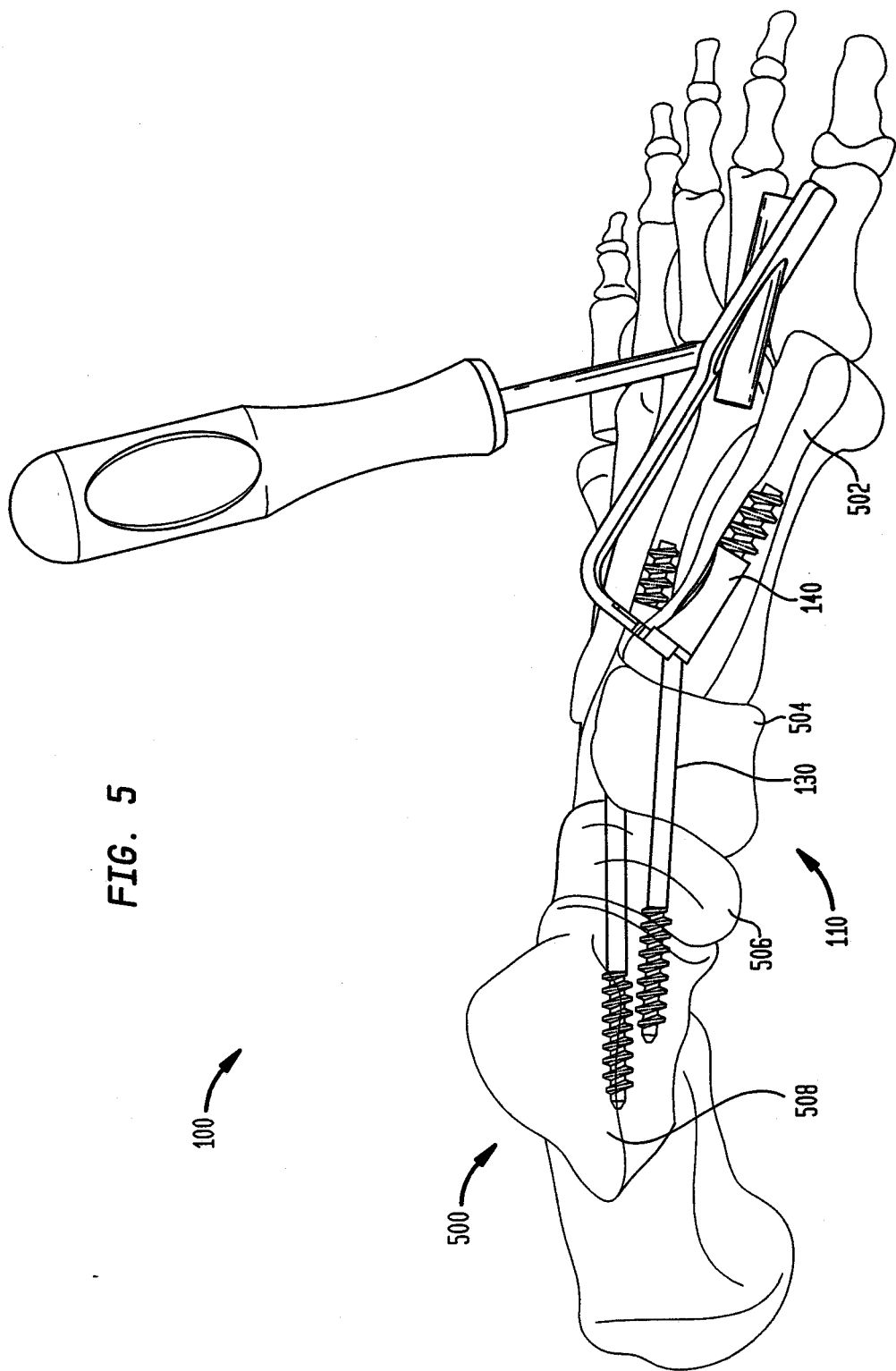
FIG. 5 is a perspective view of the assembled intramedullary fixation assembly inserted into the bones of a patient's foot according to the preferred embodiment of the invention.
Figure 6:
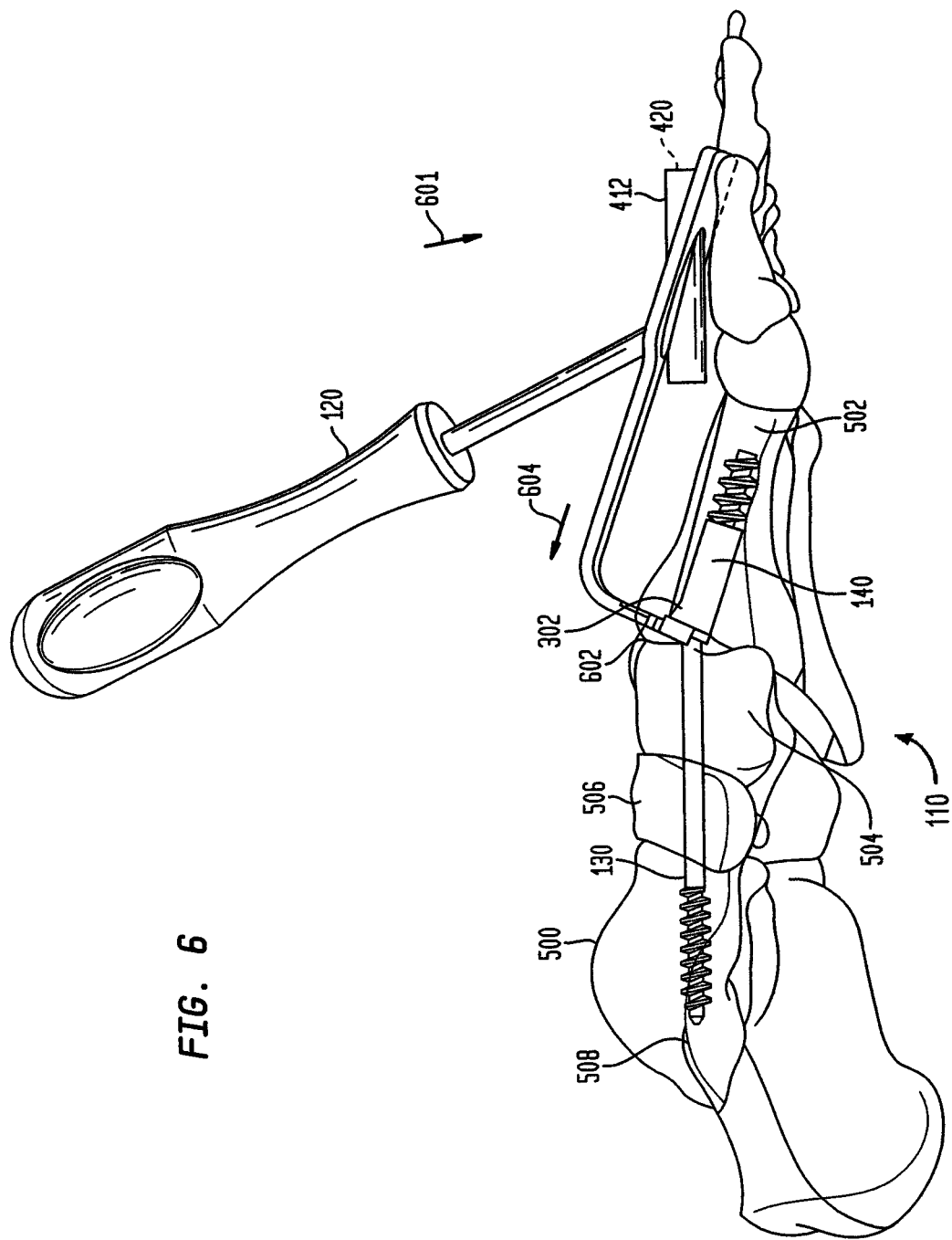
FIG. 6 is a side view of the assembled intramedullary fixation assembly shown in FIG. 5 according to the preferred embodiment of the invention.
Figure 7:
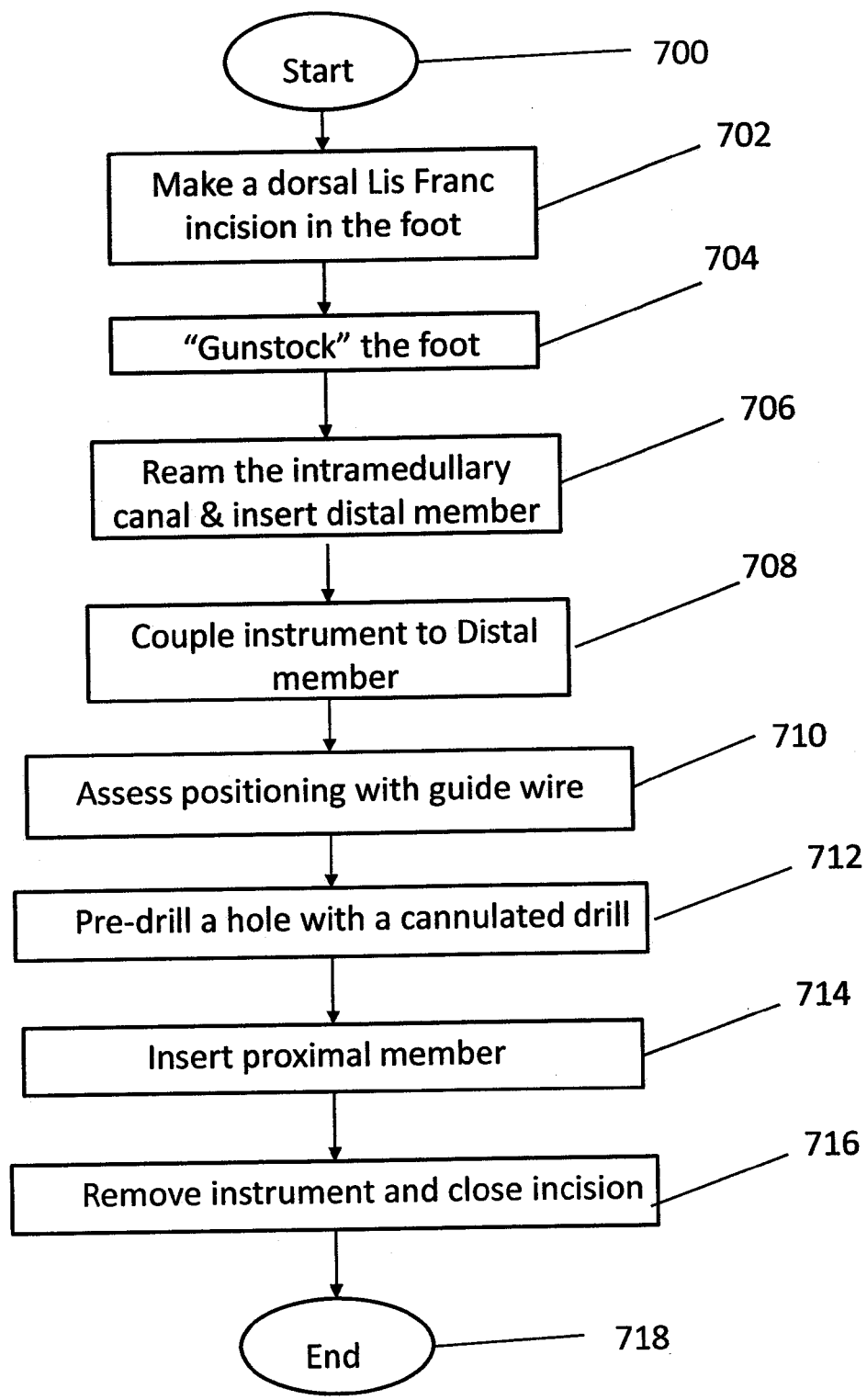
FIG. 7 is a flow chart illustrating the method of coupling the intramedullary fixation assembly shown in FIGS. 1-6 to tarsal and metatarsal bones in a patient's foot according to the preferred embodiment of the invention.

In operation, sides 426 and 428 of instrument 120 are received in respective grooves 326 and 328 of distal member 140, of FIGS. 3A-3B, thereby slidably coupling distal member 140 to instrument 120. In this position, axis 303 of aperture 316 is aligned along substantially the same axis as axis 403 of instrument 120. Proximal screw member 130 is coupled to distal member 140 by slidably coupling portions 206 and 216 through aperture 420 of tubular portion 412. Tubular portion 412 guides proximal screw member 130 through internal aperture 420 and into aperture 316 on surface 322 and may also guide a Kirschner wire (K wire) or a drill. Proximal screw member 130, of FIG. 2, travels into bone as portions 216 and 206 travel further through aperture 316 at end 302 until bulbous portion 202 is restrained by surface 322 and end 302. Aperture 316, being tapered along axis 303, causes proximal screw member 130 to form an angle 150 with distal member 140, with proximal member 130 being aligned along an axis 303, which is substantially the same axis as axis 403 of tubular portion 412 of instrument 120. In operation, and as best shown in FIGS. 5, 6 and 7, the fixation system 100 utilizes the intramedullary fixation assembly 110 for treating and fixating the deteriorated and damaged or fractured bones in the human foot 500. This restores the arch in a human foot 500 by coupling the intramedullary fixation assembly 110 to the human foot 500 of a left leg. In one-non limiting example, and as shown in FIG. 5, the intramedullary assembly 110 is coupled to the medullary canals of the first metatarsal 502, medial cuneiform 504, navicular 506 and talus bone 508. Talus bone 508 makes up part of the ankle joint where the threaded portion 216 of the proximal screw member 130 of the intramedullary assembly 110 is threadably coupled. The medial cuneiform 504 and navicular 506 bones are most affected by Diabetic Charcot foot disorder that causes deterioration and collapse of the arch of the foot 500. It should be appreciated that the intramedullary assembly 110 may be used within each of the five rays, with a ray representing a line drawn from each metatarsal bone to the talus. The angulation in the smaller rays will be smaller than the two rays (i.e., a line from the first and second metatarsal bones to the talus bone). Also, the diameter of distal member 140 will decrease from the large ray to the small ray.

In one non-limiting example, the angulation may be any angle greater than 90 degrees and less than 180 degrees. For example, the angle for the first ray may be 150-170 degrees and the angles for the other rays may be 160-175 degrees.

As shown in FIGS. 6 and 7, the intramedullary fixation assembly 110 may be utilized to reconstruct an arch in a mid-foot region of a human foot 500. As shown, the method starts in step 700 and proceeds to step 702, whereby a Dorsal Lis Franc incision (i.e., mid-foot incision) (not shown) is made in foot 500 in order to gain access to the joint. In step 704, the joint capsule is separated by "Gunstocking" foot 500 in direction 601 (i.e., the foot 500 is bent mid-foot) to expose the articular surface 602 and the articulating cartilage is removed. Next, in step 706, the intramedullary canal is reamed and the distal member 140 is inserted into the intramedullary canal (not shown) of the metatarsal 502. In other non-limiting embodiments, the distal member 140 may be inserted by impaction, by press fit, by reaming a hole in the intramedullary canal (not shown) or substantially any other similar strategy or technique.

Next, in step 708, the instrument 120 is coupled to the distal member 140 by coupling sides 426 and 428 of instrument 120 to respective grooves 326 and 328. In step 710, initial positioning of the proximal member 130 is assessed with the use of a guide wire through portion 412 (i.e., aiming device). Next, in step 712, a countersink drill is inserted through portion 412 and the proximal cortex is penetrated. In this step, a cannulated drill or guide wire is used to pre-drill the hole through the joints selected for fusion. In step 714, the proximal screw member 130 is inserted over the guide wire and into the distal member 140. Particularly, the proximal member 130 is inserted through tubular portion 412 (i.e., aiming device), causing proximal member 130 to travel through internal longitudinal aperture 420, into distal member 140 and further into bones 504, 506 and 508 until rigid connection with the tapered aperture 316 is made, thereby compressing the joint. In one non-limiting embodiment, a locking element (not shown) such as a plate or a washer is coupled to end 302 of the intramedullary fixation assembly 110 to further secure proximal threaded member 130 to distal member 140. Next, in step 716 the instrument 120 is removed and the dorsal Lis Franc (i.e., mid-foot) incision is closed. The method ends in step 718.

It should be appreciated that a plurality of intramedullary fixation assemblies, such as intramedullary fixation assembly 110, may be inserted into any of the bones of a foot 500 such as, but not limited to the metatarsal, cuneiform, calcaneus, cuboid, talus and navicular bones, in order to restore the natural anatomical shape of the arch of the foot 500. Thus, the fixation system 100, in one non-limiting embodiment, is utilized to couple the intramedullary fixation assembly 110 to the foot 500, which causes the metatarsal 504, medial cuneiform 504, navicular 506 and talus 508 bones to be aligned to the proper anatomical shape of an arch when assembled within foot 500. It should be appreciated that the intramedullary fixation assembly 110 is delivered through a dorsal midfoot incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 110 may be utilized with graft material (i.e., autograft, allograft or other biologic agent).

Figure 8:
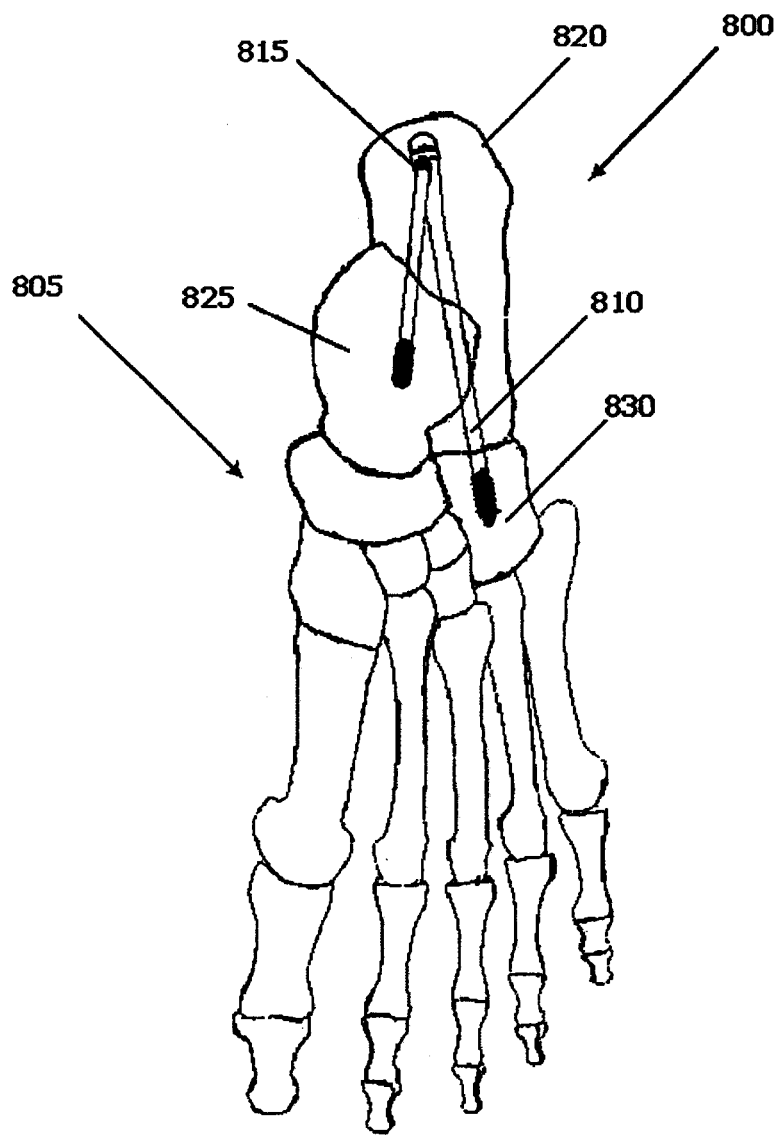
FIG. 8 is a perspective view of an assembled intramedullary fixation assembly inserted into the bones of a patient's foot according to an alternate embodiment of the invention.

In an alternate embodiment, as shown in FIG. 8, an intramedullary fixation assembly 800 is provided in order to apply intraosseous compression to bones. Particularly, the intramedullary fixation assembly 800 includes a tapered screw member 810 coupled to a lag screw member 815 at a fixed acute angle for the internal fusion of the bones of the human foot 805, such as, for example, the calcaneus bone 820, the talus bone 825, and the cuboid bone 830. In other non-limiting embodiments, the intramedullary fixation assembly 800 may be utilized for any other appropriate use for the internal fixation of the other bones. It should be appreciated that the intramedullary fixation assembly 800 may be provided at several lengths for the internal fixation of a variety of bone sizes in the human body.

Figure 9:
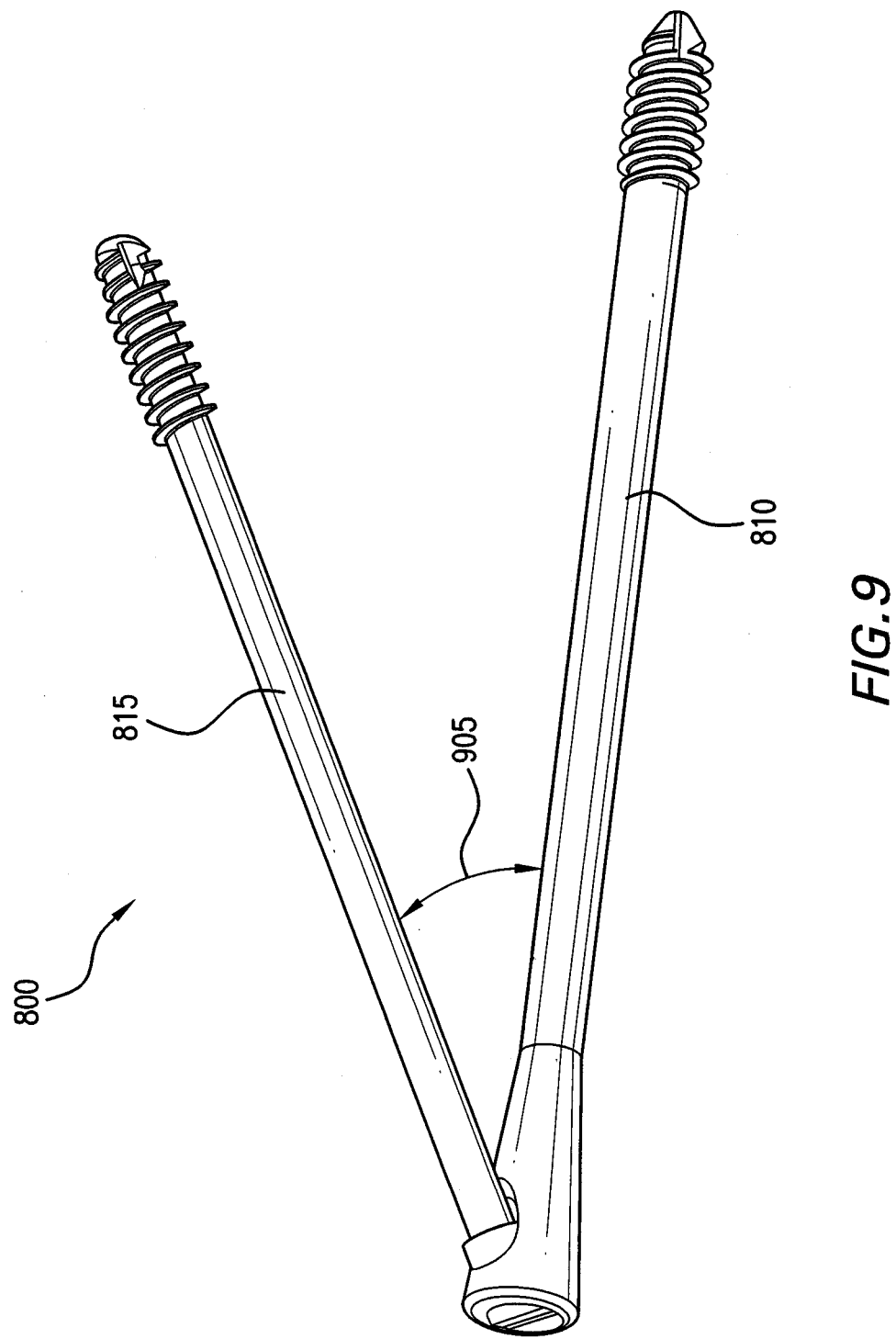
FIG. 9 is a perspective view of the intramedullary fixation assembly shown in FIG. 8 according to the alternate embodiment of the invention.

Also as shown in FIG. 9, the intramedullary fixation assembly 800 includes the tapered screw member 810 coupled to the lag screw member 815 at a fixed angle 905. The fixed angle 905 may be provided at various fixed angles depending on the bone segments that are being compressed. The fixed angle between the tapered screw member 810 and the lag screw member 815 causes the intramedullary fixation assembly 800 to "hook" into the bone segments and translates the compression applied to bone fragments across the members 810 and 815. It should be appreciated that in one non-limiting embodiment, the intramedullary fixation assembly 800 may be made from a Titanium material, although, in other non-limiting embodiments, the intramedullary fixation assembly 800 may be made from SST, PEEK, NiTi, Cobalt chrome or other similar types of materials. It should also be appreciated that the intramedullary fixation assembly 800 is locked at the fixed angle after insertion of the same into bone. The intramedullary fixation assembly 800 translates compression applied to bone fragments by the tapered screw member 810 and the lag screw member 815 into uniform compression through multi-point fixation.

Figure 10:
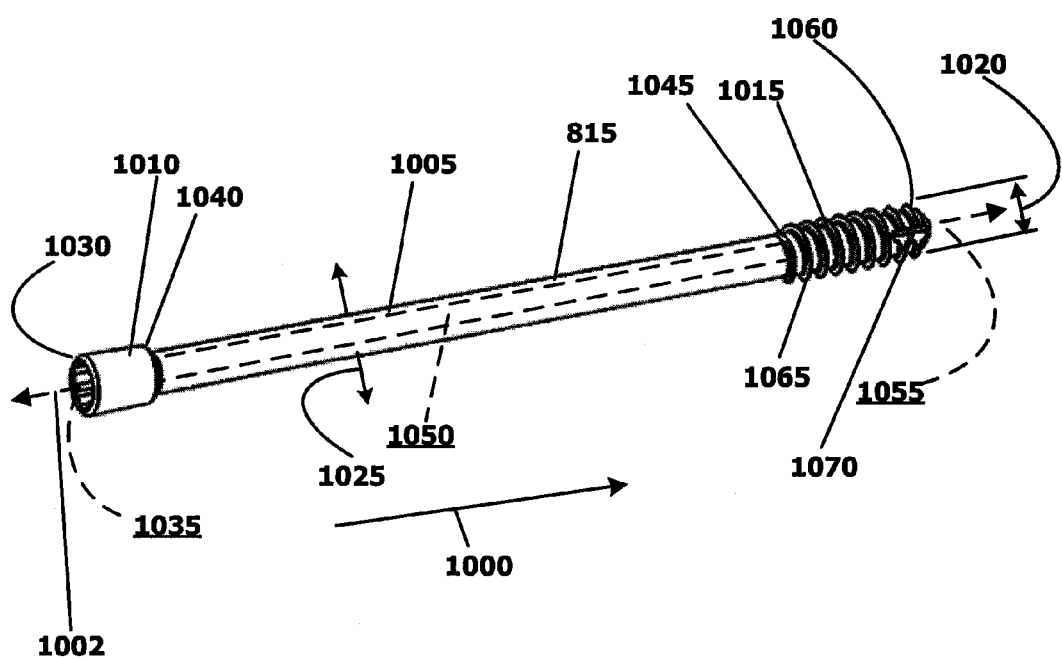
FIG. 10 is a perspective view of the lag screw member used in the intramedullary fixation assembly shown in FIGS. 8-9 according to the alternate embodiment of the invention.

As shown in FIG. 10, lag screw member 815 is generally cylindrical in shape and has a first smooth exterior portion 1005 that extends from first bulbous portion 1010 to a second threaded portion 1015. Additionally, bulbous portion 1010 has a taper, such as a Morse taper, with a width that decreases from end 1030 in direction 1000. The Morse taper allows for a locked interference fit with tapered aperture 1130 (shown in FIG. 11) when tapered bulbous portion 1010 resides within tapered aperture 1130, which will be shown and described below. Moreover, tapered bulbous portion 1010 is generally cylindrical in shape and has a generally hexagonal-shaped aperture 1035 aligned along axis 1002 traversing the longitudinal length of bulbous portion 1010. However, a star-shaped aperture, a square-shaped aperture, or any other shaped aperture may be utilized without departing from the scope of the invention. Aperture 1035 is provided to transmit torque from bulbous portion 1010 to threaded portion 1015 as bulbous portion 1010 is rotated in a direction that causes a corresponding rotation of threaded portion 1015. Further, lag screw member 815 has a first smooth exterior portion 1005 that has a uniform diameter 1025 from first end 1040 to second end 1045. Portion 1005 includes an internal aperture 1050 aligned along axis 1002 that traverses the longitudinal length of portion 1005 in direction 1000. Further, portion 1005 terminates into a threaded portion 1015. Threaded portion 1015 includes an internal aperture 1055 aligned along axis 1002 that longitudinally traverses threaded portion 1015. Internal aperture 1055 being aligned on the same axis 1002 as apertures 1035 and 1055 cooperatively form a continuous opening (i.e., a cannula) from end 1030 of bulbous portion 1010 to end 1060 of threaded portion 1015. The continuous opening or cannula is provided to interact with a guide wire (not shown) by receiving the guide wire within the continuous opening to help guide and position the lag screw member 815 during insertion of the lag screw member 815. In other non-limiting embodiments, the lag screw member 815 may be provided without apertures 1050 and 1055 (i.e., the lag screw member 815 is solid).

Furthermore, threaded portion 1015 has a plurality of circular threads, such as threads 1065, which are circumferentially disposed on the external surface of threaded portion 1015. Threaded portion 1015 has a diameter 1020 that is substantially the same as diameter 1025 of portion 1005. Threaded portion 1015 may also be provided with a self-tapping leading edge 1070 to provide portion 1015 with the ability to remove bone material during insertion of lag screw member 815 into bone. It should be appreciated that the length of the lag screw member 815 may be selected of varying lengths to allow a surgeon to fuse different joints in the human body. It should be appreciated that the lag screw member 815 may be positioned at one angle inside the tapered screw member 810. Also, lag screw member 815 may be coated with an osteoconductive material, such as, for example, plasma spray or other similar types of porous materials that is capable of supporting or encouraging bone ingrowth into this material.

Figure 11:
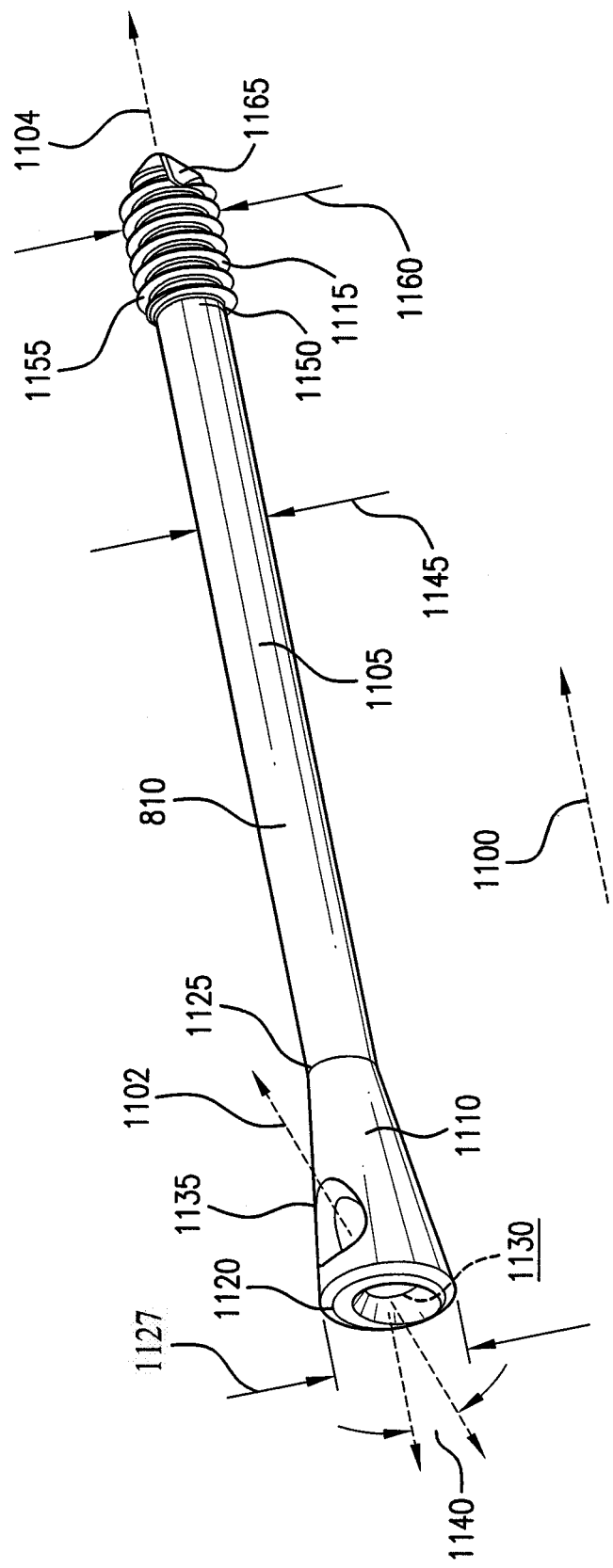
FIG. 11 is a perspective view of the tapered screw member used in the intramedullary fixation assembly shown in FIGS. 8-9 according to the alternate embodiment of the invention.

As shown in FIG. 11, tapered screw member 810 is generally cylindrical in shape and has a smooth exterior portion 1105 that extends from a tapered portion 1110 to a threaded portion 1115. Tapered screw member 810 is aligned along longitudinal axis 1104, which is longitudinally coextensive with length of tapered screw member 810.

Further, tapered portion 1110 is generally tubular in shape and tapers from end 1120 to end 1125 (i.e. end 1120 has a diameter 1127 that decreases slightly in diameter from end 1120 in direction 1100). Further, first end 1120 has a tapered aperture 1130, which traverses tapered portion 1110 along axis 1102, which causes tapered aperture 1130 to emanate from surface 1135. Axis 1102 is offset from longitudinal axis 1104 at an angle 1140. Moreover, tapered portion 1110 has a generally hexagonal-shaped aperture contained within portion 1110, which is aligned along axis 1104 and is provided to receive an instrument (not shown) for applying torque to tapered screw member 810. In other non-limiting embodiments, a star-shaped aperture, a square-shaped aperture, or any other shaped aperture may be utilized without departing from the scope of the invention. With tapered aperture 1130 being aligned along axis 1102, tapered aperture 1130 forms a fixed angle 1140 with longitudinal axis 1145. Fixed angle 1140 determines the angle for fixation of tapered screw member 810 with respect to lag screw member 815 (shown in FIG. 10). It should be appreciated that fixed angle 1140 may be any angle less than 90 degrees to allow a surgeon the flexibility of determining the angle for internal fixation of bones in the human body. It should also be appreciated that tapered aperture 1130 when combined with tapered bulbous portion 1010, shown in FIG. 10, creates a locked interference fit between tapered screw member 810 and lag screw member 815.

Further, tapered screw member 810 has a smooth exterior portion 1105 that has a uniform diameter 1145 from end 1125 to end 1150. Tapered screw member 810 is generally solid, however, in other non-limiting embodiments, screw member 810 may be cannulated. Further, portion 1105 terminates into a threaded portion 1115. Threaded portion 1115 is generally solid and includes a plurality of circular threads, such as threads 1155, which are circumferentially disposed on the external surface of threaded portion 1115. Threaded portion 1115 has a diameter 1160 that is substantially the same as diameter 1145 of portion 1105. Threaded portion 1115 may also be provided with a self-tapping leading edge 1165 to provide portion 1115 with the ability to remove bone material during insertion of tapered screw member 810 into bone. It should be appreciated that the length of the tapered screw member 810 may be selected of varying lengths to allow a surgeon to fuse different joints in the human body. It should be appreciated that tapered screw member 810 may be coated with an osteoconductive material, such as, for example, plasma spray or other similar types of porous materials that is capable of supporting or encouraging bone ingrowth into this material.

Figure 12:
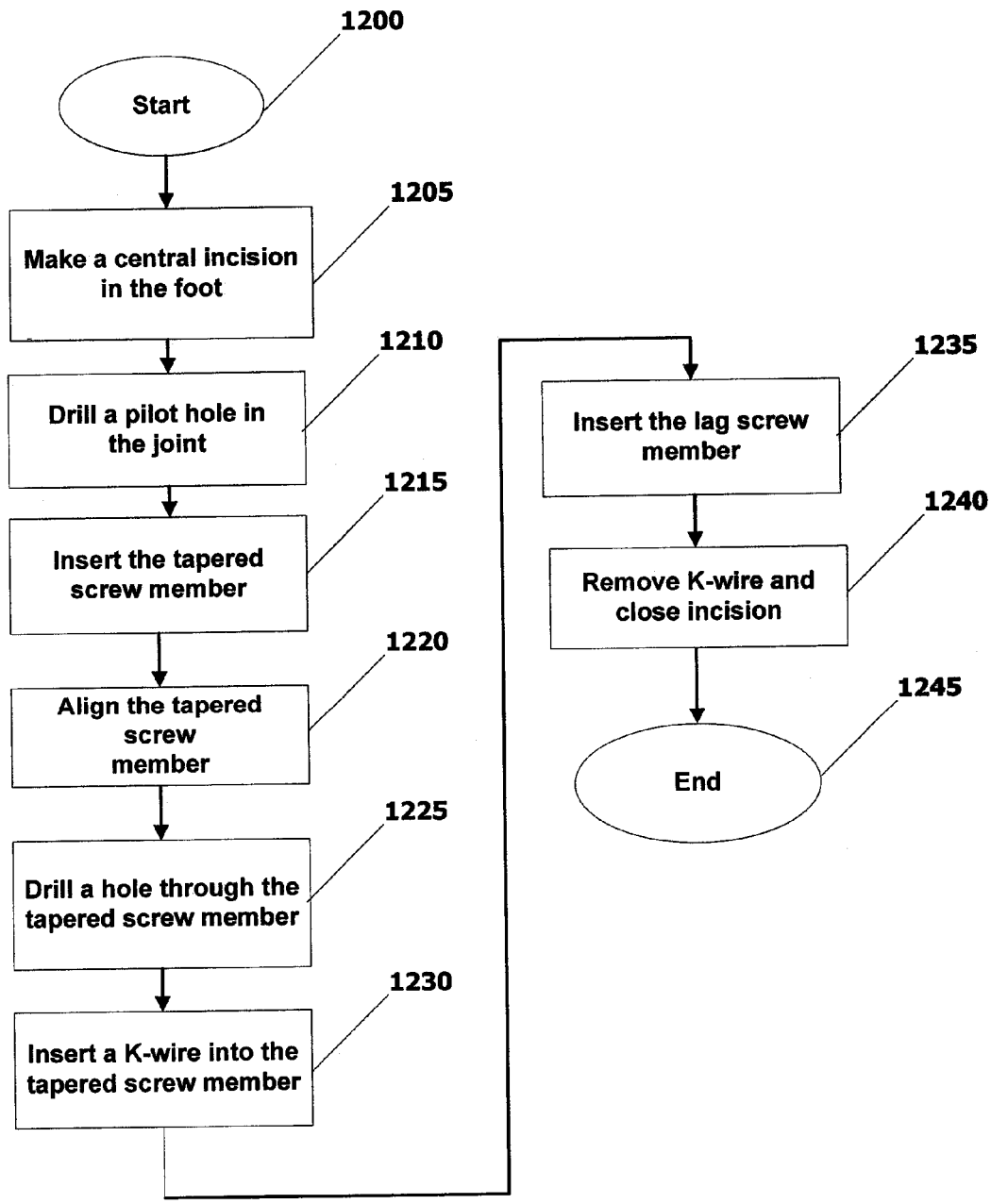
FIG. 12 is a flow chart illustrating the method of coupling the intramedullary fixation assembly shown in FIG. 8-9 to bones in a patient's foot according to the alternate embodiment of the invention.

As shown in FIGS. 8 and 12, the intramedullary fixation assembly 800 may be utilized to apply compression, for example to the bones in a human foot through an acute angle fixation of the tapered screw member 810 to the lag screw member 815. As shown, the method starts in step 1200 and proceeds to step 1205, whereby a central incision is made in the hind-foot region of foot 805. Next, in step 1210, a pilot hole is drilled into the calcaneus 820 and the cuboid 830 bones. In this step, a countersink drill is inserted a cannulated drill or guide wire is used to pre-drill the hole through the joints selected for fusion. Next, in step 1215, tapered screw member 810 is inserted into the intraosseous intramedullary canal (not shown) of the calcaneus 820. In other non-limiting embodiments, the tapered screw member 810 may be inserted by impaction, by press fit, by reaming a hole in the intramedullary canal (not shown) or substantially any other similar strategy or technique.

Next, in step 1220, the final position of the tapered screw member 810 is aligned so that the coupling of the lag screw member 815 forms a predetermined angle with the tapered screw member 810. In step 1225, align a guide through tapered aperture 1130 at surface 1135 and pre-drill a hole through the joint substantially along axis 1102. Next, in step 1230, insert a K-wire (not shown) into the pre-drilled hole and into the tapered screw member 810 so that the K-wire makes an acute angle with the tapered screw member 810. Next, in step 1235, the lag screw member 815 is rotated and inserted over the K-wire and into the calcaneus bone 820 so that the K-wire guides the lag screw member 815. The K-wire, in assisting the lag screw member 815, penetrates end 1060 and emanates from end 1030. In some non-limiting embodiments, the lag member 815 may be inserted by impaction, by press fit, or substantially any other similar strategy or technique. Next, in step 1240, the K-wire is removed and the incision is closed. The method ends in step 1245.

Figure 13:
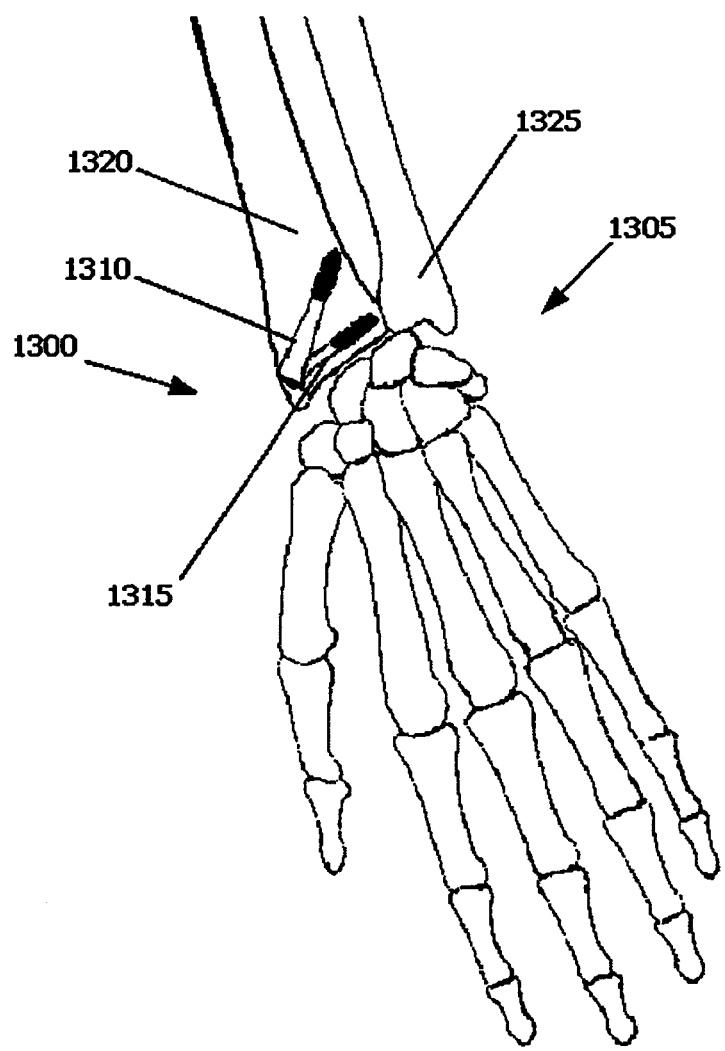
FIG. 13 is a perspective view of an assembled intramedullary fixation assembly inserted into the bones of a patient's hand according to an alternate embodiment of the invention.

In an alternate embodiment, as shown in FIG. 13, an intramedullary fixation assembly 1300 is provided for the internal fixation of bones in a human hand 1305. Particularly, the intramedullary fixation assembly 1300 is substantially the same as the intramedullary fixation assembly 800 of the embodiment shown and described in FIG. 8. The intramedullary fixation assembly 1300 includes a tapered screw member 1310 forming a fixed acute angle with the lag screw member 1315. The fixed acute angle is predetermined and the angle may be selected up to 90 degrees by, in one example, a surgeon to provide for the internal fixation of the bones in the human hand 1305, such as for example the radius 1320 and ulna 1325.

Figure 14:
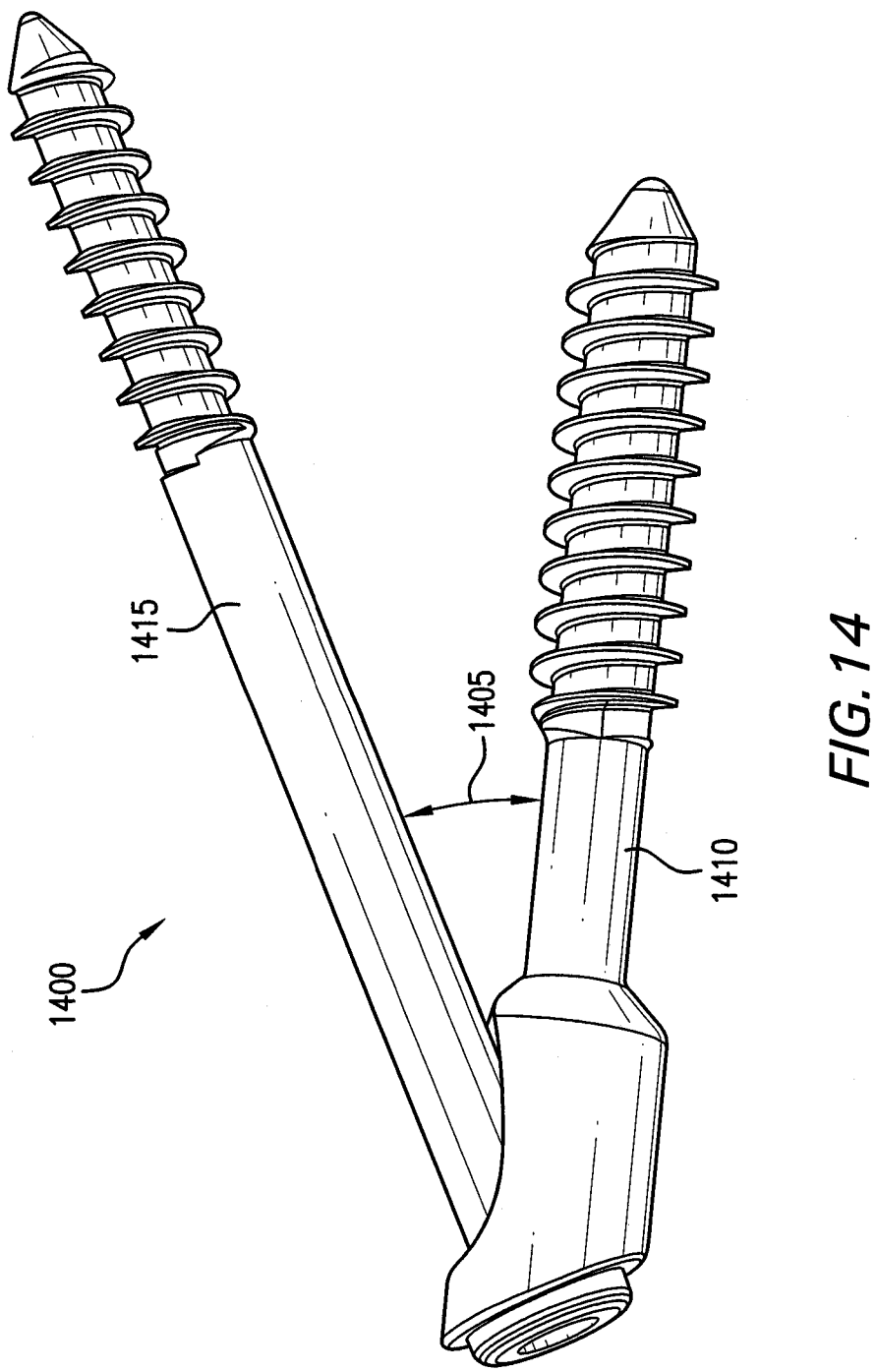
FIG. 14 is a perspective view of the intramedullary fixation assembly shown in FIG. 13 according to the alternate embodiment of the invention.

In another alternate embodiment, as shown in FIG. 14, an intramedullary fixation assembly 1400 may be provided to vary the acute angle between 0 and 90 degrees after insertion of the intramedullary fixation assembly 1400. Particularly, the intramedullary fixation assembly 1400 includes a polyaxial screw member 1410 coupled to a lag screw member 1415 and forming an angle 1405 between the two members 1410 and 1415. The angle 1405 between the polyaxial screw member 1410 and the lag screw member 1415 causes the intramedullary fixation assembly 1400 to "hook" into the bone segments and translates the compression applied to bone fragments across the members 1410 and 1415. It should be appreciated that the intramedullary fixation assembly 1400 may be provided at several lengths for the internal fixation of a variety of bone sizes in the human body. It should also be appreciated that in one non-limiting embodiment, the intramedullary fixation assembly 1400 may be made from a Titanium material, although, in other non-limiting embodiments, the intramedullary fixation assembly 1400 may be made from SST, PEEK, NiTi, Cobalt chrome or other similar types of materials.

Figure 15:
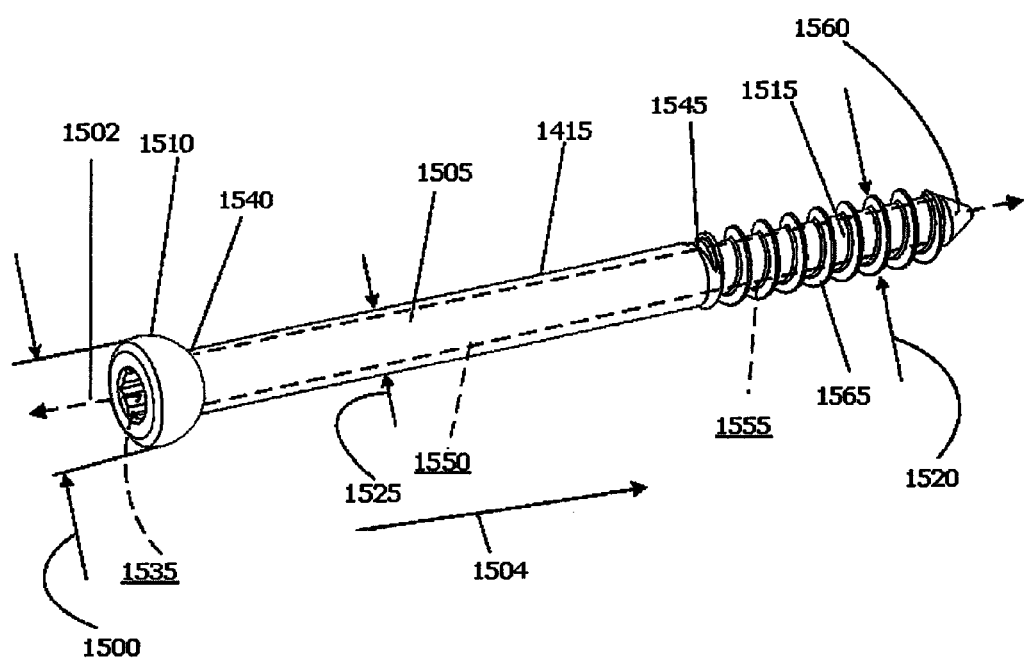
FIG. 15 is a perspective view of the lag screw member used in the intramedullary fixation assembly shown in FIG. 14 according to the alternate embodiment of the invention.

As shown in FIG. 15, lag screw member 1415 is generally cylindrical in shape and has a first smooth exterior portion 1505 that extends from first bulbous portion 1510 to a second threaded portion 1515. Bulbous portion 1510 is generally semispherical in shape and has a diameter 1500 that is slightly larger than the internal diameter of aperture 1630 (shown in FIG. 16), which is provided to receive bulbous portion 1510. The bulbous portion 1510 resides within the internal aperture 1630 (shown in FIG. 16) and provides for rotational movement of both the polyaxial screw member 1410 and the lag screw member 1415 at various angles between 0 and 90 degrees after insertion of the intramedullary fixation assembly 1400. Also, bulbous portion 1510 has a generally hexagonal-shaped aperture 1535 aligned along axis 1502 traversing the longitudinal length of bulbous portion 1510. In other non-limiting embodiments, a star-shaped aperture, a square-shaped aperture, or any other shaped aperture may be utilized without departing from the scope of the invention. Aperture 1535 is provided to transmit torque from bulbous portion 1510 to threaded portion 1515 as bulbous portion 1510 is rotated in a direction that causes a corresponding rotation of threaded portion 1515. It should also be appreciated that axis 1502 is longitudinally coextensive with the length of lag screw member 1415.

Further, lag screw member 1415 has a first smooth exterior portion 1505 of a uniform diameter 1525 from first end 1540 to second end 1545. Portion 1505 includes an internal aperture 1550 aligned along axis 1502 that traverses the longitudinal length of portion 1505 along direction 1504. Further, portion 1505 terminates into the threaded portion 1515. Threaded portion 1515 also includes an internal aperture 1555 aligned along axis 1502 that longitudinally traverses threaded portion 1515. Internal aperture 1555 being aligned along the same axis 1502 as apertures 1535 and 1555 cooperatively form a continuous opening (i.e., a cannula) from bulbous portion 1510 to end 1560 of threaded portion 1515. The continuous opening or cannula is provided to interact with a guide wire (not shown) by receiving the guide wire within the continuous opening to help guide and position the lag screw member 1415 during insertion into bone. In other non-limiting embodiments, the lag screw member 1415 may be provided without apertures 1550 and 1555 (i.e., the lag screw member 1415 is non-cannulated or solid).

Furthermore, threaded portion 1515 has a plurality of circular threads, such as threads 1565, which are circumferentially disposed on the external surface of threaded portion 1515. Threaded portion 1515 has a diameter 1520 that is substantially the same as diameter 1525 of portion 1505. Threaded portion 1515 may also be provided with a self-tapping leading edge (not shown) to provide portion 1515 with the ability to remove bone material during insertion of lag screw member 1415 into bone. It should be appreciated that the length of the lag screw member 1415 may be selected of varying lengths to allow a surgeon to fuse different joints in the human body. Also, lag screw member 1415 may be coated with an osteoconductive material, such as, for example, plasma spray or other similar types of porous materials that is capable of supporting or encouraging bone ingrowth into this material.

Figure 16:
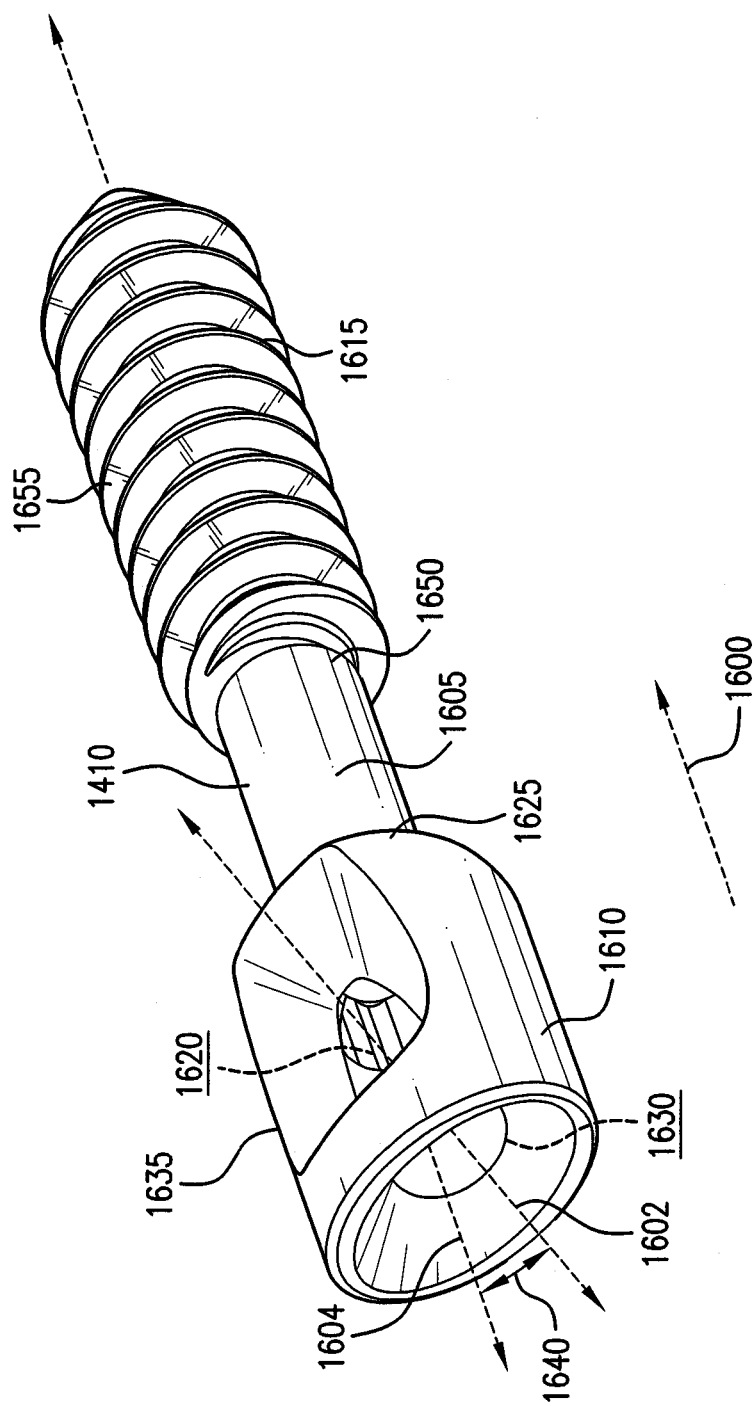
FIG. 16 is a perspective view of the polyaxial screw member used in the intramedullary fixation assembly shown in FIG. 14 according to the alternate embodiment of the invention.

As shown in FIG. 16, polyaxial screw member 1410 is generally cylindrical in shape and has a smooth exterior portion 1605 that extends from portion 1610 to a threaded portion 1615. Polyaxial screw member 1410 is aligned along longitudinal axis 1604, which is longitudinally coextensive with length of polyaxial screw member 1410.

Further, portion 1610 is generally tubular in shape having a uniform diameter, which is slightly larger than diameter of aperture 1630 causing portion 1610 to abut the interior surface of portion 1610 at aperture 1630. However, in other non-limiting embodiments, portion 1610 may be tapered going from a larger diameter to a smaller diameter as we traverse portion 1610 along direction of axis 1600. Further, portion 1610 has a plurality of apertures 1620 and 1630 of dissimilar diameters. Aperture 1630 is a through aperture and is tapered along axis 1602, causing aperture 1630 to emanate from surface 1635. On the other hand, aperture 1620 is longitudinally disposed along axis 1604 and has a generally hexagonal shaped aperture, although in other non-limiting embodiments, a star-shaped aperture, a square-shaped aperture, or any other shapes aperture may be utilized. Aperture 1630 is offset from axis 1604 at an angle 1640. Angle 1640 determines the angle for rotation of lag screw member 1415 when bulbous portion 1510 (shown in FIG. 15) resides in aperture 1630 with lag screw member 1415 rotating angularly around axis 1602. It should be appreciated that angle 1640 may be any angle less than 90 degrees to allow a surgeon the flexibility of fixing the rotation of polyaxial screw member 1410 and lag screw member 1415.

Further, polyaxial screw member 1410 has a smooth exterior portion 1605 having a uniform diameter from end 1625 to end 1650. The diameter of exterior portion 1605 is smaller than the diameter of aperture 1630. Polyaxial screw member 1410 is generally solid, however, in other non-limiting embodiments, polyaxial screw member 1410 may be cannulated. Further, portion 1605 terminates into a threaded portion 1615. Threaded portion 1615 is generally solid and includes a plurality of circular threads, such as threads 1655, circumferentially disposed on the external surface of threaded portion 1615. Threaded portion 1615 has a uniform diameter that is slightly larger than the diameter of portion 1605. However, in other non-limiting embodiments, the respective diameters of portions 1605 and 1615 may be substantially the same. Threaded portion 1615 may also be provided with a self-tapping leading edge (not shown) to provide portion 1615 with the ability to remove bone material during insertion of proximal screw member 1410 into bone. It should be appreciated that the length of the proximal screw member 1410 may be selected of varying lengths to allow a surgeon to fuse different joints in the human body. It should be appreciated that polyaxial screw member 1410 may be coated with an osteoconductive material, such as, for example, plasma spray or other similar types of porous materials that is capable of supporting or encouraging bone ingrowth into this material.

Figure 17:
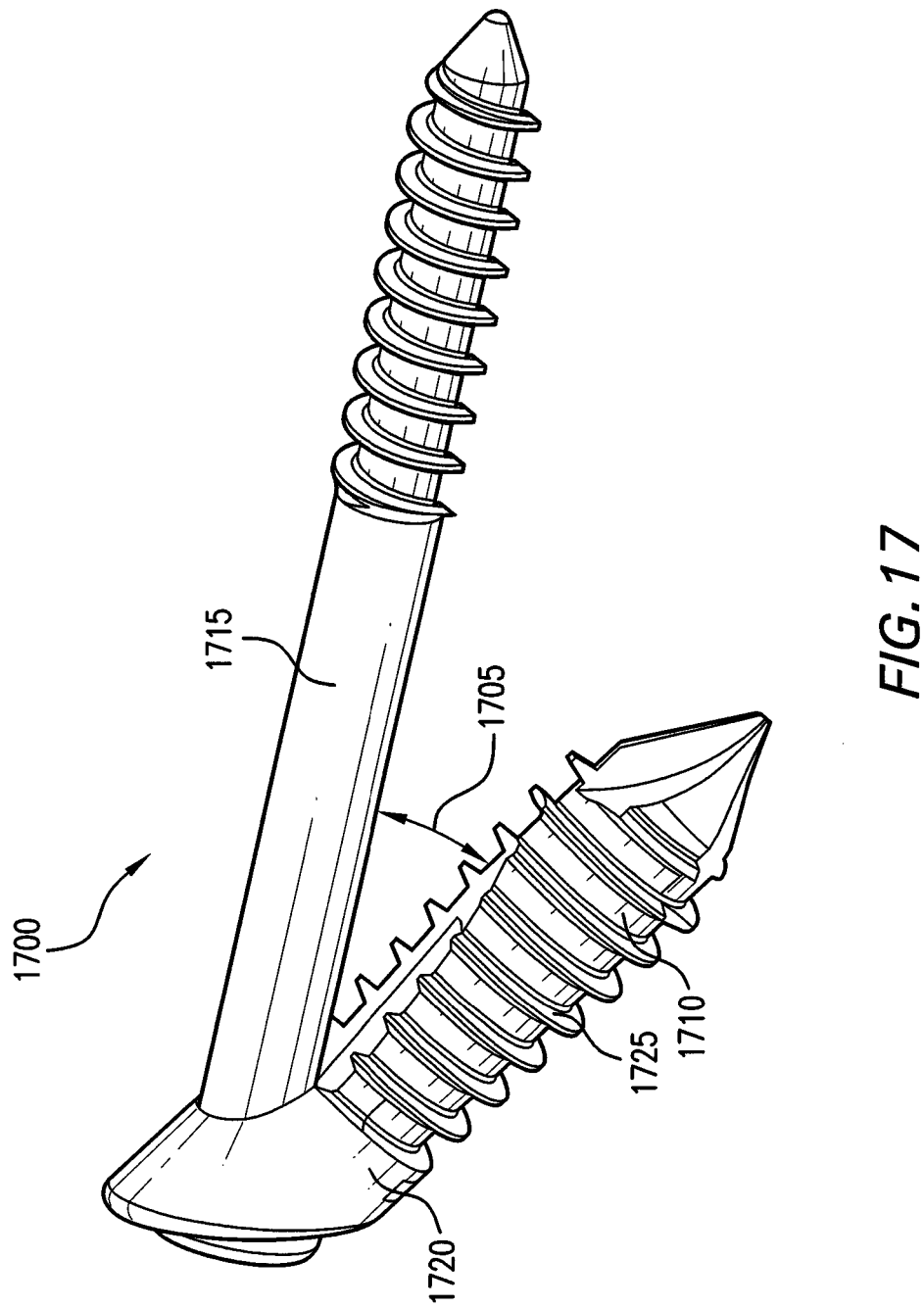
FIG. 17 is a perspective view of an assembled intramedullary fixation assembly according to an alternate embodiment of the invention.

In another alternate embodiment, as shown in FIG. 17, length of the polyaxial screw member 1710 may be varied in order to accommodate the intramedullary fixation assembly 1700 in bones of various sizes. Particularly, the polyaxial screw member 1710 includes a smooth end portion 1720 coupled directly to a threaded portion 1725, thereby varying the angle 1705 that is formed between the polyaxial screw member 1710 and the lag screw member 1715. In all other respects, the intramedullary fixation assembly 1700 is substantially similar to the intramedullary fixation assembly 1400 as was shown and described in FIG. 14.

Figure 18:
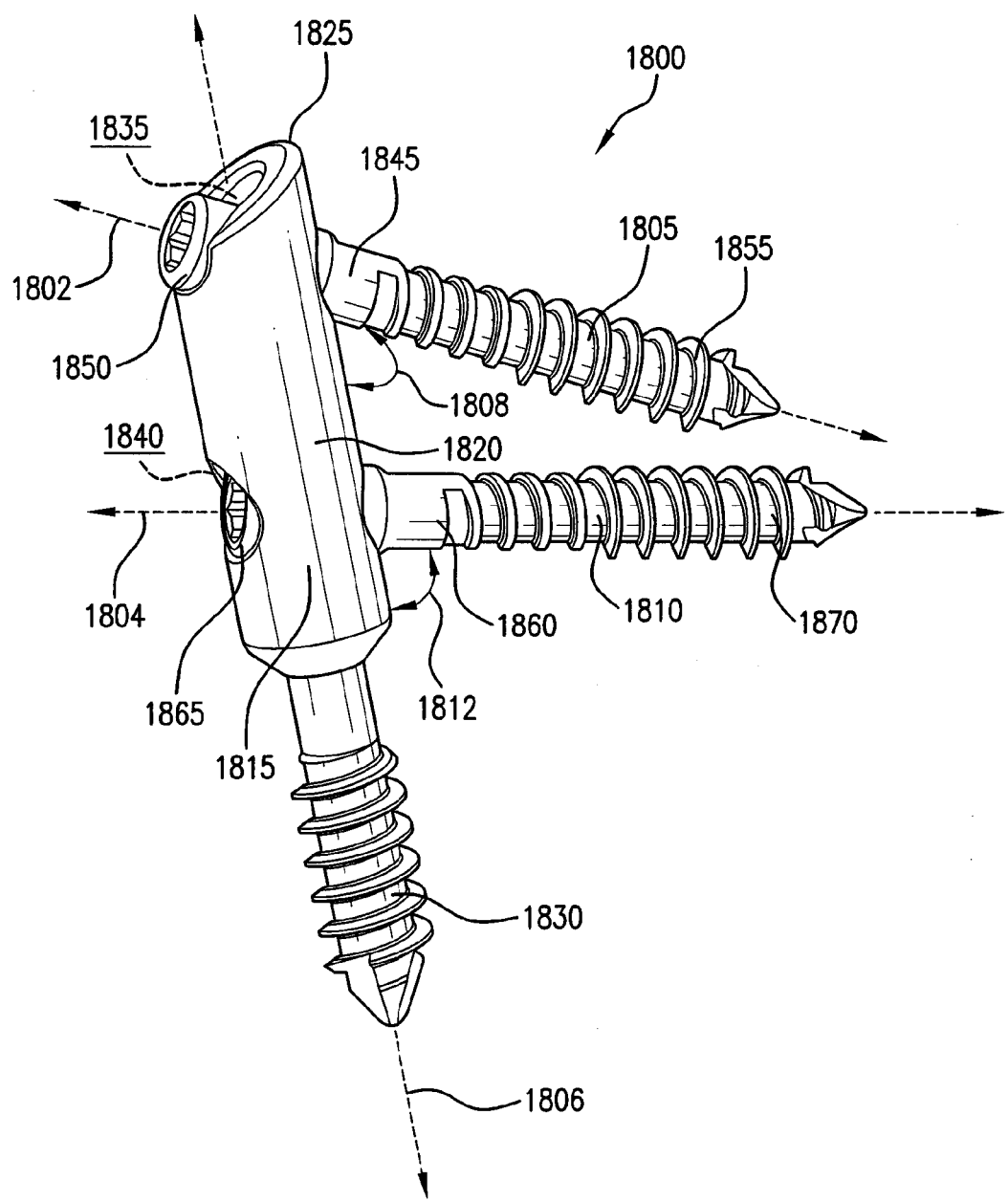
FIG. 18 is a perspective view of an assembled intramedullary fixation assembly having a plurality of lag screw members according to an alternate embodiment of the invention.

In another alternate embodiment, as shown in FIG. 18, an intramedullary fixation assembly 1800 having a plurality of lag screw members 1805 and 1810 coupled to a tapered screw member 1815 is provided in order to apply compression at multiple points on the bone fragment surface. Particularly, the lag screw members 1805 and 1810, and the tapered screw member 1815 are substantially similar to the lag screw member 815 and tapered screw member 810 respectively shown and described in the embodiment of FIGS. 8-11. Each of the lag screw members 1805 and 1810 forms an fixed acute angle with the tapered screw member 1815, with these angles being predetermined by, for example, a surgeon to fix the bones in a human body.

As shown, tapered screw member 1815 is generally cylindrical in shape and has a smooth exterior portion 1820 that extends longitudinally along axis 1806 from end 1825 to a threaded portion 1830. Further, end 1825 has a tapered aperture 1835, which is aligned on axis 1802 and forms a fixed angle 1808 with axis 1806. Fixed angle 1808 determines the angle for fixation of tapered screw member 1810 with respect to lag screw member 1805. Also, tapered screw member 1815 has a second tapered aperture 1840, aligned along axis 1804 and forms a fixed angle 1812 with axis 1804. The fixed angle 1812 determines the angle for fixation of lag screw member 1810 with tapered screw member 1815. It should be appreciated that fixed angles 1808 and 1812 may be any angle less than 90 degrees to allow a surgeon the flexibility of determining the angle for internal fixation of bones in the human body. It should also be appreciated that tapered screw member 1815 creates a locked interference fit with each of the lag screw members 1805 and 1810.

Further, tapered screw member 1815 has a smooth exterior portion 1820 having a uniform diameter from end 1825 to threaded portion 1830. Tapered screw member 1815 is generally solid, however, in other non-limiting embodiments, screw member 1815 may be cannulated. Further, threaded portion 1830 is generally solid and includes a plurality of circular threads circumferentially disposed on the external surface of threaded portion 1830. Threaded portion 1830 may also be provided with a self-tapping leading edge to provide portion 1830 with the ability to remove bone material during insertion of tapered screw member 1815 into bone. It should be appreciated that the length of the tapered screw member 1815 may be selected of varying lengths to allow a surgeon to fuse different joints in the human body. It should be appreciated that tapered screw member 1815 may be coated with an osteoconductive material, such as, for example, plasma spray or other similar types of porous materials that is capable of supporting or encouraging bone ingrowth into this material.

Also as shown in FIG. 18, each of the respective lag screw members 1805 and 1810 are substantially similar to the lag screw member of the embodiment shown and described in FIG. 10. Particularly, lag screw member 1805 is generally cylindrical in shape and has a first smooth exterior portion 1845 that extends from bulbous portion 1850 to a threaded portion 1855, while lag screw member 1810 has a smooth exterior portion 1860 that extends from bulbous portion 1865 to threaded portion 1870. Additionally, each of the bulbous portions 1850 and 1865 have a taper, such as a Morse taper, that provides for a locked interference fit with tapered apertures 1835 and 1840 respectively.

Figure 19:
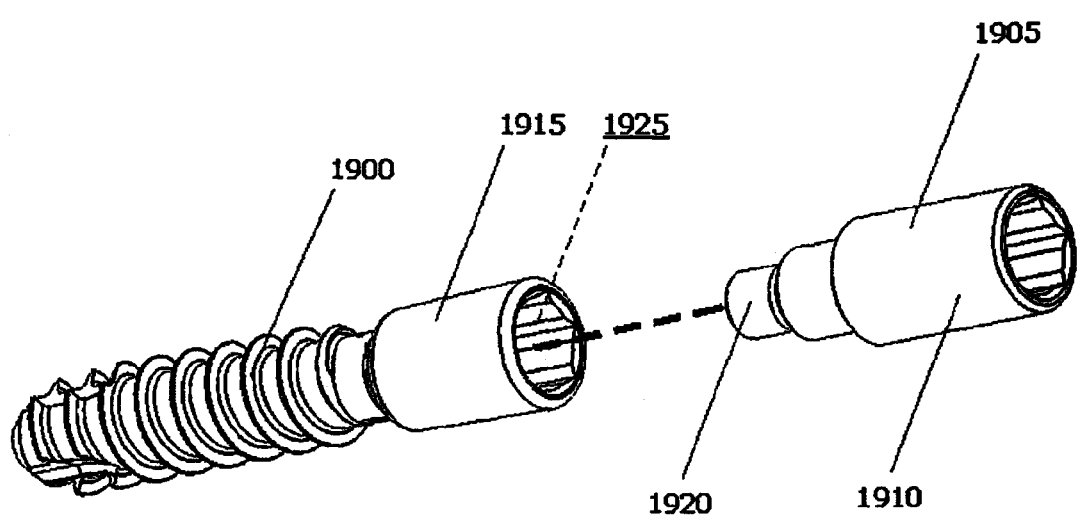
FIG. 19 is an exploded perspective view of a cover member for a lag screw according to an alternate embodiment of the invention.

In an alternate embodiment, as shown in FIG. 19, a lag screw member 1900 may include a cover or plug member 1905. The cover member 1905 includes a first end portion 1910 having substantially the same diameter as end portion 1915. The cover member 1905 also includes a second end portion 1920, which is smaller than the internal diameter of end portion 1915 and which is provided to be received inside aperture 1925 of lag screw member 1900.

In other alternate embodiments, as shown in FIGS. 20A-21B, an intramedullary fixation assembly having interconnected members is provided for intraosseous fixation and to apply an acute angle compression to bones. In particular, intramedullary fixation assembly 2000 (FIGS. 20A-20B) is provided for applying compression to bones at an acute angle, which is at a variable or an intramedullary fixation assembly 2100 (FIGS. 21A-21B) is provided for applying compression to bones at a predetermined and fixed acute angle. Further, the interconnected members of each of the intramedullary fixation assemblies 2000 or 2100 may be made from a Titanium material, although, in other non-limiting embodiments, either of these intramedullary fixation assemblies 2000 or 2100 may be made from SST, PEEK, NiTi, Cobalt Chrome or other similar types of materials.

Figure 20A:
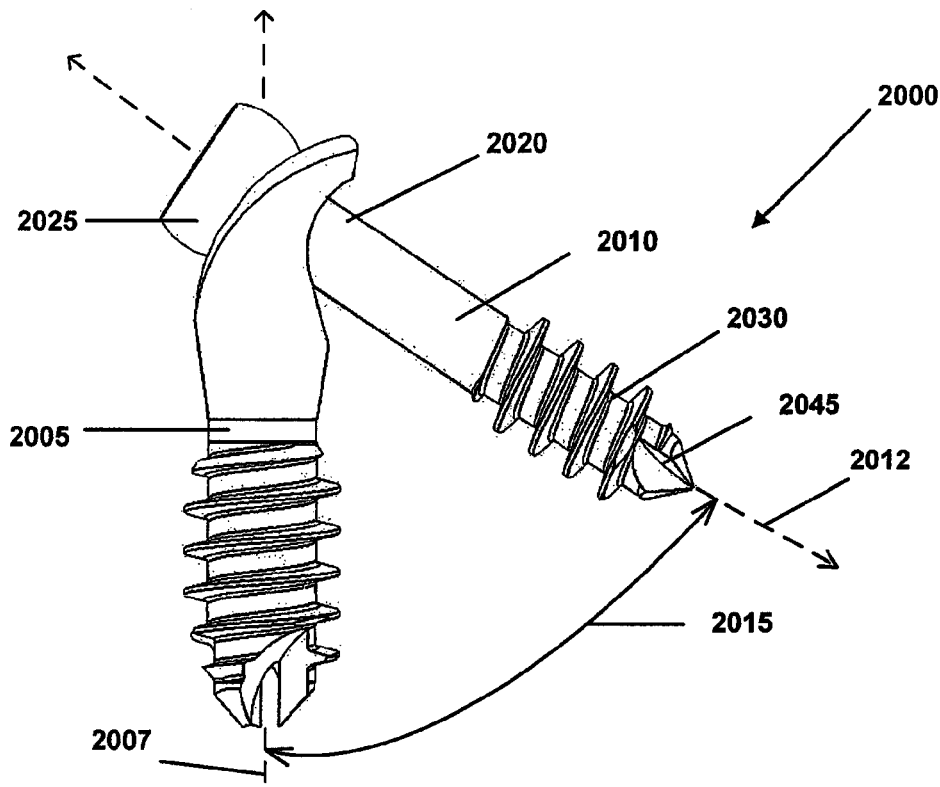
FIG. 20A is a perspective view of an intramedullary fixation assembly having a polyaxial screw member according to an alternate embodiment of the invention.
Figure 20B:
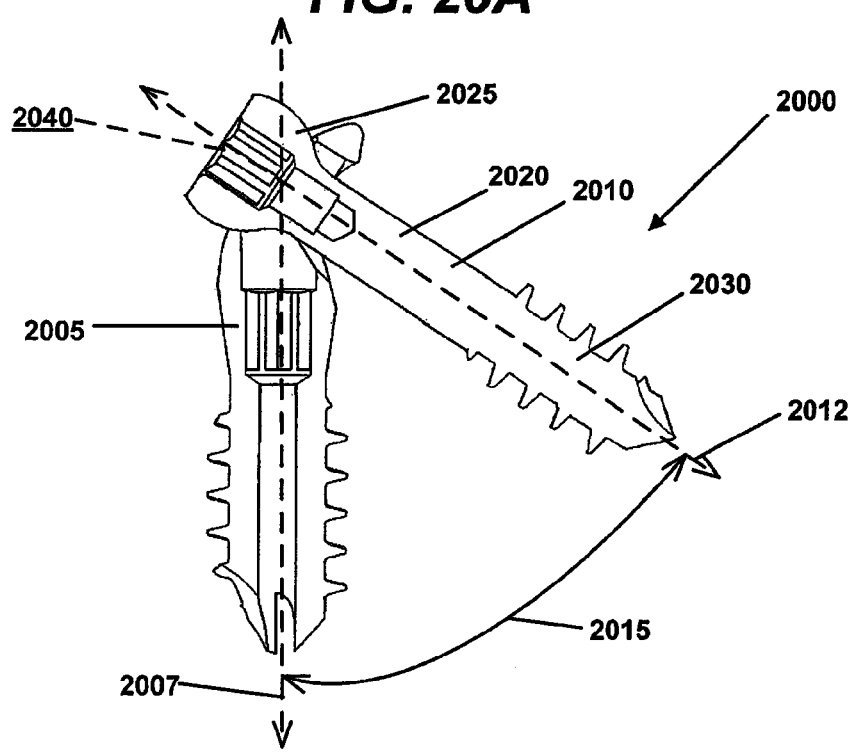
FIG. 20B is a cross-sectional view of the intramedullary fixation assembly shown in FIG. 20A according to an alternate embodiment of the invention.

As shown in FIGS. 20A-20B, intramedullary fixation assembly 2000 is provided to apply compression at an acute angle that is variable between 0 and 90 degrees prior to compression, after which compression is applied to set the angle of fixation. Particularly, the intramedullary fixation assembly 2000 includes a hybrid screw member 2005 aligned along longitudinal axis 2007 and being coupled to a polyaxial screw member 2010, with the hybrid screw member 2005 forming an acute angle 2015 with the longitudinal axis 2012 of polyaxial screw member 2010. The acute angle 2015 between the hybrid screw member 2005 and the polyaxial screw member 2010 causes the intramedullary fixation assembly 2000 to "hook" into bone segments and translates the compression applied to these bone segments across the members 2005 and 2010. The hybrid screw member 2005 is described in the embodiment shown in FIGS. 22A-22B.

The polyaxial screw member 2010, shown in FIGS. 20A-20B, is substantially similar to the lag screw member 1415 shown and described in FIG. 15, and includes a generally cylindrically-shaped longitudinal body 2020 that extends from a bulbous portion 2025 to a threaded portion 2030. The threaded portion 2030 has a plurality of helical threads on the external surface of threaded portion 2030. The threaded portion 2030 may also be provided with a self-tapping leading edge 2045 (FIG. 20A) for removing bone material during insertion of the polyaxial screw member 2010 into bone. Polyaxial screw member 2010 has several widths as we traverse its length, with a first diameter at body 2020 for allowing the body 2020 to traverse aperture 2230 (FIG. 22A-22B), while bulbous portion 2025 has a second diameter or width for causing the portion 2025 to abut the head portion 2205 (FIGS. 22A-22B) and restrain the polyaxial screw member against the hybrid screw member 2005. The bulbous portion 2025 is provided for rotational movement of polyaxial screw member 2010 along its longitudinal axis at various angles less than 90 degrees with respect to the hybrid screw member 2005 after insertion of the polyaxial screw member 2010 into the hybrid screw member 2005, however prior to applying compression. Also, bulbous portion 2025 has a generally hexagonal-shaped aperture 2040 (FIG. 20B) residing within the bulbous portion 2025 and being aligned along the longitudinal axis of polyaxial screw member 2010. In other non-limiting embodiments, a star-shaped aperture, a square-shaped aperture, or any other shaped aperture may be provided without departing from the scope of the invention. Aperture 2040 is provided to transmit torque from bulbous portion 2025 to threaded portion 2030 as bulbous portion 2025 is rotated with a complementary shaped tool in a direction that causes a corresponding rotation of threaded portion 2030. In one embodiment, polyaxial screw member 2010 is non-cannulated or solid, although in another non-limiting embodiment, the polyaxial screw member 2010 is cannulated (i.e., screw member 2010 has a continuous internal opening longitudinally coextensive with the length of the polyaxial screw member 2010). It should be appreciated that the length of the polyaxial screw member 2010 may be selected of varying lengths to allow a surgeon to fuse different joints in the human body. It should also be appreciated that the polyaxial screw member 2010 may be coated with an osteoconductive material, such as, for example, plasma spray or other similar type of porous material that is capable of supporting or encouraging bone ingrowth into this material.

Figure 21A:
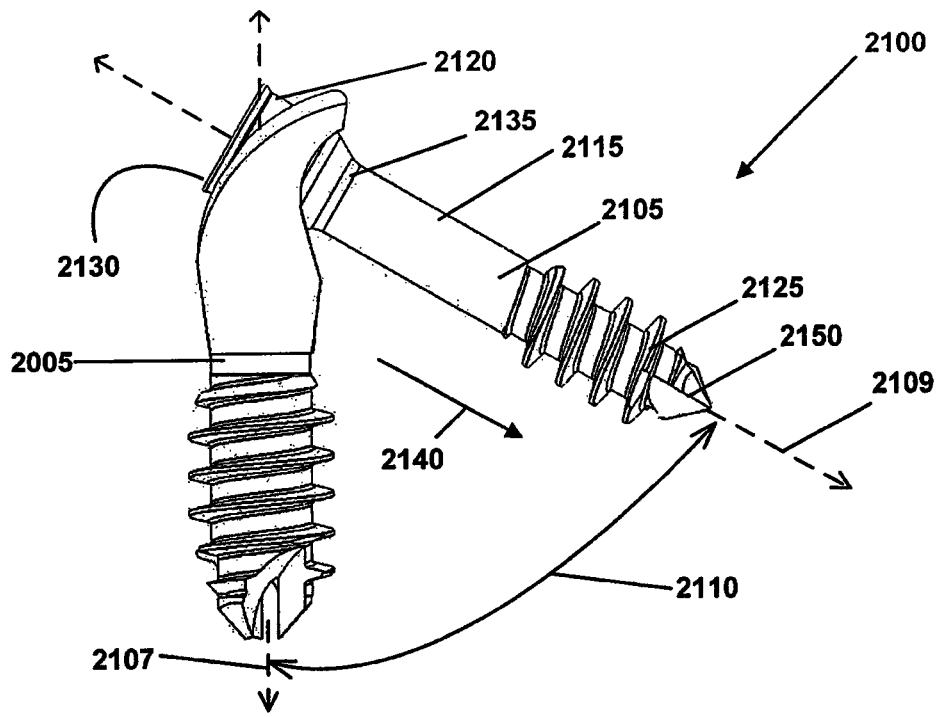
FIG. 21A is a perspective view of an intramedullary fixation assembly having a tapered screw member according to an alternate embodiment of the invention.
Figure 21B:
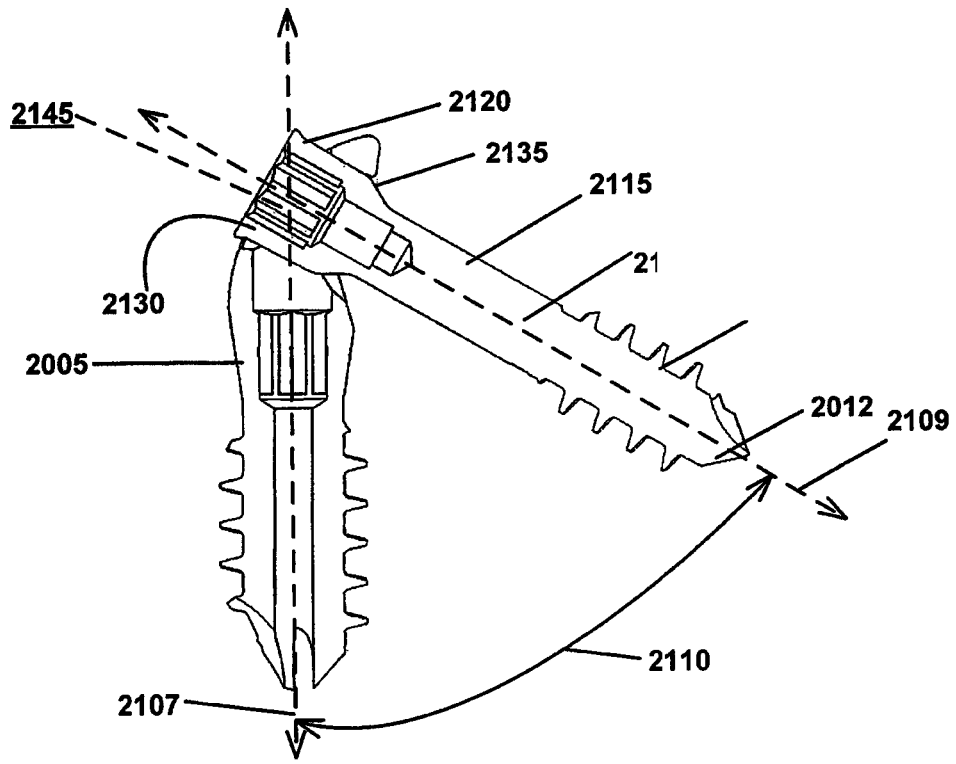
FIG. 21B is a cross-sectional view of the intramedullary fixation assembly shown in FIG. 21A according to an alternate embodiment of the invention.

As shown in FIGS. 21A-21B, intramedullary fixation assembly 2100 is provided to apply compression at an acute angle that is fixed at a predetermined angle between 0 and 90 degrees depending on the bone segments that are being compressed. As shown, the intramedullary fixation assembly 2100 includes a hybrid screw member 2005 aligned along axis 2107 and being coupled to a tapered screw member 2105 that is aligned along axis 2109, with the hybrid screw member 2005 forming an acute angle 2110 with the tapered screw member 2105. The acute angle 2110 is fixed at a predetermined angle, and similarly, causes the intramedullary fixation assembly 2100 to "hook" into the bone segments and translates the compression applied to bone fragments into uniform compression through multi-point fixation. As previously stated, the hybrid screw member 2005 is described in the embodiment shown in FIGS. 22A-22B.

The tapered screw member 2105, shown in FIGS. 21A-21B, is substantially similar to the lag screw member 815 shown and described in FIG. 10, and includes a generally cylindrically-shaped body 2115 that longitudinally extends from a bulbous portion 2120 to a threaded portion 2125. Threaded portion 2125 has a plurality of helical threads on an external surface of the threaded portion 2125. The threaded portion 2125 may also be provided with a self-tapping leading edge 2150 (FIG. 21A) for removing bone material during insertion of the tapered screw member 2105 into bone. The bulbous portion 2120 has a taper, such as a Morse taper, with a width that decreases from end 2130 to end 2135 (i.e., tapered portion has a slope in direction 2140). Additionally, body 2115 has a diameter for allowing the body 2115 to traverse the plurality of aperture 2230 (shown in FIGS. 22A-22B), while the Morse taper on bulbous portion 2120 allows for a locked interference with internal surface 2245 (shown in FIGS. 22A-22B) at a fixed angle between 0 and 90 degrees. Also, bulbous portion 2120 has a generally hexagonal-shaped aperture 2145 (FIG. 21B) residing within bulbous portion 2120 and being aligned along the longitudinal axis 2109 of tapered screw member 2105. In other non-limiting embodiments, a star-shaped aperture, a square-shaped aperture, or any other shaped aperture may be utilized without departing from the scope of the invention. Aperture 2145 is provided to transmit torque from bulbous portion 2120 to threaded portion 2125 as bulbous portion 2120 is rotated with a complementary shaped tool, received within aperture 2145, in a direction that causes a corresponding rotation of threaded portion 2125. In one embodiment, tapered screw member 2105 is non-cannulated or solid, although in another non-limiting embodiment, the tapered screw member 2105 is cannulated (i.e., screw member 2105 has a continuous internal opening longitudinally coextensive with the length of tapered screw member 2105). It should be appreciated that the length of the tapered screw member 2105 may be selected of varying lengths to allow a surgeon to fuse different joints in the human body. It should also be appreciated that the tapered screw member 2105 may be coated with an osteoconductive material, such as, for example, plasma spray or other similar type of porous material that is capable of supporting or encouraging bone ingrowth into this material.

Figure 22A:
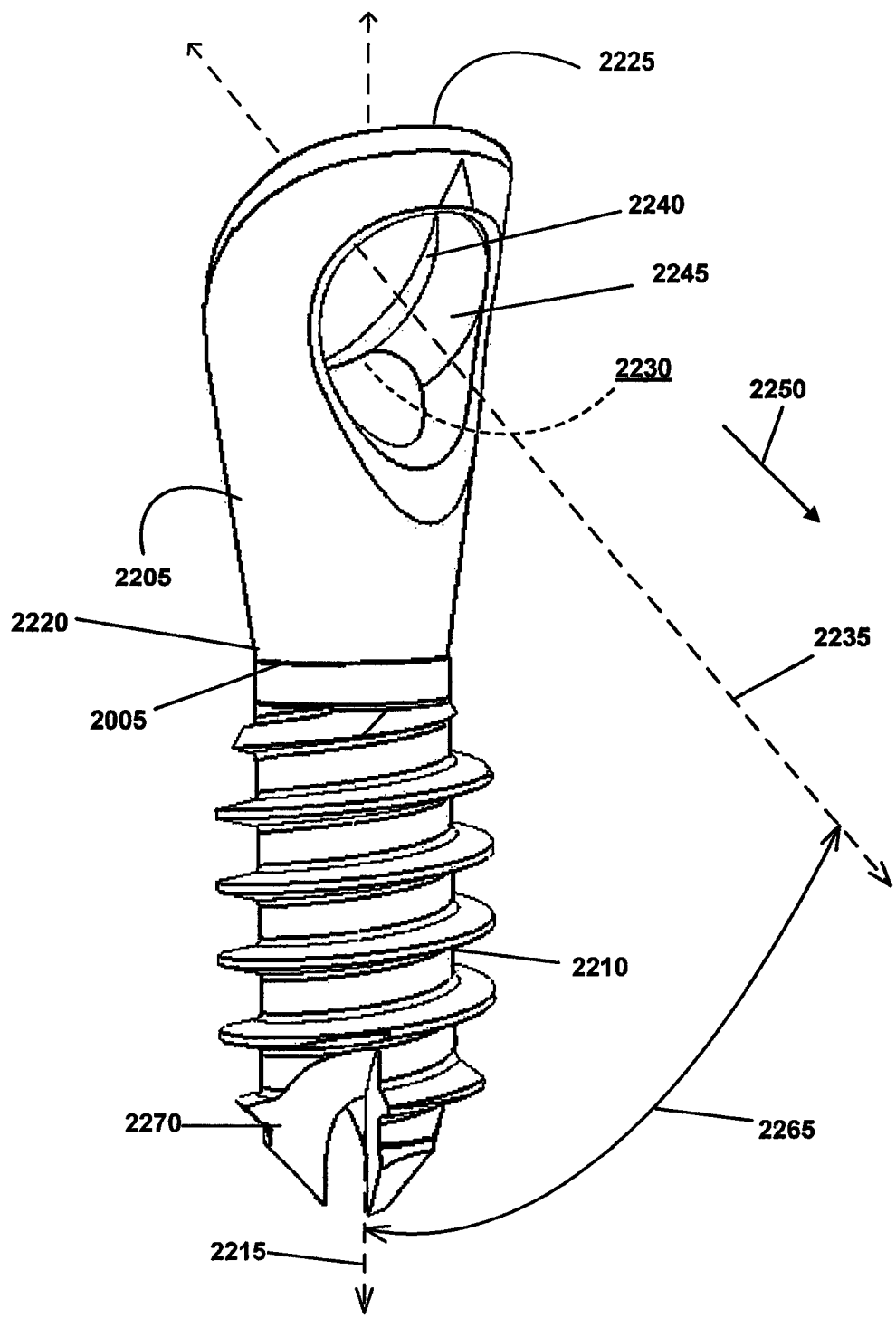
FIG. 22A is a perspective view of a hybrid screw member used in the intramedullary fixation assembly shown in FIGS. 20A-21B according to an alternate embodiment of the invention.
Figure 22B:
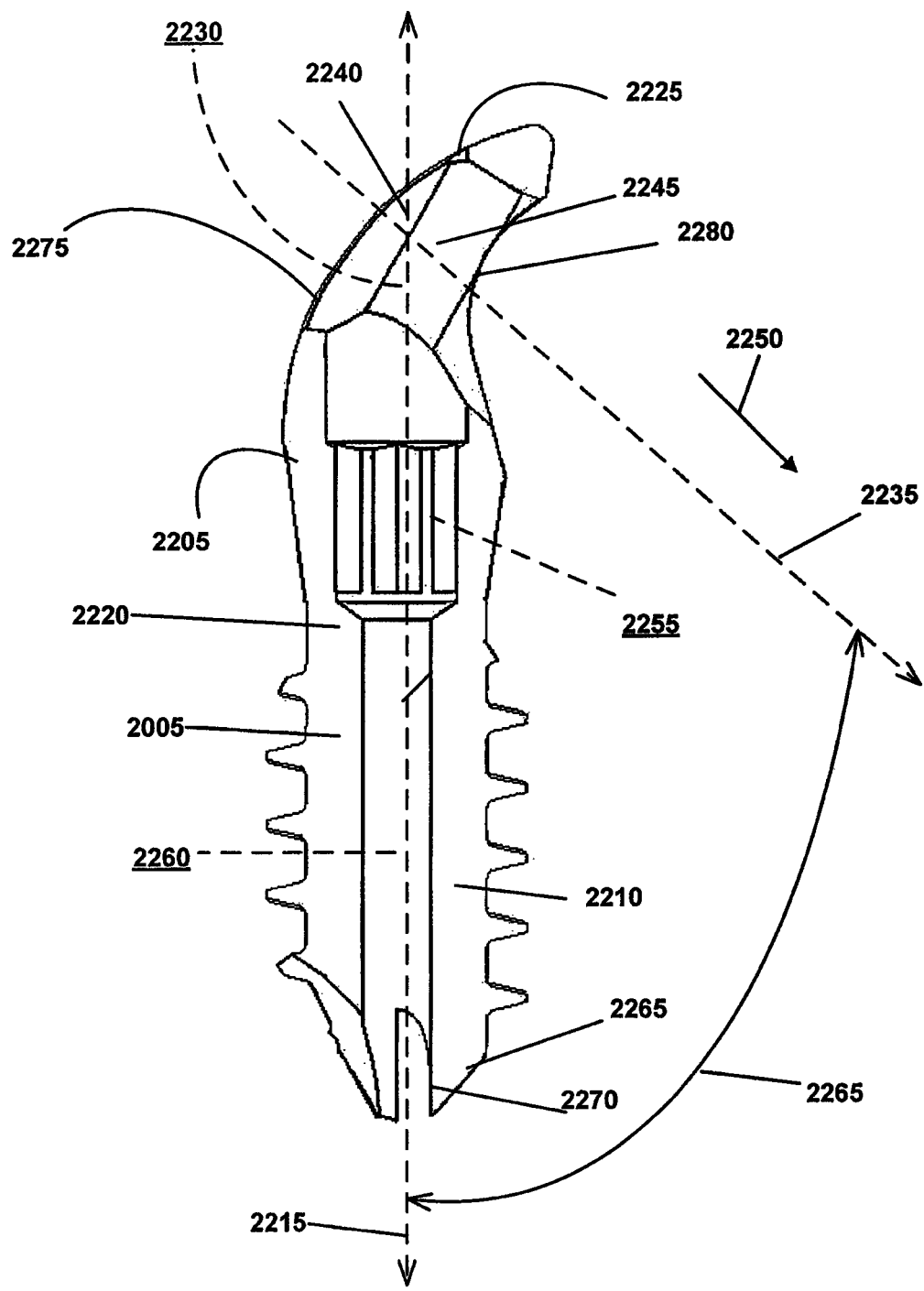
FIG. 22B is a sectional view of the hybrid screw member shown in FIG. 22A according to an alternate embodiment of the invention.

As shown in FIGS. 22A-22B, hybrid screw member 2005 is generally cylindrical in shape and has a head portion 2205 coupled to a threaded portion 2210. The hybrid screw member 2005 is aligned along longitudinal axis 2215, which is longitudinally coextensive with length of hybrid screw member 2005. The threaded portion 2210 has a uniform diameter and includes a plurality of helical threads on an external surface of portion 2210. Threaded portion 2210 may also be provided with a self-tapping leading edge 2270 for removing bone material during insertion of the hybrid screw member 2005 into bone.

Further, head portion 2205 is generally tubular in shape and has a generally tapered external surface from first end 2220 to second end 2225 (i.e. head portion 2205 decreases slightly in diameter from end 2220 to end 2225). Also, head portion 2205 has a central aperture or bore 2230 that is aligned along axis 2235, with central aperture 2230 forming an acute angle 2265 with longitudinal axis 2215 (i.e., central aperture 2230 extends from a first surface 2275 (FIG. 22B) to opposed surface 2280 (FIG. 22B) along axis 2235). The central aperture 2230 is formed from a plurality of apertures formed on the internal surface of the head portion 2205. Particularly, internal surface 2240 has a spherical radius that defines a first aperture within the central aperture 2230 while internal surface 2245 has a second radius that defines a second aperture 2230 within central aperture 2230. The internal surface 2240 is provided to receive the bulbous portion 2025 of polyaxial screw member 2010 (FIGS. 20A-20B) and surface 2245 is provided to receive bulbous portion 2120 of tapered screw member 2105 (FIGS. 22A-22B). Additionally, internal surface 2245 has a taper that decreases from first surface 2275 (FIG. 22B) in direction 2250. It should be appreciated that the taper on internal surface 2245 is provided to receive bulbous portion 2120 in order to cause bulbous portion 2120 to create a locked interference fit with internal surface 2245 and align the hybrid screw member 2005 and the tapered screw member 2105 (FIGS. 21A-21B) along this axis 2235. It should also be appreciated that the bulbous portion 2025 (FIGS. 20A-20B) is restrained at internal surface 2245, while the threaded portion 2030 (FIGS. 20A-20B) may rotate in a circumference that is orthogonal to the axis 2235, with this polyaxial screw member 2010 maintaining its acute angle position with respect to the hybrid screw member 2005. The angle 2265 may predetermined to be any angle less than 90 degrees to allow a surgeon the flexibility of setting the angle for compression as well the flexibility of fixing bones of various sizes.

Further, head portion 2205 has a generally hexagonal shaped aperture 2255 (FIG. 22B) residing within head portion 2205 and being aligned along the longitudinal axis 2215. In other non-limiting embodiments, a star-shaped aperture, a square-shaped aperture, or any other shaped aperture may be utilized without departing from the scope of the invention. Aperture 2255 is accessible at one end through aperture 2230 and is also coupled at a second end to longitudinal aperture 2260, which is longitudinally coextensive with threaded portion 2210 from end 2220 to end 2265 (i.e., hybrid screw member 2005 is cannulated). Aperture 2255 is provided to transmit torque from head portion 2205 to threaded portion 2210 as head portion 2205 is rotated when a complementary shaped tool is received in aperture 2255 and rotated in a direction that causes a corresponding rotation of threaded portion 2210. It should be appreciated that the length of the hybrid screw member 2005 may be selected of varying lengths to allow a surgeon to fuse different joints in the human body. It should also be appreciated that hybrid screw member 2005 may be coated with an osteoconductive material, such as, for example, plasma spray or other similar types of porous materials that is capable of supporting or encouraging bone ingrowth into this material.

In operation, and as best shown in FIGS. 20A-22B, each of the intramedullary fixation assemblies 2000 and 2100 may be utilized for treating and fusing the deteriorated, damaged or fractured bones in the human body (not shown). In one-non limiting example, an incision is made in the foot to access the bones in the foot, and a first medullary canal is drilled in a first bone. The hybrid screw member 2005 (FIG. 22A) is inserted into the first medullary canal by coupling a complementary shaped tool into the hexagonal shaped aperture 2255 (FIG. 22B) and rotating the hybrid member 2005 to cause the member 2005 to travel into bone and reside substantially within the bone. The position of the hybrid screw member 2005 is assessed and adjustments may be made with respect to the position of the aperture 2230 (FIGS. 22a-22B). Further, a second medullary canal is drilled in the first bone or another adjacent bone at a predetermined acute angle. In one non-limiting embodiment, a polyaxial screw member 2010 (FIGS. 20A-20B) is selected and inserted into the hybrid screw member 2005 at a predetermined angle selected by a surgeon, although in another embodiment, the tapered screw member 2105 (FIGS. 21A-21B) may be selected and inserted into the hybrid screw member 2005 (FIGS. 21A-21B). The polyaxial screw member 2010 is inserted into the hybrid screw member 2005 (FIGS. 20A-20B) by inserting the threaded portion 2030 (FIGS. 20A-20B) into the aperture 2230 (FIG. 22B) and into the second medullary canal by coupling a complementary shaped tool in hexagonal shaped aperture 2040 (FIG. 20B) and rotating polyaxial screw member 2010 to cause polyaxial screw member 2010 to travel into the second medullary canal until bulbous portion 2025 (FIG. 20A) abuts internal surface 2240. The polyaxial screw member 2010 is further rotated to apply compression to the polyaxial screw member 2010 to lock the polyaxial screw member 2010 to the hybrid screw member 2005, thereby fusing the damaged or deteriorated bones.

It should be appreciated that the intramedullary fixation assembly 2000 is provided to be inserted into, for example, the joints of the human foot by incorporating either a polyaxial screw member 2010 or a tapered screw member 2105 so as to provide for acute angle compression of these joints. It should also be appreciated that the intramedullary fixation assembly 2000 is delivered through an incision and is provided to be substantially within the bone (i.e., intraosseous), thereby reducing the disruption to the plantar tissues while at the same time minimizing the tension on the skin. This allows for improved wound closure, reduced operating room time, reduction in the number of incisions required and reduction in the total length of incisions It should also be appreciated that in other non-limiting embodiments, the intramedullary assembly 2000 may be utilized with graft material (i.e., autograft, allograft or other biologic agent).

Figure 25:
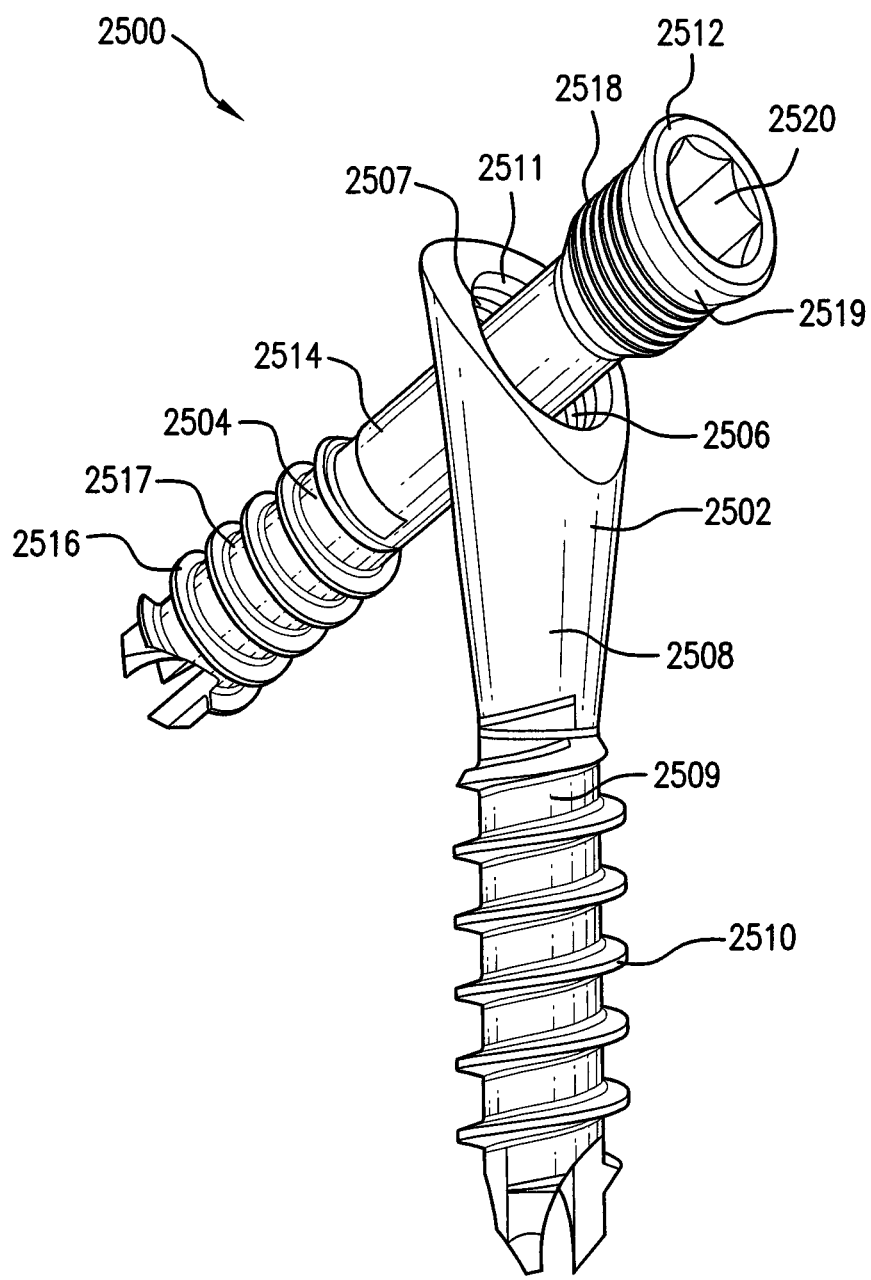
FIG. 25 is a perspective view of an intramedullary fixation assembly according to an alternate embodiment of the invention.

Referring now to FIG. 25, another embodiment of an intramedullary fixation assembly 2500 is illustrated comprising two interconnected members. Intramedullary fixation assembly 2500 preferably contains several substantially similar features and performs substantially similar functions as previously described for intramedullary fixation assemblies 800, 1300, 1400, 1700, 2000, and 2100. That is, intramedullary fixation assembly 2500 may be used to fuse and/or fixate bone(s) by coupling the interconnected members to the bone(s). More specifically, intramedullary fixation assembly 2500 comprises a tapered screw member 2502 and a lag screw member 2504. Tapered screw member 2502 preferably contains several substantially similar features and performs substantially similar functions as previously described for tapered screw members 810 and 1310, polyaxial screw members 1410 and 1710, and hybrid screw member 2005. Specifically, tapered screw member 2502 contains an aperture 2506, a shaft 2508 extending from aperture 2506, and threads 2510 disposed on the external surface 2509 of shaft 2508. The features and functions of aperture 2506, shaft 2508, and threads 2510 have all been previously described above with respect to tapered screw members 810, 1310, polyaxial screw members 1410, 1710, and hybrid screw member 2005. For example, threads 2510 are preferably used to fixate tapered screw member 2502 into a bone and aperture 2506 is preferably used to receive and form a locked interference fit with lag screw member 2504. Tapered screw member 2502 preferably comprises a plurality of threads or grooves 2507 disposed on the interior surface 2511 of aperture 2506. Preferably, grooves 2507 are provided in a helix around the circumference of the interior surface 2511 of aperture 2506 in order receive threads 2518 of lag screw member 2504. It should be understood that any commonly used helical threads or grooves used for receiving the threads of a commonly used screw may be provided on the interior surface 2511 of aperture 2506, without limiting the scope of the invention.

Lag screw member 2504 preferably contains several substantially similar features and performs substantially similar functions as previously described for lag screw members 815, 1315, 1415, and 1715, polyaxial screw member 2010, and tapered screw member 2105. Specifically, lag screw member 2504 contains a bulbous portion 2512, a shaft 2514 extending from bulbous portion 2512, threads 2516 disposed on the exterior surface 2517 of shaft 2514, and a torque-transmitting aperture 2520. The features and functions of bulbous portion 2512, shaft 2514, threads 2516, and torque-transmitting aperture 2520 have all been previously described above with respect to lag screw members, 815, 1315, 1415, and 1715, polyaxial screw member 2010, and tapered screw member 2105. For example, threads 2516 are preferably used to fixate lag screw member 2504 into a bone and bulbous portion 2512 is preferably used to couple to aperture 2506 in order for lag screw member 2504 to form a threaded locking connection with tapered screw member 2502. As discussed above with respect to aperture 1035, aperture 2520 is generally a hexagonal torque-transmitting aperture. However, a star-shaped aperture, a square-shaped aperture, or any other shaped aperture may be utilized without departing from the scope of the invention. Torque transmitting aperture 2520 is utilized to transmit a torque from bulbous portion 2512 to aperture 2506 in order to provide a screw thread engagement or threaded connection between lag screw member 2504 and tapered screw member 2502.

Lag screw member 2504 preferably comprises a plurality of threads 2518 disposed on the exterior 2519 surface of bulbous portion 2512. Preferably, threads 2518 are provided in a helix around the circumference of the exterior surface 2519 of bulbous portion 2512 in order to engage and couple to threads or grooves 2507 of tapered screw member 2502. It should be understood that any commonly used threads for engaging and coupling to commonly used threads or grooves in order to form a screw thread engagement may be used, without limiting the scope of the invention.

Intramedullary fixation assembly 2500 generally provides all of the features and benefits of intramedullary fixation assemblies 800, 1300, 1400, 1700, 2000, and 2100, as described above, while also providing a screw thread engagement between lag screw member 2504 and tapered screw member 2502. The screw thread engagement is provided by coupling threads 2518 provided on the exterior surface 2519 of bulbous portion 2512 of lag screw member 2504 to threads or grooves 2507 provided on the interior surface 2511 of aperture 2506 of tapered screw member 2502. The screw thread engagement is formed by sliding lag screw member 2504 through aperture 2506 of tapered screw member 2502, threads 2516 first, until bulbous portion 2512 is seated inside aperture 2506. Once seated within aperture 2506, lag screw member 2504 is rotated by inserting an appropriately shaped tool (not shown) inside torque-transmitting aperture 2520 and twisting or rotating the tool so that threads 2518 engage and couple to grooves 2507. Lag screw member 2504 is rotated until bulbous portion 2512 is sufficiently coupled to aperture 2506 of tapered screw member 2502. The screw thread engagement provides a stronger, more stable, and more secure threaded locking connection between lag screw member 2504 and tapered screw member 2502. While the use of a standard screw thread engagement has been described, it should be understood that a reverse screw thread engagement may be implemented without limiting the scope of the invention. Finally, it should be understood that the screw thread engagement consisting of threads 2518 disposed on exterior surface 2519 of bulbous portion 2512 coupled to threads or grooves 2507 disposed on the interior surface 2511 of aperture 2506, as just described, may be incorporated into any of the fixation assemblies 110, 800, 1300, 1400, 1700, 1800, 2000, 2100, 2300 (described below) and 2500, discussed above, as appropriate, in order to securely couple a lag screw member to a tapered screw member with a threaded locking connection, without limiting the scope of the invention. More specifically, it should be understood that any of the bulbous portions of any of the lag screw members or equivalents described throughout this specification may contain threads disposed on its exterior surface to be used to couple to threads or grooves disposed on the interior surface of any of the apertures of any of the tapered screw members or equivalents described throughout this specification in order to form a threaded engagement or threaded connection between any of the lag screw members or equivalents and the tapered screw members or equivalents, without limiting the scope of the invention.

Referring now to FIGS. 23A-23D, wherein like numerals indicate like elements throughout, an intramedullary fixation assembly 2300 is illustrated comprising two constructs each having two interconnected members. More specifically, intramedullary fixation assembly 2300 preferably comprises a radial construct 2302 and an ulnar construct 2304. Radial construct 2302 includes a tapered screw member 2306 and a lag screw member 2308. Tapered screw member 2306 may be any of the previously described tapered screw members, particularly, tapered screw members 810, 1310, and 2502; polyaxial screw members 1410 and 1710; and hybrid screw member 2005. As such, tapered screw member 2306 is substantially similar to and may contain substantially similar features and provide substantially similar functions as described with respect to each previously disclosed tapered screw members 810, 1310, and 2502; polyaxial screw members 1410 and 1710; and hybrid screw member 2005. Moreover, lag screw member 2308 may be any of the previously described lag screw members, particularly, lag screw members, 815, 1315, 1415, 1715, and 2504; polyaxial screw member 2010; and tapered screw member 2105. As such, lag screw member 2308 is substantially similar to and may contain substantially similar features and provide substantially similar functions as described with respect to each previously disclosed lag screw member, 815, 1315, 1415, 1715, and 2504; polyaxial screw member 2010; and tapered screw member 2105.

Ulnar construct 2304 includes a tapered screw member 2310 and a lag screw member 2312. Tapered screw member 2310 may be any of the previously described tapered screw members, particularly, tapered screw members 810, 1310, and 2502; polyaxial screw members 1410 and 1710; and hybrid screw member 2005. As such, tapered screw member 2310 is substantially similar to and may contain substantially similar features and provide substantially similar functions as described with respect to each previously disclosed tapered screw members 810, 1310, and 2502; polyaxial screw members 1410 and 1710; and hybrid screw member 2005.

Moreover, lag screw member 2312 may be any of the previously described lag screw members, particularly, lag screw members, 815, 1315, 1415, 1715, and 2504; polyaxial screw member 2010; and tapered screw member 2105. As such, lag screw member 2312 is substantially similar to and may contain substantially similar features and provide substantially similar functions as described with respect to each previously disclosed lag screw members, 815, 1315, 1415, 1715, and 2504; polyaxial screw member 2010; and tapered screw member 2105. The interconnected members 2306, 2308, 2310, and 2312 of each of the constructs 2302 and 2304 of intramedullary fixation assembly 2300 may be made from a Titanium material, although, in other non-limiting embodiments, intramedullary fixation assembly 2300 may be made from SST, PEEK, NiTi, Cobalt Chrome or other similar types of materials.

Figure 23A:
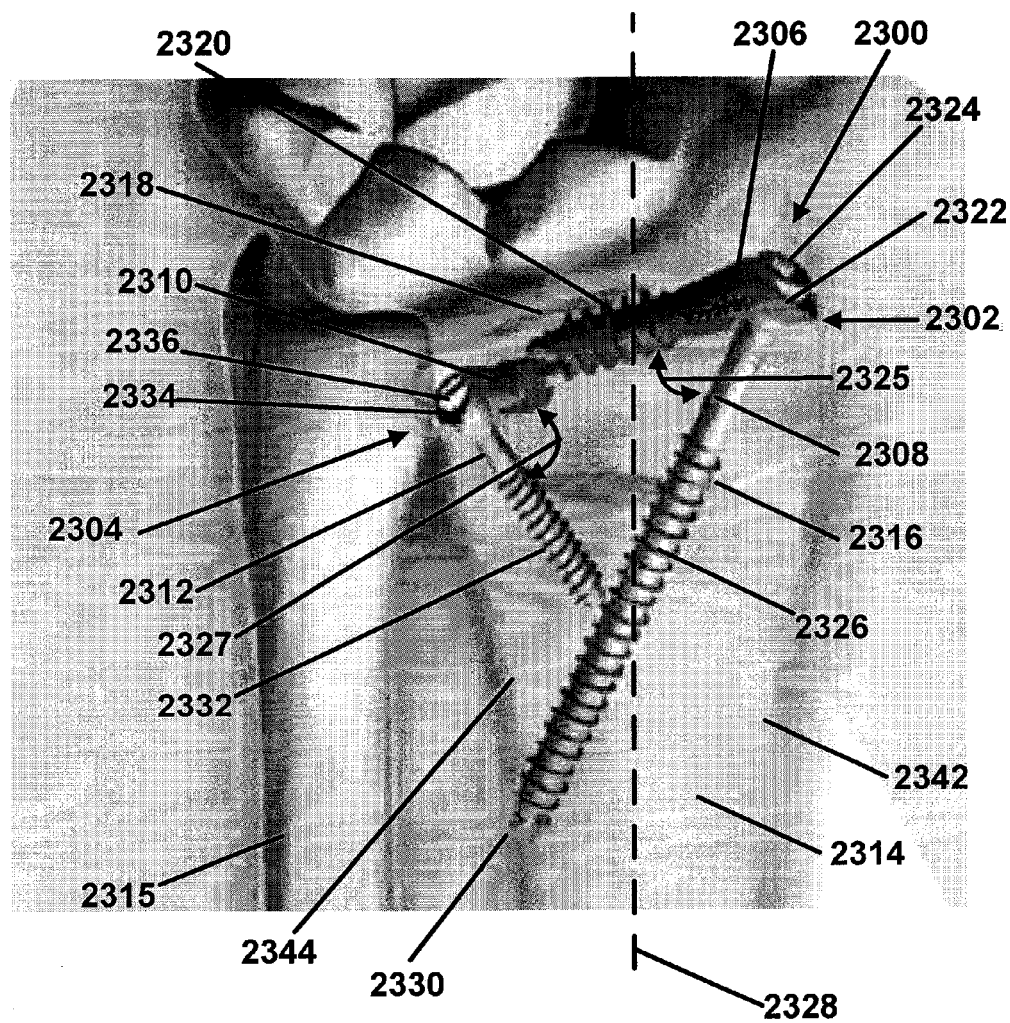
FIG. 23A is an image illustrating a perspective view of an intramedullary fixation assembly according to an alternate embodiment of the invention.
Figure 23B:
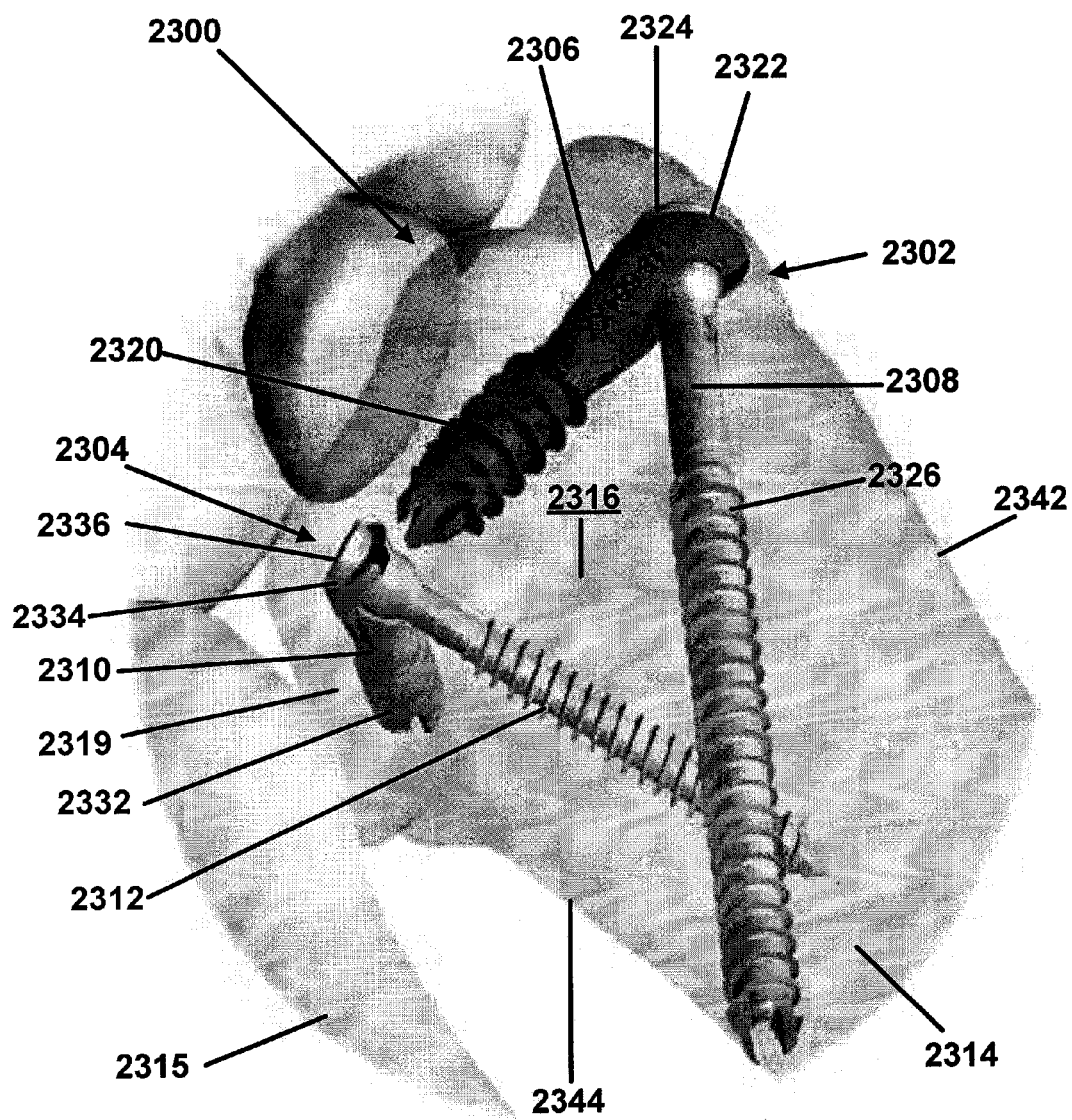
FIG. 23B is an image illustrating another perspective view of the intramedullary fixation assembly shown in FIG. 23A according to an alternate embodiment of the invention.
Figure 23C:
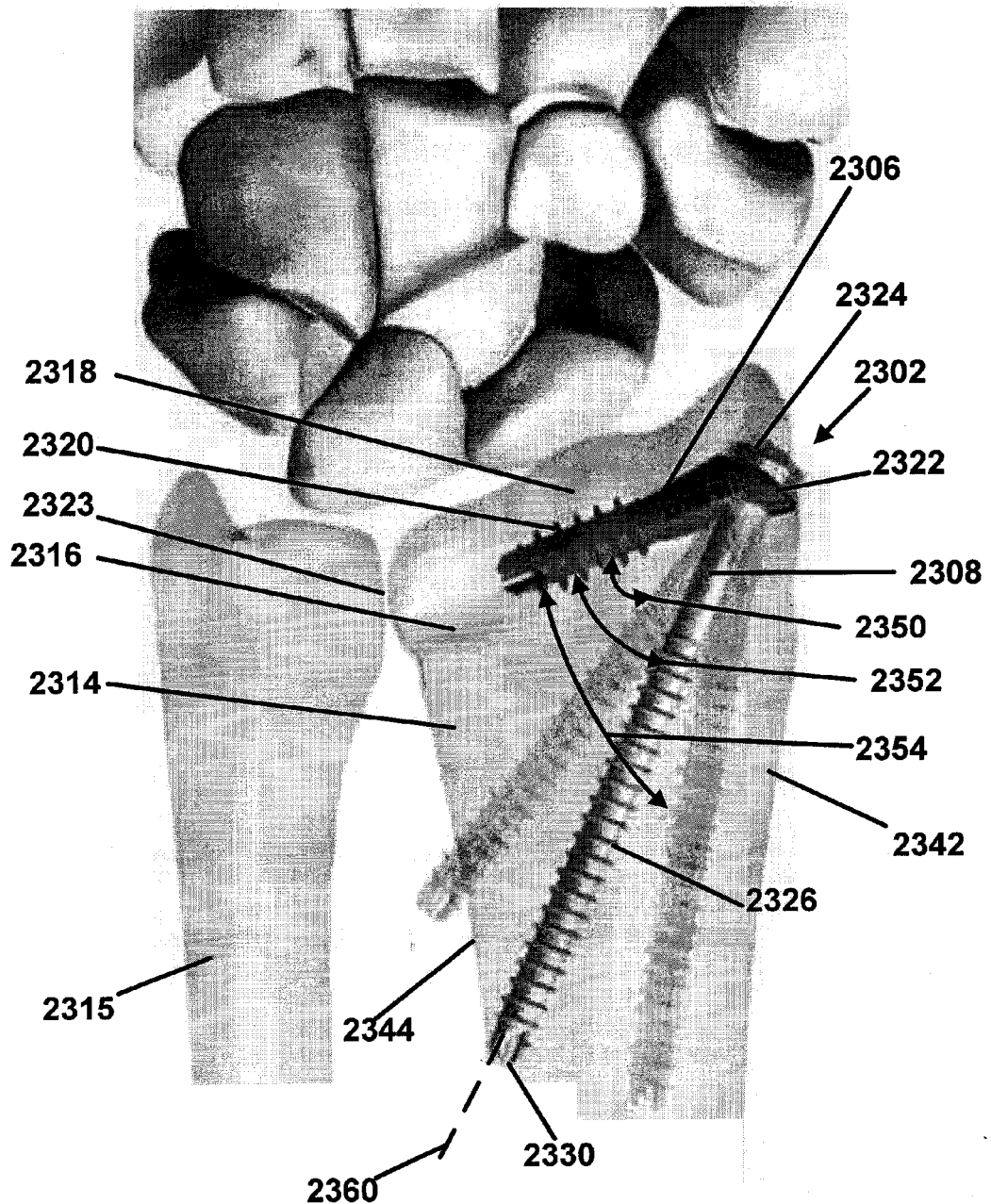
FIG. 23C is an image illustrating the radial construct of the intramedullary fixation assembly shown in FIGS. 23A and 23B according to an alternate embodiment of the invention.
Figure 23D:
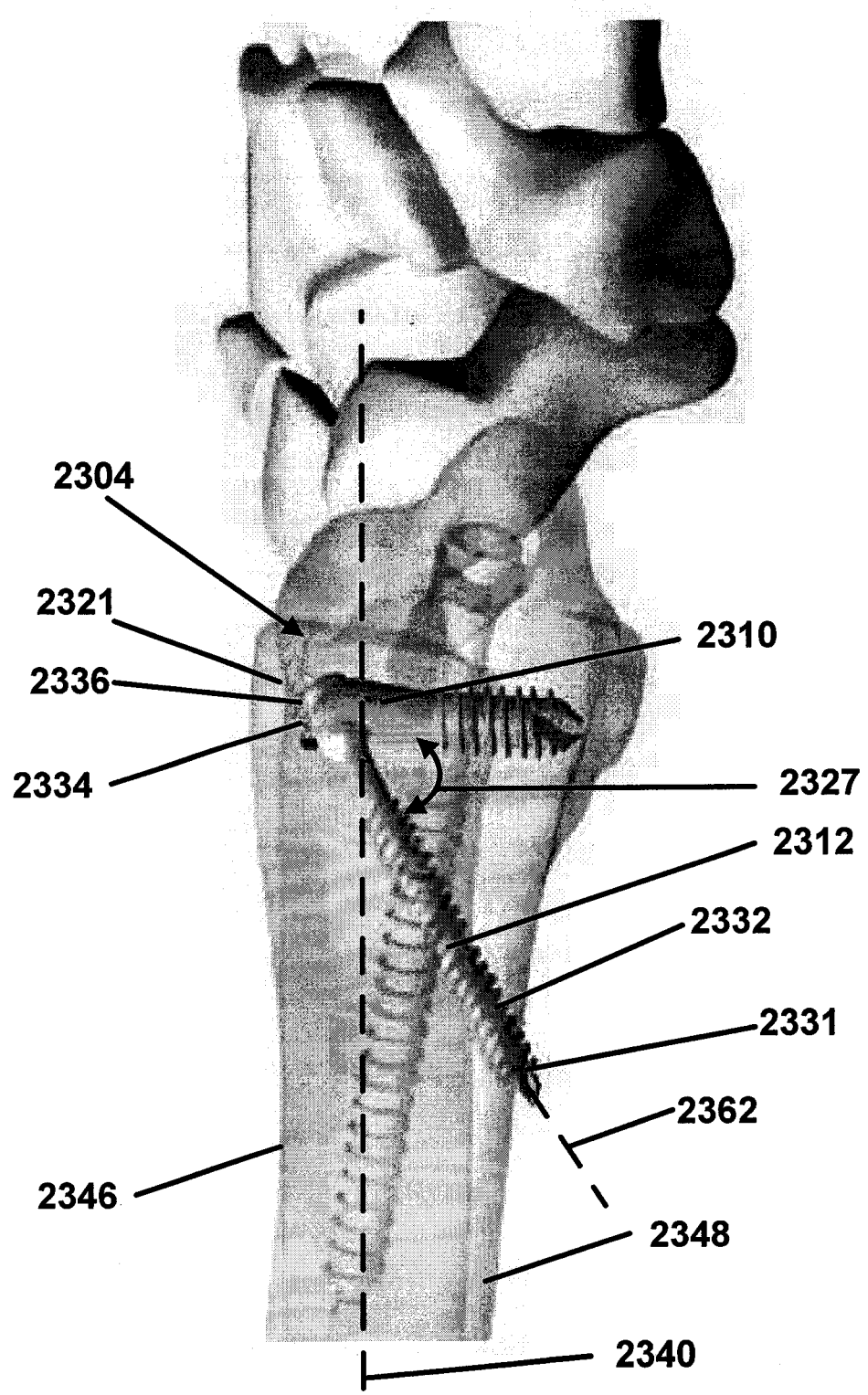
FIG. 23D is an image illustrating the ulnar construct of the intramedullary fixation assembly shown in FIGS. 23A and 23B according to an alternate embodiment of the invention.

For ease of understanding the following description of the orientation of intramedullary fixation assembly 2300 and its method of use, it should be understood that FIGS. 23A-23C illustrate a dorsal side view of a human wrist. That is, FIGS. 23A-C illustrate a perspective of the back of the hand and wrist. FIG. 23D illustrates a side view of a human wrist. FIGS. 23A-23D depict a radius bone 2314, an ulna bone 2315, an articular surface 2318 of radius bone 2314, a lunate articular surface 2319 of radius bone 2314, and a distal cortex 2321 of radius bone 2314. It should be understood that radial side 2342 refers to side of radius bone 2314 further away from ulna bone 2315, ulnar side 2344 refers to the side of radius bone 2314 closest to ulna bone 2315, dorsal side 2346 refers to the top of the hand and/or wrist, and volar side 2348 refers to the same side of the wrist as the palm of the hand. It should also be understood that saggital plane 2328 refers to the imaginary plane that extends between the distal end of radius bone 2314 to the proximal end of radius bone 2314, dividing radius bone 2314 into radial and ulnar portions. Finally, it should be understood that coronal plane 2340 is a plane that extends between from the distal end of radius bone 2314 to the proximal end of radius bone 2314 at a right angle to saggital plane 2328 and divides radius bone 2314 into dorsal and volar portions.

FIGS. 23A and 23B illustrate one embodiment of the orientation of intramedullary fixation assembly 2300 after it has been fixated to a radius bone 2314. As shown in FIGS. 23A and 23B, after intramedullary fixation assembly 2300 has been fixated to radius bone 2314, tapered screw member 2306 of radial construct 2302 preferably lies above a fracture 2316 of radius bone 2314 but below articular surface 2318 of radius bone 2314 in a radial to ulnar orientation. Specifically, the length or longitudinal axis of tapered screw member 2306 is aligned substantially parallel to articular surface 2318. Threads 2320 of tapered screw member 2306 are preferably fixated to the subchondral bone and/or the cortical bone of radius bone 2314 in order to provide a strong fixation. Aperture 2322 of tapered screw member 2306 is preferably oriented in a direction generally parallel to saggital plane 2328 and is located on the radial side 2342 of radius bone 2314 generally facing outwards toward the radial side 2342 of radius bone 2314. Moreover, the length of tapered screw member 2306 extends generally horizontal from aperture 2322 across radius bone 2314 towards the ulnar side 2344 of radius bone 2314.

Lag screw member 2308 is coupled to tapered screw member 2306 via any known method discussed above. For example and as described above, when coupling lag screw member 2308 to tapered screw member 2306, lag screw member 2308 slides through aperture 2322 of tapered screw member 2306 until bulbous portion 2324 of lag screw member 2308 mates with aperture 2322. Lag screw member 2308 is preferably coupled to tapered screw member 2306 via a Morse taper coupling mechanism, a rotational locking mechanism, a threaded connection, or a combination thereof. The Morse taper allows for a locked interference fit with aperture 2322 when bulbous portion 2324 resides within aperture 2322. A threaded connection provides a more stable and stronger locking fit between aperture 2322 and bulbous portion 2324. Starting at bulbous portion 2324, lag screw member 2308 extends from the radial side 2342 of radius bone 2314 through fracture 2316 in a generally longitudinal direction along the length of radius bone 2314 and along axis 2360, the same of aperture 2322, towards the ulnar side 2344 of radius bone 2314, where it is fixed to radius bone 2314. After lag screw member 2308 is coupled to tapered screw member 2306, an acute angle 2325 is formed between the two members. Moreover, the threads 2326 of lag screw member 2308 are preferably coupled across fracture 2316 and into radius bone 2314. Lag screw member 2308 is preferably fixated to radius bone 2314 so as to create a bicortical purchase 2330.

As shown in FIGS. 23A and 23B, after intramedullary fixation assembly 2300 has been fixated to radius bone 2314, tapered screw member 2310 of ulnar construct 2304 preferably lies below the dorsal cortex 2321 in a dorsal to volar orientation. Specifically, the length of tapered screw member 2310 generally runs parallel to the lunate articular surface 2319 of radius bone 2314. Threads 2332 of tapered screw member 2310 are preferably fixated to the subchondral and/or cortical bone of radius bone 2314 in order to provide a strong fixation. Aperture 2334 of tapered screw member 2310 is preferably oriented approximately 45 degrees to the coronal plane 2340 (FIG. 23D). Moreover, aperture 2334 of tapered screw member 2310 is located on the dorsal side 2346 (FIG. 23D) of radius bone 2314 while the length of tapered screw member 2310 extends generally horizontal from aperture 2334 towards the volar side 2348 (FIG. 23D) of radius bone 2314.

Lag screw member 2312 is coupled to tapered screw member 2310 via any known method discussed above. For example and as described above, when coupling lag screw member 2312 to tapered screw member 2310, lag screw member 2310 slides through aperture 2334 of tapered screw member 2310 until bulbous portion 2336 of lag screw member 2312 mates with aperture 2334. Lag screw member 2312 is preferably coupled to tapered screw member 2310 via a Morse taper coupling mechanism, a rotational locking mechanism, a threaded connection, or a combination thereof. The Morse taper allows for a locked interference fit with aperture 2334 when bulbous portion 2336 resides within aperture 2334. A threaded connection provides a more stable and stronger locking fit between aperture 2334 and bulbous portion 2336. Starting at bulbous portion 2336, lag screw member 2312 extends from the dorsal side 2346 of radius bone 2314 through fracture 2316 in a generally longitudinal direction along the length of radius bone 2314 and along axis 2362, the same axis of aperture 2334, towards the volar side 2348 of radius bone 2314, where it is fixed to radius bone 2314. After lag screw member 2312 is coupled to tapered screw member 2310, an acute angle 2327 is formed between the two members. Moreover, the threads 2332 of lag screw member 2312 are preferably coupled across fracture 2316 and into radius bone 2314. Lag screw member 2312 may also be fixated to radius bone 2314 so as to create a bicortical purchase 2331 (FIG. 23D).

Radial construct 2302, as shown in FIG. 23C, is provided to apply a strong and/or rigid fixation to radius bone 2314 and compression at an acute angle 2350, 2352, and 2354 that is either variable between 0 and 90 degrees or fixed at a predetermined angle prior to compression. Radial construct 2302 provides rigid fixation to radius bone 2314 by fixating into the strongest bone near the fracture or fracture site 2316. For example, tapered screw member 2306 of radial construct 2302 is generally fixated into the subchondral bone and/or cortical bone near the fracture. Radial construct 2302 provides compression at either a variable acute angle 2350, 2352, and 2354 or a fixed angle 2350, 2352, and 2354 by employing any of the combination of screws previously described above. For example, the use of hybrid screw member 2005 as tapered screw member 2306 in conjunction with polyaxial screw member 2010 as lag screw member 2308 may be provided to apply compression at an acute angle that is variable between 0 and 90 degrees prior to compression, after which compression is applied to set the angle of fixation. As a further example, the use of a hybrid screw member 2005 as tapered screw member 2306 in conjunction with tapered screw member 2105 as lag screw member 2308 may be provided to apply compression at an acute angle that is fixed at a predetermined angle between 0 and 90 degrees depending on the bone segments that are being compressed.

As shown in FIG. 23D, ulnar construct 2304 reinforces and/or sets the volar tilt in radius bone 2314, provides rotational control, maintains proper alignment of the fractured bone, and compresses a fracture at an acute angle 2327 that is either variable between 0 and 90 degrees or fixed at a predetermined angle prior to compression. Ulnar construct 2304 provides the aforementioned benefits by fixating into the strongest bone near the fracture or fracture site 2316. For example, tapered screw member 2310 of ulnar construct 2304 is generally fixated into the subchondral bone and/or cortical bone near the fracture. Ulnar construct 2304 provides compression at either a variable acute angle or a fixed angle by employing any of the combination of screws previously described above. For example, the use of hybrid screw member 2005 as tapered screw member 2306 in conjunction with polyaxial screw member 2010 as lag screw member 2308 may be provided to apply compression at an acute angle that is variable between 0 and 90 degrees prior to compression, after which compression is applied to set the angle of fixation. As a further example, the use of a hybrid screw member 2005 as tapered screw member 2306 in conjunction with tapered screw member 2105 as lag screw member 2308 may be provided to apply compression at an acute angle that is fixed at a predetermined angle between 0 and 90 degrees depending on the bone segments that are being compressed.

Figure 24A:
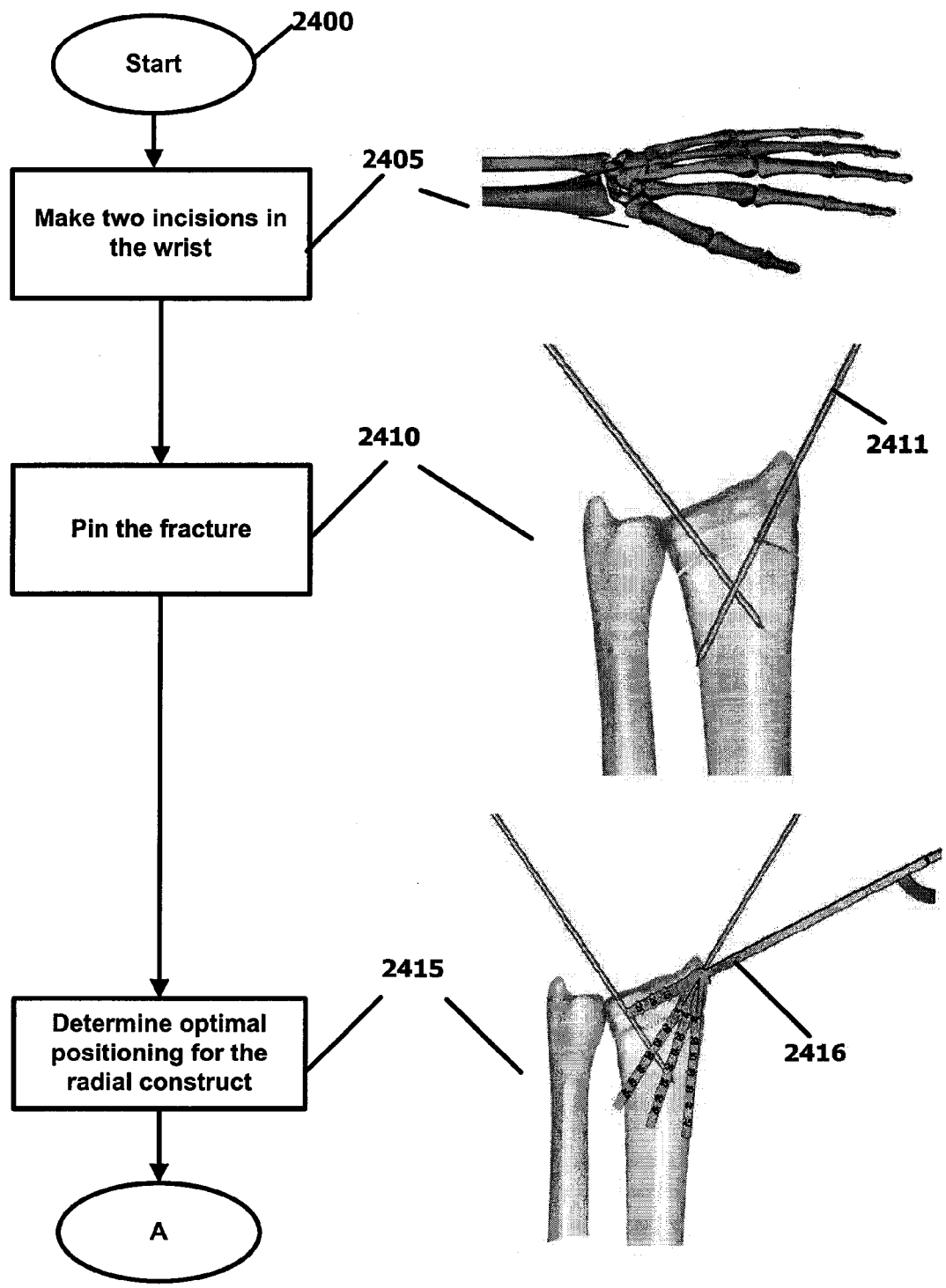
FIG. 24A-24G is a flow chart illustrating the method of fixating the intramedullary fixation assembly shown in FIGS. 23A-23D to a bone in a patient's wrist along with corresponding images for each respective step of the method according to an alternate embodiment of the invention.
Figure 24B:
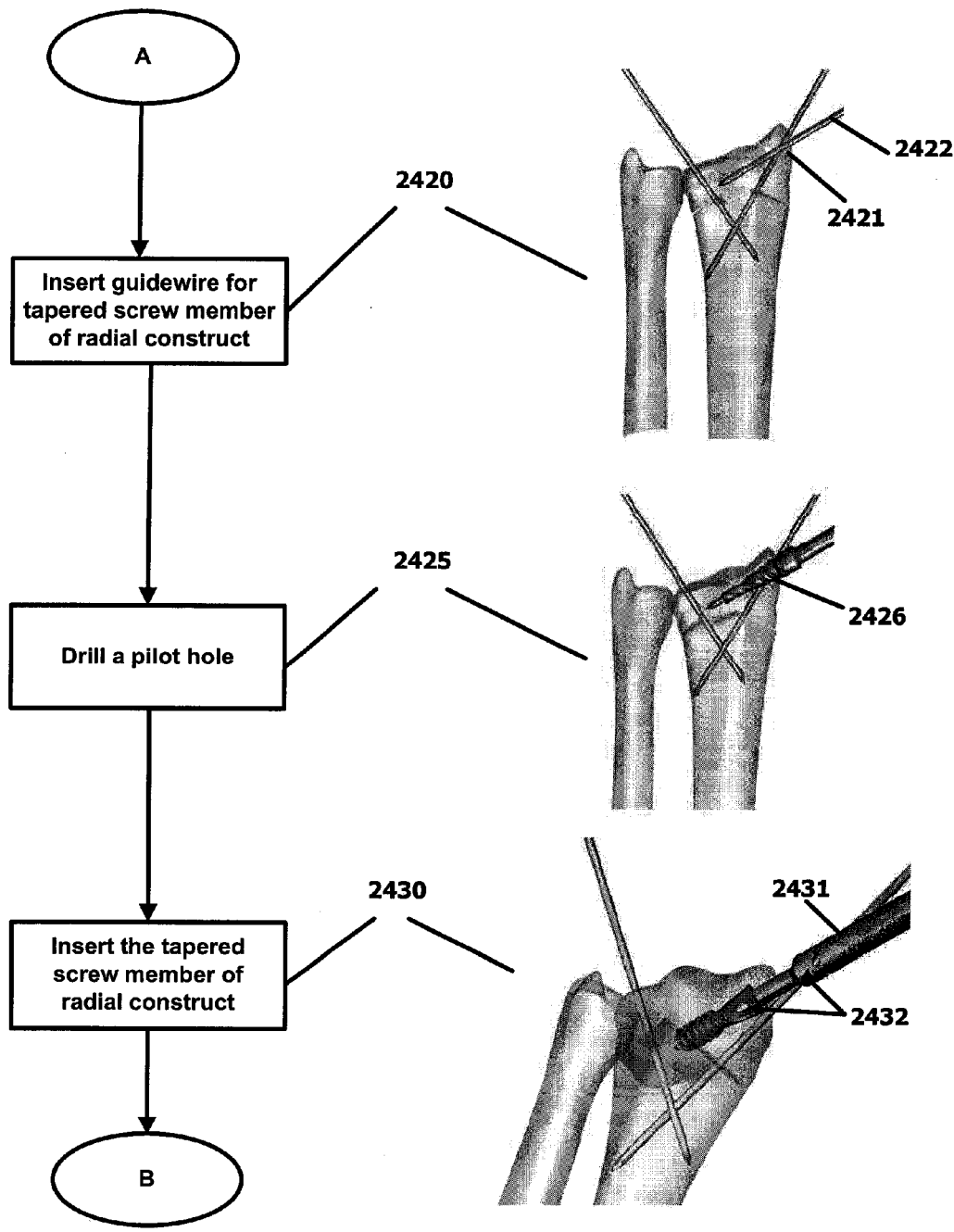
Figure 24C:
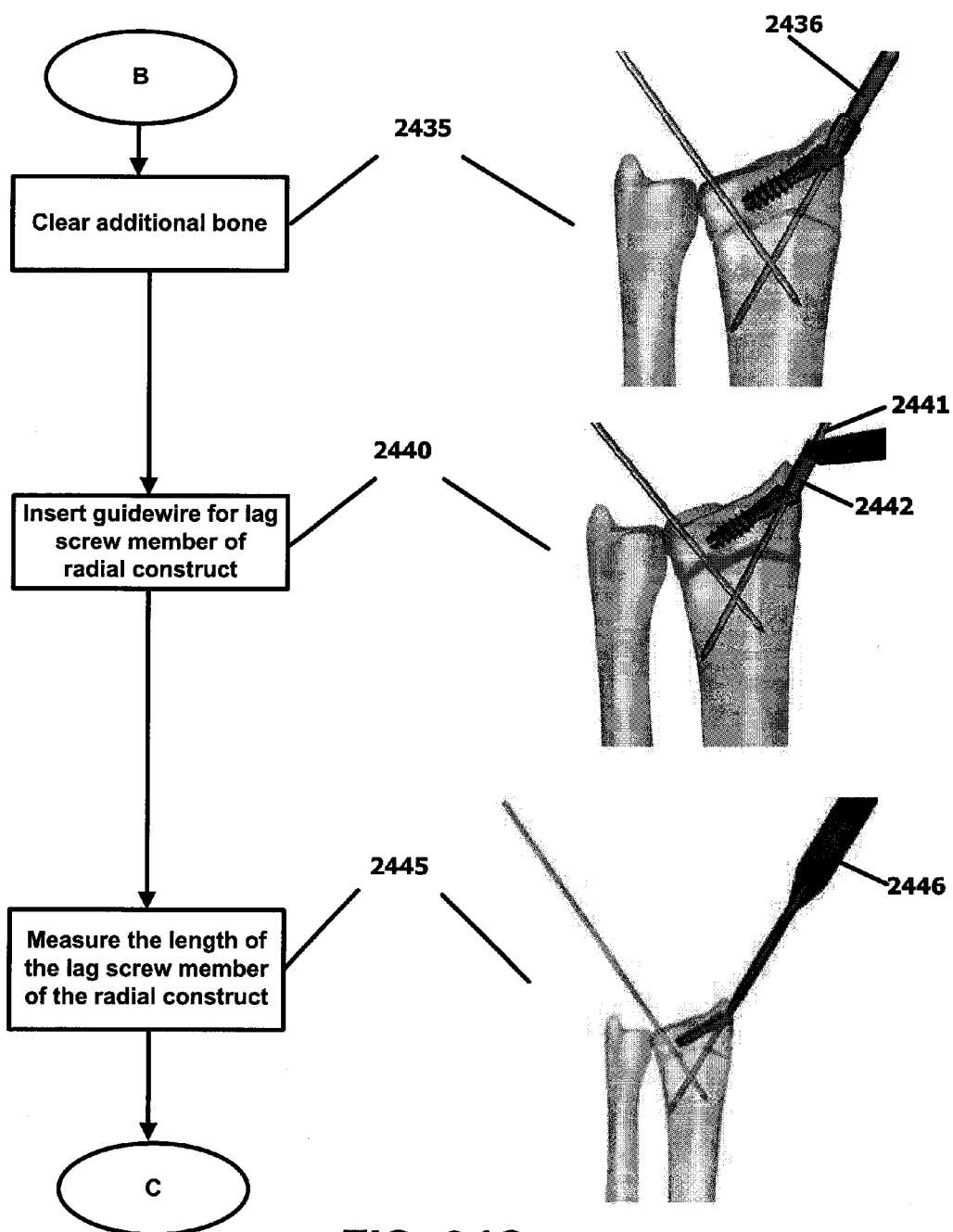

As shown in FIGS. 23A-23D and 24A-24G, intramedullary fixation assembly 2300 may be utilized to fixate a fracture 2316 of a human distal radius 2314. More particularly, the method shown in FIGS. 24A-24G describes the steps for implementing intramedullary fixation assembly 2300 in order to fixate a fracture of the distal radius 2314. As shown in FIG. 24A, the method starts in step 2400 and proceeds to step 2405, whereby two incisions are made in the wrist. A longitudinal incision about 1 cm to about 2 cm in length is performed over the 5$^{th}$ dorsal compartment and radiolunate joint. A secondary incision, about 2 cm to about 3 cm in length is performed over the radial column, beginning at the styloid tip. Soft tissue preparation is then performed to expose the distal radius. In step 2410, the fracture is reduced and provisionally pinned, prior to hardware implementation, via a crossing wire method. During this step the radial pin 2411 (FIG. 24A) is placed slightly volar to the saggital midplane to allow for preparation of ulnar construct 2304. Next, in step 2415, the optimal positioning for radial construct 2302 is determined using the external template 2416 (FIG. 24A) and based on the placement and angle options available for tapered screw member 2306.

Next, in step 2420, the guidewire 2422 (FIG. 24B) for tapered screw member 2306 is inserted through the radial styloid 2421 (FIG. 24B) in the intended orientation and about 5 mm to about 10 mm above the fracture or fracture site 2316. Moreover, the guidewire 2422 should be placed about 3 mm to about 4 mm from the closest point of the articular surface 2318 to prevent threads 2320 of tapered screw member 2306 from breaking through the articular cartilage. After the guidewire 2422 has been inserted, the positioning of the guidewire should be reviewed under a fluoroscope. In step 2425 a pilot hole is drilled, using an appropriately sized drill 2426 (FIG. 24B), along the guidewire 2422 to a measured depth. For example, if the surgeon intends on using a 4.6 (Gold) tapered screw member 2306 the size of the drill should be approximately 2.0 mm. If, however, the surgeon intends on using either a 6.6×30 degrees (Green) tapered screw member 2306 or a 6.6×45 degrees (Teal) tapered screw member 2306, the size of the drill should be about 3.4 mm. Here, the surgeon determines the length of the tapered screw member 2306 necessary for fixation by monitoring the depth of the drilled pilot hole. If necessary, the pilot hole is reamed using an appropriate reamer. For example, if the surgeon intends on using the Gold tapered screw member 2306, a 4.6 reamer would be appropriate for reaming the bone. If, however, the surgeon intends on using either the Green or Teal tapered screw member 2306, a 6.6 reamer is the appropriate tool for reaming. In step 2430 tapered screw member 2306 of radial construct 2302 is inserted into the pilot hole. Here, the surgeon first selects the appropriate sized tapered screw member 2306, aligns tapered screw member 2306 to a screwdriver 2431 (FIG. 24B) by aligning the laser marked arrows 2432 (FIG. 24B) on both tapered screw member 2306 and the screwdriver 2431. Using the screwdriver 2431, tapered screw member 2306 is inserted about 5 mm to about 10 mm above the fracture or fracture site 2316 and about 3 mm to about 4 mm from the articular surface 2318. Aperture 2322 is preferably aligned, using the laser arrows 2432, towards the intended direction of lag screw member 2308. Preferably, tapered screw member 2306 is aligned so that aperture 2322 is oriented slightly, about 10 degrees, dorsal to the saggital plane 2328. In other non-limiting embodiments, tapered screw member 2306 may be inserted by impaction, by press fit, by reaming a hole in the intramedullary canal (not shown) or substantially any other similar strategy or technique.

Figure 24D:
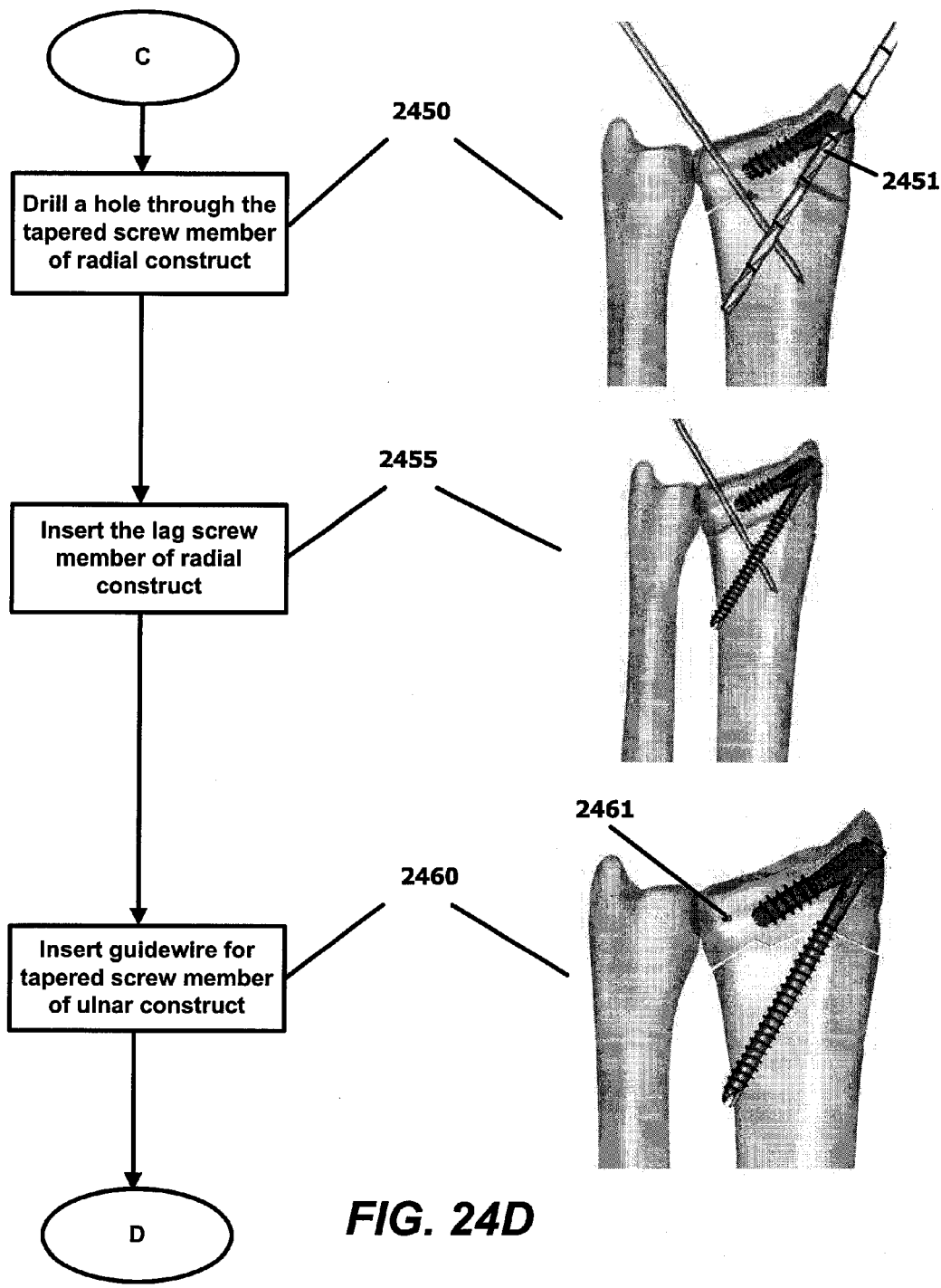

In order to gain access to aperture 2322, any obstructing bone is preferably removed by hand using an appropriate sized clearing tool 2436 (FIG. 23C) in step 2435. For example, if the surgeon intends on using the Gold tapered screw member 2306, a 4.6 clearing tool would be appropriate for removing bone from aperture 2322. If, however, the surgeon intends on using either the Green or Teal tapered screw member 2306, a 6.6 clearing tool would be appropriate. Clearing the excess bone from aperture 2322 allows the guide 2441 (FIG. 24C) of a guidewire 2422 (FIG. 24C) to seat properly within aperture 2322. Alternatively, a rongeur (not shown) can be used to remove any impinging bone. In step 2440, an appropriate guidewire 2441 (FIG. 24C) for lag screw 2308 of radial construct 2302 is inserted into aperture 2322 of tapered screw member 2306 preferably until the guide 2442 (FIG. 24C) is secure in the tapered portion of aperture 2322 and only a small portion of the depth line is visible at the apex of tapered screw member 2306. In the event the guide 2442 is not seated properly, it must be verified that aperture 2322 is sufficiently cleared of bone. If there is still bone blocking aperture 2322, it must be cleared using clearing tool 2436, as described with respect to step 2435. If the guide 2442 is seated properly, the position of the guidewire 2441 is then verified via a fluoroscope. Next, in step 2445, the length of lag screw 2308 of radial construct 2302 is measured by preferably placing a depth gauge 2446 (FIG. 24C) over the guidewire 2441 and down to the bone. A hole is then drilled completely through the ulnar cortex of radius 2314, in step 2450. This is done by drilling over the guidewire 2441 and through aperture 2322 of tapered screw member 2306 with an appropriate drill 2451 (FIG. 24D). Next, in step 2455, lag screw member 2308 of radial construct 2302 is inserted through aperture 2322 of tapered screw member 2306. Preferably, lag screw member 2308 is inserted into the hole until two finger pressure is felt and bulbous head 2324 of lag screw 2308 is locked in aperture 2322 of tapered screw member 2306 via any of the previously described methods. This completes the fixation of radial construct 2302 into distal radius 2314. Once the fixation is established, all provisional guidewires are removed.

Figure 24E:
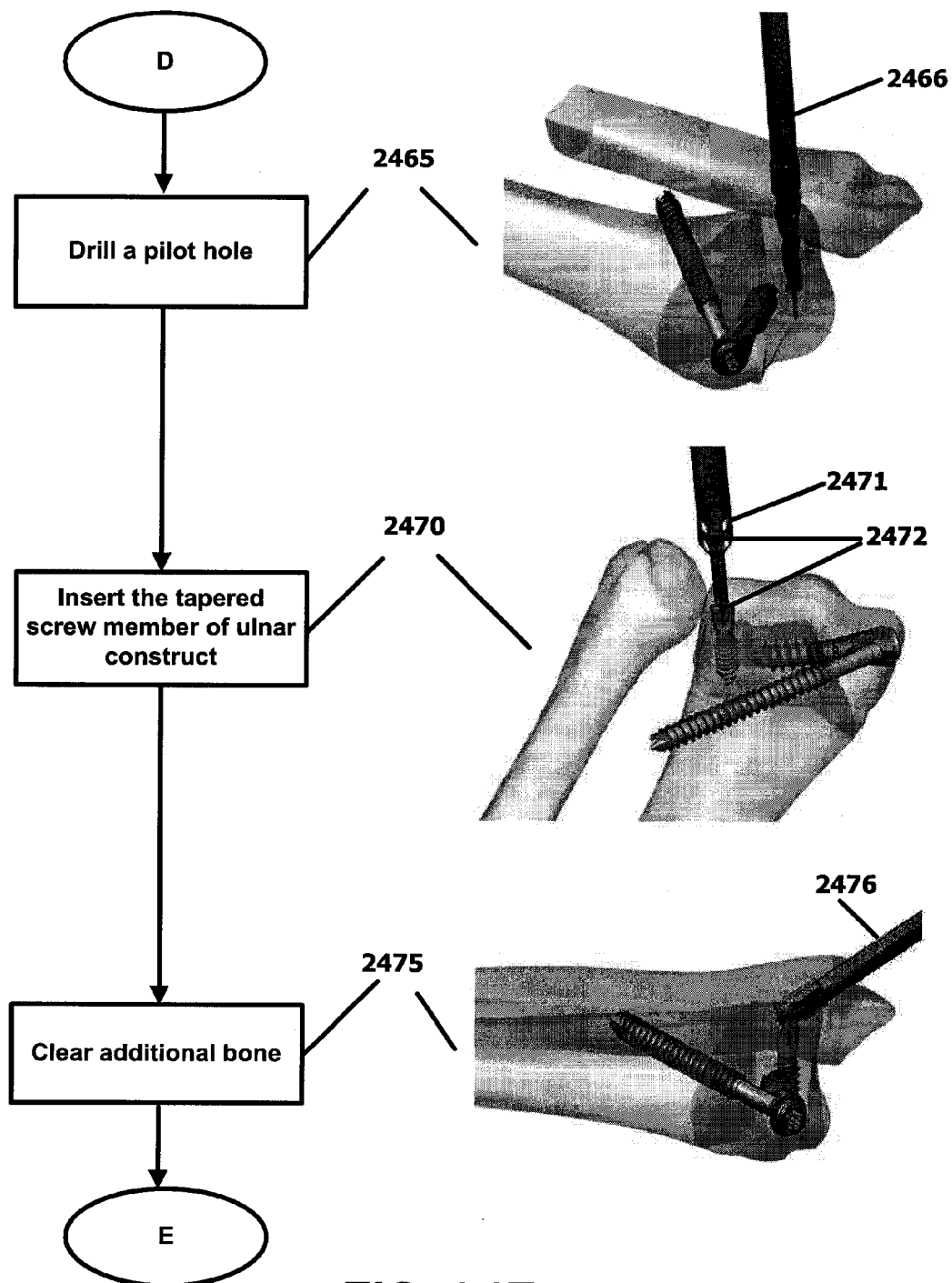

Next, in step 2460, an appropriate guidewire 2461 (FIG. 24D) is inserted into radius bone 2314 in a dorsal to volar orientation in preparation to insert tapered screw member 2310 of ulnar construct 2304. The orientation of the guidewire 2461 is preferably placed slightly distal to proximal so that it runs parallel to the lunate articular surface. The insertion point should be placed about 5 mm to about 10 mm above the fracture or fracture site 2316, at least about 4 mm to about 5 mm away from the articular edge of radius bone 2314, and about 4 mm to about 5 mm lateral to the sigmoid notch 2323 (FIG. 23C) of the Distal Radial Ulnar Joint ("DRUJ"). After the guidewire 2461 is inserted, the surgeon, under a fluoroscope, reviews its positioning. In step 2465, a pilot hole is drilled from the surface of the bone where the guidewire 2461 is located down to the volar cortex. The pilot hole is drilled using an appropriately sized drill 2466 (FIG. 24E). For example, if the surgeon intends on using a Gold tapered screw member 2310, the size of the drill should be about 2.0 mm. If, however, the surgeon intends on using either the Green or a 6.6×45 degrees (Seafoam) tapered screw member 2310, the size of the drill should be about 3.4 mm. Here, the surgeon determines the length of the tapered screw member 2310 necessary for fixation by monitoring the depth of the drilled pilot hole. The surgeon may also have to ream the bone using an appropriate reamer. For example, if the surgeon intends on using the Gold tapered screw member 2310, a 4.6 reamer would be appropriate for reaming the bone. If, however, the surgeon intends on using either the Green or Seafoam tapered screw member 2310, a 6.6 reamer would be appropriate.

In step 2470, tapered screw member 2310 of ulnar construct 2304 is inserted into the pilot hole. Here, the surgeon first selects the appropriate sized tapered screw member 2310, aligns tapered screw member 2310 to a screwdriver 2471 (FIG. 24E) by aligning the laser marked arrows 2472 (FIG. 24E) on both tapered screw member 2310 and the screwdriver. Using the screwdriver 2471, tapered screw member 2310 is inserted about 2 mm below the dorsal cortex 2321 and aperture 2334 is aligned, using the laser arrows 2472, towards the intended direction of lag screw member 2312. Preferably, aperture 2334 is aligned approximately 45 degrees to coronal plane 2340. In order to gain access to aperture 2334, any obstructing bone is preferably removed by hand using an appropriate sized clearing tool 2476 (FIG. 24E) in step 2475. For example, if the surgeon intends on using the Gold tapered screw member 2310, a 4.6 clearing tool would be appropriate for removing bone from aperture 2334. If, however, the surgeon intends on using either the Teal or Seafoam tapered screw member 2310, a 6.6 clearing tool would be appropriate. Clearing the excess bone from aperture 2334 allows the guide 2482 (FIG. 24F) of a guidewire 2481 (FIG. 24F) to seat properly within aperture 2334. Alternatively, a rongeur (not shown) can be used to remove any impinging bone. Any difficulty seating the guide 2482 could be due to bony interference at aperture 2334. Thus, any bone impinging on aperture 2334 should be removed.

Figure 24F:
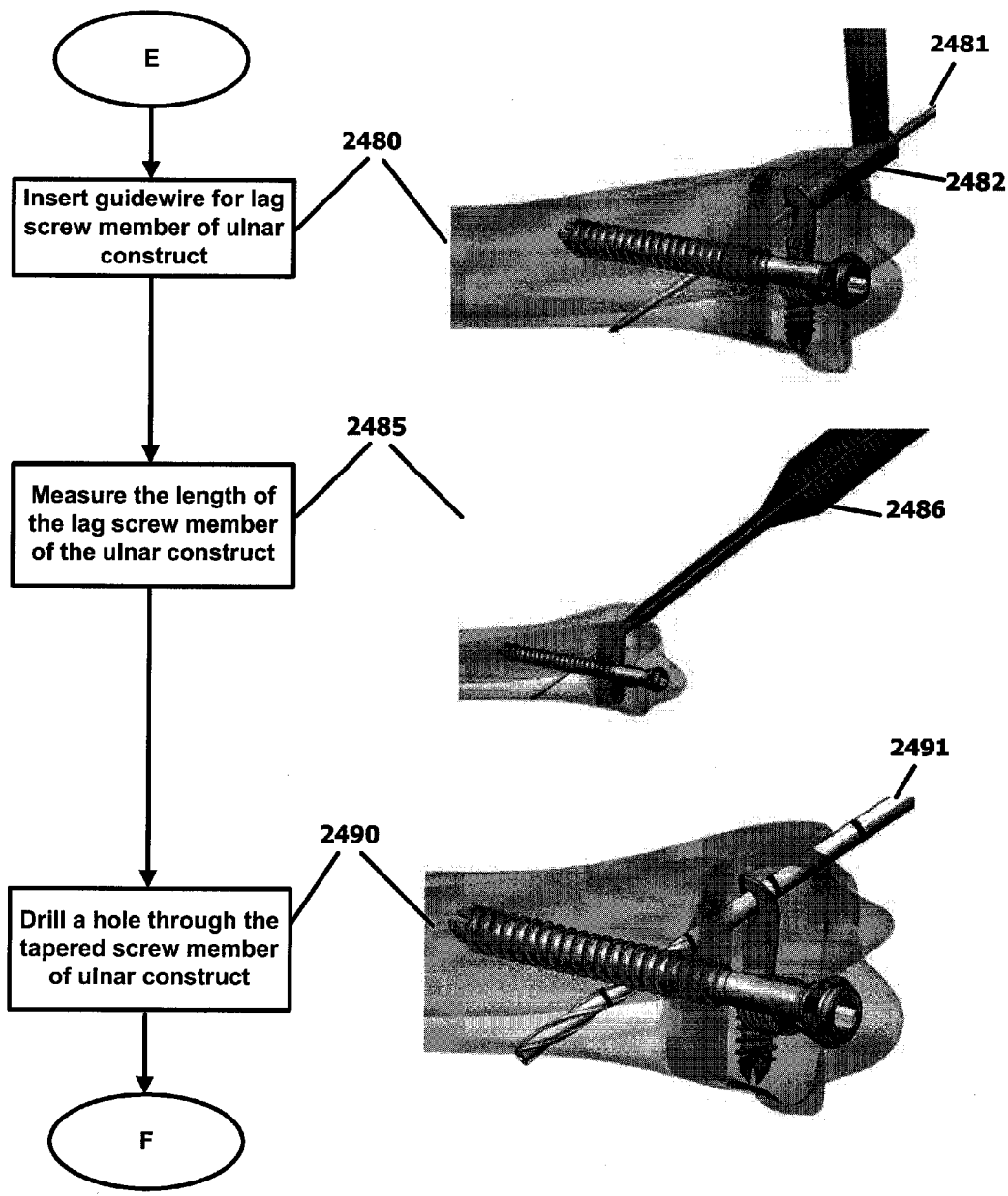
Figure 24G:
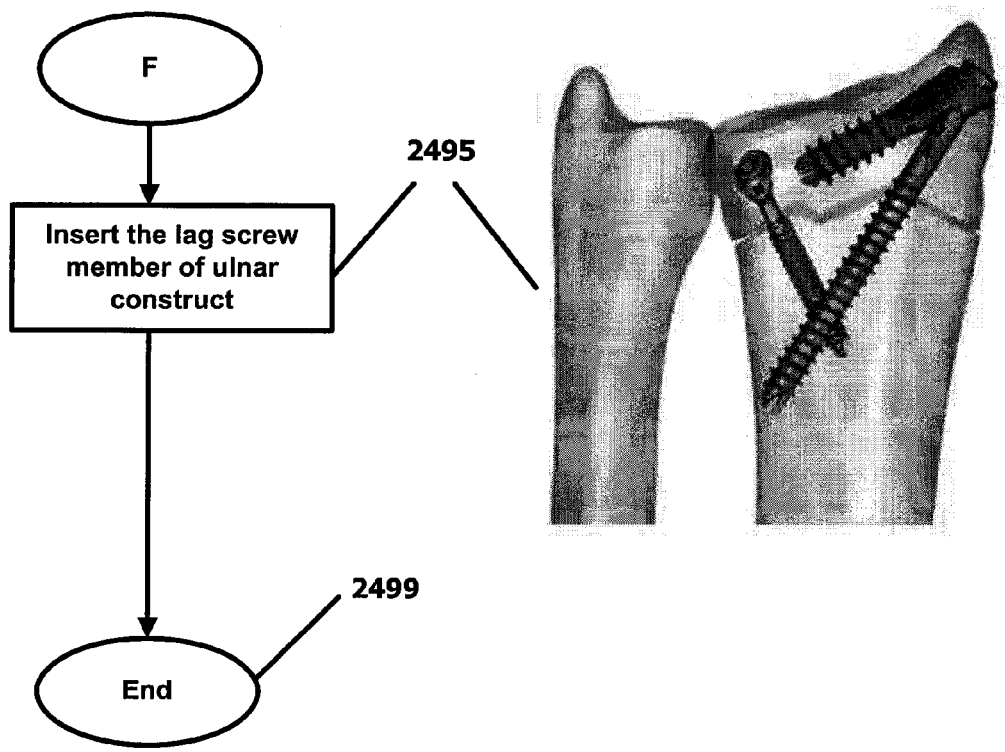

In step 2480, an appropriate guide 2482 (FIG. 24F) of guidewire 2481 (FIG. 24F) for lag screw 2312 of ulnar construct 2304 is inserted into aperture 2334 of tapered screw member 2310 preferably until the guide 2482 is secure in the tapered portion of aperture 2334 and only a small portion of the depth line is visible at the apex of tapered screw member 2310. In the event the guide 2482 is not seated properly, it must be verified that aperture 2334 is sufficiently cleared of bone. The position of the guidewire 2481 is then verified via a fluoroscope. Next, in step 2485, the length of lag screw 2312 of ulnar construct 2304 is measured by preferably placing a depth gauge 2486 (FIG. 24F) over the guidewire 2481 and down to the bone. A hole is then drilled completely through the volar cortex of radius bone 2314, in step 2490. This is done by drilling over the guidewire 2481 and through aperture 2334 of tapered screw member 2310 with an appropriate drill 2491 (FIG. 24F). Next, in step 2495, lag screw member 2312 of ulnar construct 2304 is inserted through aperture 2334 of tapered screw member 2310. Preferably, lag screw member 2312 is inserted into the hole until two finger pressure is felt and bulbous head 2336 of lag screw 2312 is locked in aperture 2334 of tapered screw member 2310 via any of the previously described methods. This completes the fixation of ulnar construct 2304 into the distal radius bone 2314. Once the fixation is established, all provisional guidewires are removed. The method of fixating a distal radius fracture ends in step 2499.

It should be appreciated that a plurality of intramedullary fixation assemblies, such as intramedullary fixation assembly 2300, may be inserted into any of the bones of the body, such as but not limited to, radial, humerus, tibia, and femur, in order to fixate fractures, without limiting the scope of the invention. Thus, the orientation of intramedullary fixation system 2300 and method of use, in one non-limiting embodiment, is utilized to fixate a distal radius fracture by rigidly fixating two tapered screw members 2306 and 2310 to the subchondral bone and/or cortical bone and applying acute angle compression to the fracture by coupling two lag screw members 2308 and 2312 to the two tapered screw members 2306 and 2310, respectively. This orientation and method of use maintains reduction of the fracture by realigning the bone to its natural anatomical position, which allows for quicker healing time and earlier mobilization of the patient. Moreover, this orientation and method minimize the size of the incisions necessary to perform the surgery, minimize soft issue and tendon disruption and/or misplacement, and reduce and/or eliminate hardware profiles. It should be appreciated that the intramedullary fixation assembly 2300 is delivered through a longitudinal incision over the 5$^{th}$ dorsal compartment and radiolunate joint and a secondary incision over the radial column, thereby reducing the disruption to the tissues and/or the tendons while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 2300 may be utilized with graft material (i.e., autograft, allograft or other biologic agent).

Intramedullary fixation assembly 2300, an alternate embodiment of the invention, is provided generally for the reduction and internal fixation of arthrodesis, osteotomy, intra-articular and extra-articular fractures and non-unions of bones and joints of the hand, foot, arm, leg, and various other body parts and to apply acute angle compression to bones. In particular, intramedullary fixation assembly 2300 provides orthogonal multi-plane fixation and bicortical cross screw fixation to bones. Intramedullary fixation assembly 2300 preferably delivers the strength necessary to maintain sufficient reduction and/or fixation of a fractured bone, maximizes cortical bone contact, retains bones in most anatomically correct position, prevents screw head break out, minimizes the size of the incision(s) necessary to install the hardware, minimizes soft tissue and tendon disruption and/or displacement, stabilizes fixation of the fracture, eases mobility for the patient, provides early post-operation mobilization of the fracture bone, and reduces and/or eliminates hardware profiles. Moreover, intramedullary fixation assembly 2300 generally provides a more stable and rigid fixation than the prior art because it is fixed to the strongest bone near the fracture and because it redistributes the force normally placed on the head of a screw along the threads of the assembly.

It should be understood and appreciated that while the orientation of and the method for implementing intramedullary fixation assembly 2300, as described above with respect to FIGS. 23A-24G, is disclosed in connection with fixating distal radius fractures, the orientation of and method for implementing intramedullary fixation assembly 2300 may be modified to provide reduction and internal fixation of arthrodesis, intra-articular and extra-articular fractures and non-unions of bones and joints of the hand, foot, arm, leg, and various other body parts, and osteotomies for each of these applications, without limiting the scope of the invention.

As shown in FIGS. 23A-23D, intramedullary fixation assembly 2300 is provided to create subchondral and/or cortical cross-beam fixation, which provides stability across the fracture; apply compression at an acute angle that is variable between 0 and 90 degrees prior to compression; reinforce and/or set the volar tilt; and generate rotational control.

While the orientation of intramedullary fixation assembly 2300, as shown in FIGS. 23A-23D and described above, and its method of use, as described with respect to FIGS. 24A-24G, has been described in connection with the fixation of a fracture of the distal radius, it should be appreciated that a similar or modified orientation and method for fixating a fracture or an osteotomy may be implemented in connection with the fixation of various other fractures, without limiting the scope of the invention. Such fractures include but are not limited to proximal radius fractures, distal and proximal humerus fractures, distal and proximal tibia fractures, distal and proximal femur fractures, and the like. It should further be understood that while the orientation of intramedullary fixation assembly 2300 and its method of use may be modified, assembly 2300 and its method of use may be implemented anywhere in the body where plating is used to fixate fractures, without departing from the spirit of the invention. Finally, while specific measurements, tools, orientations, and methods were disclosed above with respect to intramedullary fixation assembly 2300 and its method of use, it should be appreciated that these specific measurements, tools, orientations, and methods may be modified, without limiting the scope of the invention.

It should also be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

The invention claimed is:

1. An intramedullary fixation assembly for bone fixation, comprising:
   a first screw member extending from a first end to a second end along a first longitudinal axis, the first screw member having a head portion at the first end comprising a first aperture at a terminal end of the first end of the first screw member, a first shaft extending from the head portion to the second end, and a bore extending along a bore axis from the first aperture to a second aperture on an exterior surface of the first screw member;
   a second screw member extending from a first end to a second end along a second longitudinal axis, the second screw member having a bulbous portion at the first end of the second screw member and a second shaft extending from the bulbous portion to the second end of the second screw member;
   a first plurality of threads disposed substantially along a circumference of an interior surface of the bore; and
   a second plurality of threads disposed substantially along a circumference of an exterior surface of the bulbous portion, wherein the first plurality of threads couple with the second plurality of threads to form a threaded connection between the first screw member and second screw member.

2. The fixation assembly of claim 1, wherein said first shaft comprises a first threaded portion for advancing said first screw member into a first bone or bone fragment.

3. The fixation assembly of claim 2, wherein said second shaft comprises a second threaded portion for advancing said second screw member into a second bone or bone fragment.

4. The fixation assembly of claim 3, wherein the second screw member couples to the first screw member by being inserted into the first aperture and through the bore and out of the second aperture and rotated until the second plurality of threads on the exterior surface of the bulbous portion of the second screw member engages the first plurality of threads on the interior surface of the bore at the first aperture of the first screw member and the second threaded portion extends out of the second aperture to engage the second bone or bone fragment.

5. The fixation assembly of claim 4, wherein the first screw member and the second screw member are configured to translate compression to the first bone or bone fragment and the second bone or bone fragment thereby drawing the bones or bone fragments together.

6. The fixation assembly of claim 1, wherein the first longitudinal axis and the bore axis define an angle.

7. The fixation assembly of claim 6, wherein the second screw member couples to the first screw member at the angle.

8. The fixation assembly of claim 7, wherein the angle is in the range of about 0 degrees to about 90 degrees.

9. The fixation assembly of claim 1, wherein the bulbous portion includes an aperture disposed along the second longitudinal axis.

10. The fixation assembly of claim 9, wherein the aperture of the bulbous portion has a hexagonal shape, a star shape, or a square shape.

11. The fixation assembly of claim 9, wherein the aperture of the bulbous portion is provided to receive a complementary shaped end of an instrument.

12. The fixation assembly of claim 1, wherein the first plurality of threads couple with the second plurality of threads to form a threaded locking connection between the first screw member and the second screw member.

13. The fixation assembly of claim 1, wherein the first plurality of threads couple with the second plurality of threads by rotating the bulbous portion of the second screw member.

14. The fixation assembly of claim 1, wherein the first plurality of threads and the second plurality of threads comprise reverse threads.

15. A fixation assembly for bone fixation, comprising:
   a first screw member comprising a first elongated body extending from a first end to a second end along a first longitudinal axis, a first threaded portion at the second end of the first elongated body for advancing said first screw member into a first bone or bone fragment, a first aperture at a terminal end of the first end of the first screw member, a bore extending along a bore axis from the first aperture to a second aperture on an exterior surface of the first elongated body, and first plurality of threads disposed substantially along the circumference of an interior surface of the bore; and
   a second screw member comprising a second elongated body extending from a first end to a second end along a second longitudinal axis, a second threaded portion at the second end of the second elongated body for advancing said second screw member into a second bone or bone fragment, a bulbous portion at a first end, and second plurality of threads disposed substantially along the circumference of an exterior surface of the bulbous portion;
   wherein the second screw member couples to the first screw member by being inserted into the first aperture and through the bore and out of the second aperture until the second plurality of threads of the bulbous portion engages the first plurality of threads of the bore and the second threaded portion of the second elongated body extends out of the second aperture to engage the second bone or bone fragment; and
   wherein the first screw member and the second screw member are configured to translate compression to the first bone or bone fragment and the second bone or bone fragment thereby drawing the bones or bone fragments together.

16. The fixation assembly of claim 15, wherein the first longitudinal axis and the bore axis define an angle, and wherein the second screw member couples to the first screw member at the angle.

17. The fixation assembly of claim 16, wherein the angle is in the range of about 0 degrees to about 90 degrees.

18. The fixation assembly of claim 15, wherein the first plurality of threads and the second plurality of threads comprise reverse threads.

19. A fixation assembly for bone fixation, comprising:
a first screw member comprising a first elongated body extending from a first end to a second end along a first longitudinal axis, a first threaded portion at the second end of the first elongated body, a first aperture at a terminal end of the first end of the first screw member, a bore extending along a bore axis from the first aperture to a second aperture on an exterior surface of the first screw member, and first plurality of threads disposed substantially along the circumference of an interior surface of the bore; and
a second screw member comprising a second elongated body extending from a first end to a second end along a second longitudinal axis, a second threaded portion at the second end of the second elongated body, a bulbous portion at a first end, and second plurality of threads disposed substantially along the circumference of an exterior surface of the bulbous portion;
wherein the first screw member is configured to be advanced into a first bone or bone fragment until the first threaded portion of the first elongated body engages the first bone or bone fragment;
wherein the second screw member couples to the first screw member by being inserted into the first aperture and through the bore and out of the second aperture and rotated until the second plurality of threads of the bulbous portion engages the first plurality of threads of the bore and the second threaded portion of the second elongated body extends out of the second aperture to engage the second bone or bone fragment; and
wherein the first screw member and the second screw member are configured to translate compression to the first bone or bone fragment and the second bone or bone fragment thereby drawing the bones or bone fragments together.

* * * * *